United States Patent
Kojima et al.

(10) Patent No.: US 10,351,892 B2
(45) Date of Patent: Jul. 16, 2019

(54) MUTANT-TYPE GLUCOSE DEHYDROGENASE AND USE THEREOF

(71) Applicants: ARKRAY, Inc., Kyoto (JP); Ultizyme International Ltd., Tokyo (JP)

(72) Inventors: Katsuhiro Kojima, Tokyo (JP); Kazushige Mori, Tokyo (JP)

(73) Assignees: ARKRAY, Inc., Kyoto (JP); Ultizyme International Ltd., Tokyo (JP)

( * ) Notice: Subject to any disclaimer, the term of this patent is extended or adjusted under 35 U.S.C. 154(b) by 11 days.

(21) Appl. No.: 15/337,630

(22) Filed: Oct. 28, 2016

(65) Prior Publication Data

US 2017/0121751 A1    May 4, 2017

(30) Foreign Application Priority Data

Oct. 29, 2015  (JP) ................................. 2015-213085

(51) Int. Cl.
C12N 9/04 (2006.01)
C12Q 1/00 (2006.01)

(52) U.S. Cl.
CPC ........... *C12Q 1/006* (2013.01); *C12N 9/0006* (2013.01); *C12Y 101/9901* (2013.01); *G01N 2333/904* (2013.01)

(58) Field of Classification Search
CPC .............. C12Q 1/006; C12Y 101/9901; C12N 9/0006; G01N 2333/904
See application file for complete search history.

(56) References Cited

U.S. PATENT DOCUMENTS

| | | | |
|---|---|---|---|
| 7,604,969 B2 * | 10/2009 | Yamaoka | C12N 9/0006 435/190 |
| 2012/0107903 A1 | 5/2012 | Sode et al. | |
| 2012/0142037 A1 | 6/2012 | Sode | |
| 2013/0102016 A1 | 4/2013 | Sode | |
| 2013/0168263 A1 | 7/2013 | Sode et al. | |
| 2014/0356887 A1 | 12/2014 | Sode et al. | |

FOREIGN PATENT DOCUMENTS

| | | |
|---|---|---|
| EP | 1860183 A1 | 11/2007 |
| JP | 2010-148368 A | 7/2010 |
| JP | 2012-090563 A | 5/2012 |
| WO | 2016/087937 A2 | 6/2016 |

OTHER PUBLICATIONS

Witkowski et al., Biochemistry 38:11643-11650, 1999.*
Tang et al., Phil Trans R Soc B 368:20120318, 1-10, 2013.*
Seffernick et al., J. Bacteriol. 183(8):2405-2410, 2001.*
Branden et al., Introduction to Protein Structure, Garland Publishing Inc., New York, p. 247, 1991.*
Sadowski et al., Current Opinion in Structural Biology 19:357-362, 2009.*
Extended European Search Report issued in corresponding European Patent Application No. 16195837.6 dated Feb. 3, 2017.
Database UniProt [Online], Accession No. E6WLY9 (Mar. 8, 2011).
Database UniProt [Online], Accession No. D8MMH7 (Oct. 5, 2010).
Office Action issued in corresponding European Patent Application No. 16195837.6 dated Dec. 20, 2018.

* cited by examiner

*Primary Examiner* — Delia M Ramirez
(74) *Attorney, Agent, or Firm* — Morgan, Lewis & Bockius LLP

(57) ABSTRACT

The present invention provides a mutant-type glucose dehydrogenase having glucose dehydrogenase activity and having decreased reactivity with xylose, wherein said mutant-type glucose dehydrogenase comprises a mutant-type α-subunit comprising an amino acid sequence of 520 to 550 amino acids comprising an amino acid sequence of 520 to 550 amino acids comprising SEQ ID NO: 21, SEQ ID NO: 22, SEQ ID NO: 23, SEQ ID NO: 24 and SEQ ID NO: 25 in this order from N-terminus to C-terminus, except that one or more amino acid residue(s) selected from the group consisting of the glycine at position 10 in SEQ ID NO: 23, the histidine at position 4 in SEQ ID NO: 24, and the asparagine at position 4 in SEQ ID NO: 25 is/are substituted with another/other amino acid(s).

13 Claims, 30 Drawing Sheets

Specification includes a Sequence Listing.

```
                              *         260         *         280         *         300
Sequence3         : IGAMYNGVHVEKAERAGAKLENAVVYKLETGDKRIVAALYKDTGAERVEGKYFVL : 283
WP_006396898.1    : IGAMYNGVHVEKAERAGAKLENAVVYKLETGDKRIVAALYKDTGAERVEGKYFVL : 283
WP_035974223.1    : IGAMYNGVHVEKAERAGAKLENAVVYKLETGDKRIAAIYKDTGADRVEGKYFVL : 283
EGD03130.1        : IGAMYNGVHVEKAERAGAKLDSAVVYKLETGDKRIAAIYKDTGADRVEGKYFVL : 283
WP_040131619.1    : IGAMYNGVHVEKAERAGAKLDSAVVYKLETGDKRIVAAIYKDTGADRVEGKYFVL : 283
WP_040140036.1    : IGAMYNGVHVQKAERAGAKLDSAVVYKLETGDKRIVAAIYKDTGADRVEGKYFVV : 283
WP_034204694.1    : IGAMYNGVHVEKAERAGAKLDSAVVYKLETGDKRIVAAIYKDTGADRVEGKYFVL : 283
WP_044843287.1    : IGAMYNGVHVEKAEQAGAKLDSAVVYKLETGDKRIVAALYKRTGASRVEGKYFVV : 283
WP_023476482.1    : IGAMYNGVHVEKAERAGAKLDSAVVYKLETGDKRIVAALYKDTGADRVEGKYFVL : 283
WP_027780833.1    : IGAMYNGVHVEKAERAGAKLDSAVVYKLETGDKRIVAALYKDTGADRVEGKYFVL : 283
WP_011658979.1    : IGAMYNGVHVEKAERAGAKLDSAVVYKLETGDKRIVAALYKDTGADRVEGKYFVV : 283
WP_050012791.1    : IGAMYNGVHVEKAERAGAKLDSAVVYKLETGDKRIVAALYKLTGAYRVEGKYFVL : 283
WP_011547562.1    : IGAMYNGVHVEKAERAGAKLDSAVVYKLETGDKRITAAIYKDTGADRVEGKYFVI : 283
WP_034202233.1    : IGAMYNGVHVEKAERAGAKLDSAVVYKLETGDKRIVAAIYKDTGADRVEGKYFVL : 283
WP_011349244.1    : IGAMYNGVHVEKAERAGAKLDSAVVYKLETGDKRITAAVYKDTGADRVEGKYFVI : 283
WP_034180249.1    : IGAMYNGVHVEKAERAGAKLENAVVYKLETGNKRIVAALYKDSGADRVEGKYFVV : 283
WP_006752014.1    : IGAMYNGVHVEKAERAGAKLDSAVVYKLETGDKRIVAALYKDTGADRVEGKYFVV : 283
WP_047903069.1    : IGAMYNGVHVEKAERAGAKLENAVVYKLETGDKRITAAVYKDSGADRVEGKYFVV : 283
YP_002234347      : IGAMYNGVHVEKAERAGAKLDSAVVYKLETGDKRIVAAIYKDTGADRVEGKYFVL : 283
WP_039320756.1    : IGAMYNGVHVEKAERAGAKLDSAVVYKLETGDKRINAAVYKDTGADRVEGKYFVI : 283
WP_011882360.1    : IGAMYNGVHVEKAERAGAKLDSAVVYKLETGDKRIVAALYKDTGADRVEGKYFVL : 283
WP_021162033.1    : IGAMYNGVHVEKAERAGAKLDSAVVYKLETGDKRITAAVYKDTGADRVEGKYFVI : 283
WP_014724779.1    : IGAMYNGVHVEKAERAGAKLDSAVVYKLETGDKRIVAAIYKDTGADRVEGKYFVL : 283
WP_012366205.1    : IGAMYNGVHVEKAERAGAKLDSAVVYKLETGDKRIVAALYKDTGADRVEGKYFVV : 283
WP_046548034.1    : IGAMYNGVHVEKAERAGAKLDSAVVYKLETGDKRITAAVYKDTGADRVEGKYFVI : 283
WP_039351161.1    : IGAMYNGVHVEKAELAGAKLDSAVVYKLETGDKRITAAVYKDTGADRVEGKYFVI : 283
WP_027791851.1    : IGAMYNGVHVEKAERAGAKLDSAVVYKLETGDKRITAAVYKDTGADRVEGKYFVI : 283
WP_047849808.1    : IGAMYNGVHVEKAERAGAKLDSAVVYKLETGDKRITAAVYKRTGADRVEGKYFVI : 283
WP_043184375.1    : IGAMYNGVHVEKAERAGAKLDSAVVYKLETGDKRITAAVYKDTGADRVEGKYFVI : 283
WP_014899066.1    : IGAMYNGVHVEKAERAGAKLDSAVVYKLETGDKRITAAVYKDTGADRVEGKYFVI : 283
WP_048252127.1    : IGAMYNGVHVEKAERAGAKLENAVVYKLETGDKRITAAIYKDSGADRVEGKYFVV : 283
WP_031400524.1    : IGAMYNGVHVEKAERAGAKLDSAVVYKLETGDKRITAAIYKDTGADRVEGKYFVI : 283
WP_010089726.1    : IGAMYNGVHVEKAERAGAKLENAVVHKLETGNKRITAALYKDTGADRVEGKYFVI : 281
WP_011354898.1    : IGAMYNGVHVEKAERAGAKLDSAVVYKLETGDKRITAAVYKDTGADRVEGKYFVI : 283
WP_034187894.1    : IGAMYNGVHVEKAERAGAKLDSAVVYKLETGDKRIVAAIYKDTGADRVEGKYFVV : 283
WP_017329146.1    : IGAMYNGVHVEKAERAGAKLENAVVYKLETGANKRITAAIYKDTGADRVEGKYFVI : 281
WP_045565070.1    : IGAMYNGVHVEKAERAGAKLENAVVHKLETGNKRITAAIYKDTGADRVEGKYFVI : 281
WP_010804580.1    : IGAMYNAVHVEKAERAGAKLENAVVYPLETANKRITAAVYKDTGAERVEGKYFVV : 283
WP_042588018.1    : IGAMYNGVHVEKAERAGAKLENAVVHKLETGNKRITAAIYKDAGADRVEGKYFVI : 281
WP_038746878.1    : IGAMYNGVHVEKAERAGAKLVENAVVHKLEVGQKKIVAALYKDPKGVERVEGKYFVL : 281
WP_010118596.1    : IGAMYNGVHVEKAERAGAKLENAVVHKLEVGQKKIVAALYKDPKGVERVEGKYFVL : 281
WP_010108853.1    : IGAMYNGVHVEKAERAGAKLENAVVHKLEVGQKKIVAALYKDPKGVERVEGKYFVL : 281
ZP_02370914       : IGAMYNGVHVEKAERAGAKLENAVVHKLEVGQKKIVAALYKDPKGAERVEGKYFVL : 281
WP_045602806.1    : IGAMYNGVHVEKAERAGAKLENAVVHKLEVGQKKIVAALYKDPKGAERVEGKYFVL : 281
WP_004528231.1    : IGAMYNGVHVEKAERAGAKLENAVVHKLEVGQKKIVAALYKDPKGVERVEGKYFVL : 281
WP_009897186.1    : IGAMYNGVHVEKAERAGAKLENAVVHKLEVGQKKIVAALYKDPKGAERVEGKYFVL : 281
WP_038763142.1    : IGAMYNGVHVEKAERAGAKLENAVVHKLEVGQKKIVAAPYKDPKGVERVEGKYFVL : 281
WP_038781432.1    : IGAMYNGVHVEKAERAGAKLENAVVHKLEVGQKKIVAARYKDPKGVERVEGKYFVL : 281
WP_038778573.1    : IGAMYNGVHVEKAERAGAKLENAVVHKLEVGQKKIVAARYKDPKGVERVEGKYFVL : 281
WP_038779482.1    : IGAMYNGVHVEKAERAGAKLENAVVHKLEVGQKKIVAARYKDPKGVERVEGKYFVL : 281
WP_004198666.1    : IGAMYNGVHVEKAERAGAKLENAVVHKLEVGQKKIVAARYKDPKGVERVEGKYFVL : 281
WP_041195444.1    : IGAMYNGVHVEKAERAGAKLENAVVHKLEVGQKKIVAAPYKDPKGVERVEGKYFVL : 281
WP_044490678.1    : IGAMYNGVHVEKAERAGAKLENAVVHKLEVGQKKIVAARYKDPKGVERVEGKYFVL : 281
WP_041189202.1    : IGAMYNGVHVEKAERAGAKLENAVVHKLEVGQKKIVAARYKDPKGVERVEGKYFVL : 281
WP_038789867.1    : IGAMYNGVHVEKAERAGAKLENAVVHKLEVGQKKIVAARYKDPKGVERVEGKYFVL : 281
WP_041198446.1    : IGAMYNGVHVEKAERAGAKLENAVVHKLEVGQKKIVAARYKDPKGVERVEGKYFVL : 281
KGT02773.1        : IGAMYNGVHVEKAERAGAKLENAVVHKLEVGQKKIVAAPYKDPKGVERVEGKYFVL : 281
WP_015602981.1    : IGAMYNGVVHVEKAERAGAKLENAVVHKLEVGKKKIVAALYKDPKGVERVEGKYFVL : 281
WP_006027349.1    : IGAMYNGVVHVEKAERAGAKLENAVVHKLEVGRKKIVAALYKDPKGVERVEGKYFVL : 281
WP_027778581.1    : IGAMYNGVHVEKAERAGARLANAVVYKLEVTDKRIAAALYRDAQGNERVEGKYFVL : 284
```

[Sequence alignment figure showing multiple protein sequences aligned around positions 380, 400, and 420. The sequences are identified by accession numbers on the left and end lengths on the right.]

| Label | Sequence region | Length |
|---|---|---|
| Sequence3 | SLIGRDGFFRATEAKKIHLSNLSPIDQETQKIFKA-QKLMKFDELDAGIRDKAARFVE | 402 |
| WP_006396898.1 | SLIGRDGFFRATEAKKIHLSNLSRIDQETQKIFKA-QKLMKFDELDAGIRDKAARFVQ | 402 |
| WP_035974223.1 | SLIGRDGFFRATEAKKIHLSNLSRVDQETQKIFKA-QKLMKFEELDAGIRDKARFVQ | 402 |
| EGD03130.1 | SLIGRDGFFRATEAKKIHLSNMSRINQETQKIFKA-QKLMKFADLDAGIRDKAARFVQ | 402 |
| WP_040131619.1 | SLIGRDGFFRATEAKKIHLSNMSRINQETQKIFKA-QKLMKFADLDAGIRDKAARFVQ | 402 |
| WP_040140036.1 | SLIGRDGFFRATEAKKIHLSNMSPINQETQKIFKA-QKLMKFEELDAGIRDKAARFVQ | 402 |
| WP_034204694.1 | SLIGRDGFFRATEAKKIHLSNMSRINQETQKIFKA-QKLMKHELDAGIRDKAARFVQ | 402 |
| WP_044843287.1 | SLIGRDGFFRATEAKKIHLSNMSRINQETQKIFKA-QKLMKADLDAGIRDKAARFVQ | 402 |
| WP_023476482.1 | SLIGRDGFFRATEAKKIHLSNMSRINQETQKIFKA-QKLMKHDELDAGIRDKAARFVQ | 402 |
| WP_027780833.1 | SLIGRDGFFRATEAKKIHLSNMSRINQETQKIFKA-QKLMKHELDAGIRDKAARFVQ | 402 |
| WP_011658979.1 | SLIGRDGFFRATEAKKIHLSNMSPINQETQKIFKA-QKLMKSDELDAGIRDKAARFVQ | 402 |
| WP_050012791.1 | SLIGRDGFFRATEAKKIHLSNMSRINQETQKIFKA-QKLMKHELDAGIRDKAARFVQ | 402 |
| WP_011547562.1 | SLIGRDGFFRATEAKKIHLSNMSRINQETQKIFKA-QKLMKHDELDAGIRDKAARFVQ | 402 |
| WP_034202233.1 | SLIGRDGFFRATEAKKIHLSNMSRINQETQKIFKA-QKLMKHELDAGIRDKAARFVQ | 402 |
| WP_011349244.1 | SLIGRDGFFRANEAKKIHLSNMSRINQETQKIFKG-QKLMKFEELDAGIRDKAARFVQ | 402 |
| WP_034180249.1 | SLIGRDGFFRATEAKKIHLSNMSRINQETQKIFKG-QKLMKFEELDAGIRDKAARFVQ | 402 |
| WP_006752014.1 | SLIGRDGFFRATEAKKIHLSNMSRINQETQKIFKA-QKLMKSDELDAGIRDKAARFVQ | 402 |
| WP_047903069.1 | SLIGRDGFFRATEAKKIHLSNMSRINQETQKIFKG-QKLMKFEELDAGIRDKAARFVQ | 402 |
| YP_002234347 | SLIGRDGFFRATEAKKIHLSNMSRINQETQKIFKA-QKLMKHELDAGIRDKAARFVQ | 402 |
| WP_039320756.1 | SLIGRDGFFRATEAKKIHLSNMSRINQETQKIFKA-QKLMKAGELDAGIRDKAARFVQ | 402 |
| WP_011882360.1 | SLIGRDGFFRATEAKKIHLSNMSRINQETQKIFKA-QKLMKFAELDAGIRDKAARFVQ | 402 |
| WP_021162033.1 | SLIGRDGFFRATEAKKIHLSNMSRINQETQKIFKA-QKLMKFEELDAGIRDKAARFVQ | 402 |
| WP_014724779.1 | SLIGRDGFFRATEAKKIHLSNMSRINQETQKIFKA-QKLMKFEALDSGIRDKAARFVQ | 402 |
| WP_012366205.1 | SLIGRDGFFRATEAKKIHLSNMSRINQETQKIFKA-QKLMKSGELDAGIRDKAARFVQ | 402 |
| WP_046548034.1 | SLIGRDGFFRATEAKKIHLSNMSRINQETQKIFKG-QKLMKFEELDAGIRDKAARFVQ | 402 |
| WP_039351161.1 | SLIGRDGFFRATEAKKIHLSNMSRINQETQKIFKG-QKLMKFEELDAGIRDKAARFVQ | 402 |
| WP_027791851.1 | SLIGRDGFFRATEAKKIHLSNMSRINQETQKIFKA-QKLMKFEELDAGIRDKAARFVQ | 402 |
| WP_047849808.1 | SLIGRDGFFRATEAKKIHLSNMSRINQETQKIFKG-QKLMKFEELDTGIRDKAARFVQ | 402 |
| WP_043184375.1 | SLIGRDGFFRATEAKKIHLSNMSRINQETQKIFKG-QKLMKFEELDAGIRDKAARFVQ | 402 |
| WP_014899066.1 | SLIGRDGFFRATEAKKIHLSNMSRINQETQKIFKA-QKLMKSGELDAGIRDKAARFVQ | 402 |
| WP_048252127.1 | SLIGRDGFFRATEAKKIHLSNMSRINQETQKILKG-QKLMKFEELDAGIRDKAARFVE | 402 |
| WP_031400524.1 | SLIGRDGFFRATEAKKIHLSNMSRINQETQKIFKG-QKLMKGELDAGIRDKAARFVQ | 402 |
| WP_010089726.1 | SLIGRDGFFRAEAGKKIHLSNISRVDQETQKIFKA-QLLHDELDAGIRDKAARFVQ | 400 |
| WP_011354898.1 | SLIGRDGFFRANEAKKIHLSNMSRINQETQKIFKG-QKLMKFEELDAGIRDKAARFVQ | 402 |
| WP_034187894.1 | SLIGRDGFFRATEAKKIHLSNMSRINQETQKIFKA-QKLMKFAELDAGIRDKAARFVQ | 402 |
| WP_017329146.1 | SLIGRDGFFRAEAGKKIHLSNISRVDQETQKIFKA-QLLHDELDAGIRDKAARFVQ | 400 |
| WP_045565070.1 | SLIGRDGFFRATEAKKIHLSNISPVDQETQKIFKA-QLLKHDELDAGIRDKAARFVQ | 400 |
| WP_010804580.1 | SLIGYRDGFFRATEAKKIHLSNMSRINQETEKLKG-QTLMKSELDRIRDKAARFVQ | 402 |
| WP_042588018.1 | SLIGRDGFFRATEAKKIHLSNISRVDQETQKIFKA-QLLRHDELDAGIRDKAARFVQ | 400 |
| WP_038746678.1 | SLIGRDGFFRATEAKKIHLSNLSRIDQETQKIFKA-QLLKFAELDAGIRDKAARFVQ | 400 |
| WP_010118596.1 | SLIGRDGAFRATEAKKIHLSNLSPIDQETQKIFKA-QKLMKFAELDAGIRDKAARFVQ | 400 |
| WP_010108853.1 | SLIGRDGAFRATEAKKIHLSNLSPIDQETQKIFKA-QKLMKFAELDAGIRDKAARFVQ | 400 |
| ZP_02370914 | SLIGRDGFFRATEAKKIHLSNLSRIDQETQKIFKA-QLLKFAELDAGIRDKAARFVQ | 400 |
| WP_045602806.1 | SLIGRDGFFRATEAKKIHLSNLSRIDQETQKIFKA-QLLKFAELDAGIRDKAARFVQ | 400 |
| WP_004528231.1 | SLIGRDGAFRATEAKKIHLSNLSRVDQETQKIFKA-QLLKFAELDAGIRDKAARFVQ | 400 |
| WP_009697186.1 | SLIGRDGFFRATEAKKIHLSNLSRIDQETQKIFKA-QLLKFAELDAGIRDKAARFVQ | 400 |
| WP_038763142.1 | SLIGRDGAFRATEAKKIHLSNLSPVDQETQKIFKA-QLLKFAELDAGIRDKAARFVQ | 400 |
| WP_038781432.1 | SLIGRDGAFRATEAKKIHLSNLSPVDQETQKIFKA-QLLKFAELDAGIRDKAARFVQ | 400 |
| WP_038778573.1 | SLIGRDGAFRATEAKKIHLSNLSRVDQETQKIFKA-QLLKFAELDAGIRDKAARFVQ | 400 |
| WP_038779482.1 | SLIGRDGAFRATEAKKIHLSNLSRVDQETQKIFKA-QLLKFAELDAGIRDKAARFVQ | 400 |
| WP_004198666.1 | SLIGRDGAFRATEAKKIHLSNLSRVDQETQKIFKT-QLLKFAELDAGIRDKAARFVQ | 400 |
| WP_041195444.1 | SLIGRDGAFRATEAKKIHLSNLSRVDQETQKIFKA-QLLKFAELDAGIRDKAARFVQ | 400 |
| WP_044490678.1 | SLIGRDGAFRATEAKKIHLSNLSRVDQETQKIFKA-QLLKFAELDAGIRDKAARFVQ | 400 |
| WP_041189202.1 | SLIGRDGAFRATEAKKIHLSNLSRVDQETQKIFKA-CLLKFAELDAGIRDKAARFVQ | 400 |
| WP_038789867.1 | SLIGRDGAFRATEAKKIHLSNLSRVDQETQKIFKT-QLLKFAELDAGIRDKAARFVQ | 400 |
| WP_041198446.1 | SLIGRDGAFRATEAKKIHLSNLSRVDQETQKIFKT-QLLKFAELDAGIRDKAARFVQ | 400 |
| KGT02773.1 | SLIGRDGAFRATEAKKIHLSNLSRVDQETQKIFKA-CLLKFAELDAGIRDRAARFVQ | 400 |
| WP_015602981.1 | SLIGRDGAFRATEAKKIHLSNLSPIDQETQKIFKA-QLLKFAELDAGIRDRAARFVQ | 400 |
| WP_006027349.1 | SLIGRDGAFRATEAKKIHLSNLSRIDQETQKIFKA-QLLKFAELDAGIRDRAARFVQ | 400 |
| WP_027778581.1 | SLIGRDGAFRSTEAKKIHLSNLSRVDQETQKIFKQ-QLIKFAELDAGIRDKARFVE | 403 |

Fig. 1-8

```
                              *         440         *         460         *         480
Sequence3         : FDCFHEXLPQPENRIXPSKTXTDAXGIXRPEITYXIDDYVKRGAAHTREXYAXAAKVLGG : 462
WP_006396898.1    : FDCFHEXLPQPENRIXPSKTXTDAXGIXRPEITYXIDDYVKRGAAHTREXYAXAAKVLGG : 462
WP_035974223.1    : FDCFHEXLPQPENRIXPSKTXTDAXGIXRPEITYXIDDYVKRGAVHTREXYAXAAKVLGG : 462
EGD03130.1        : FDCFHEXLPQPENRIXPSKTXTDALGIXRPEITYXIDDYVKRGAVHTREXYAXAAKVLGG : 462
WP_040131619.1    : FDCFHEXLPQPENRIXPSKTXTDAXGIXRPEITYXIDDYVKRGAVHTREXYAXAAKVLGG : 462
WP_040140036.1    : FDCFHEXLPQPENRIXPSKTXTDAXGIXRPEITYXIDDYVKRGAVHTREXYAXAAKVLGG : 462
WP_034204694.1    : FDCFHEXLPQPENRIXPSKTXTDAXGIXRPEITYXIDDYVKRGAVHTREXYAXAAKVLGG : 462
WP_044843287.1    : FDCFHEXLPQPENRIXPSKTXTDAXGIXRPEITYXIDDYVKRGAVHTREXYAXAAQVLGG : 462
WP_023476482.1    : FDCFHEXLPQPENRIXPSKTXTDAXGIXRPEITYXIDDYVKRGAVHTREXYAXAAKVLGG : 462
WP_027780833.1    : FDCFHEXLPQPENRIXPSKTXTDAXGIXRPEITYXIDDYVKRGAVHTREXYAXAAKVLGG : 462
WP_011658979.1    : FDCFHEXLPQPENRIXPSKTXTDAXGIXRPEITYXIDDYVKRGAVHTREXYAXAAKVLGG : 462
WP_050012791.1    : FDCFHEXLPQPENRIXPSKTXTDAXGIXRPEITYXIDDYVKRGAVHTREXYAXAAKVLGG : 462
WP_011547562.1    : FDCFHEXLPQPENRIXPSKTXTDAXGIXRPEITYXIDDYVKRGAVHTREXYAXAAKVLGG : 462
WP_034202233.1    : FDCFHEXLPQPENRIXPSKTXTDAXGIXRPEITYXIDDYVKRGAVHTREXYAXAAKVLGG : 462
WP_011349244.1    : FDCFHEXLPQPENRIXPSKTXTDAVGIXRPEITYXIDDYVKRGAVHTREXYAXAAKVLGG : 462
WP_034180249.1    : FDCFHEXLPQPENRIXPSKTXTDAXGIXRPEITYXIDDYVKRGAVHTREXYAXAAKVLGG : 462
WP_006752014.1    : FDCFHEXLPQPENRIXPSKTXTDAXGIXRPEITYXIDDYVKRGAVHTREXYAXAAKVLGG : 462
WP_047903069.1    : FDCFHEXLPQPENRIXPSKTXTDAXGIXRPEITYXIDDYVKRGAVHTREXYAXAAKVLGG : 462
YP_002234347      : FDCFHEXLPQPENRIXPSKTXTDAXGIXRPEITYXIDDYVKRGAVHTREXYAXAAKVLGG : 462
WP_039320756.1    : FDCFHEXLPQPENRIXPSKTXTDAVGIXRPEITYXIDDYVKRGAVHTREXYAXAAKVLGG : 462
WP_011882360.1    : FDCFHEXLPQPENRIXPSKTXTDAXGIXRPEITYXIDDYVKRGAVHTREXYAXAAQVLGG : 462
WP_021162033.1    : FDCFHEXLPQPENRIXPSKTXTDAXGIXRPEITYXIDDYVKRGAVHTREXYAXAAKVLGG : 462
WP_014724779.1    : FDCFHEXLPQPENRIXPSKTXTDAXGIXRPEITYXIDDYVKRGAVHTREXYAXAAQVLGG : 462
WP_012366205.1    : FDCFHEXLPQPENRIXPSKTXTDAXGIXRPEITYXIDDYVKRGAVHTREXYAXAAKVLGG : 462
WP_046548034.1    : FDCFHEXLPQPENRIXPSKTXTDAXGIXRPEITYXIDDYVKRGAVHTREXYAXAAKVLGG : 462
WP_039351161.1    : FDCFHEXLPQPENRIXPSKTXTDAXGIXRPEITYXIDDYVKRGAVHTREXYAXAAKVLGG : 462
WP_027791851.1    : FDCFHEXLPQPENRIXPSKTXTDAVGIXRPEITYXIDDYVKRGAVHTREXYAXAAKVLGG : 462
WP_047849808.1    : FDCFHEXLPQPENRIXPSKTXTDAXGIXRPEITYXIDDYVKRGAVHTREXYAXAAKVLGG : 462
WP_043184375.1    : FDCFHEXLPQPENRIXPSKTXTDAXGIXRPEITYXIDDYVKRGAVHTREXYAXAAKVLGG : 462
WP_014899066.1    : FDCFHEXLPQPENRIXPSKTXTDAVGIXRPEITYXIDDYVKRGAVHTREXYAXAAKVLGG : 462
WP_046252127.1    : FDCFHEXLPQPENRIXPSKTXTDAXGIXRPEITYXIDDYVKRGAVHTREXYAXAAKVLGG : 462
WP_031400524.1    : FDCFHEXLPQPENRIXPSKTXTDAXGIXRPEITYXIDDYVKRGAVHTREXYAXAAKVLGG : 462
WP_010089726.1    : FDCFHEXLPQPENRIXPSKTXTDAXGIXRPEITYXIDDYVKRGAVHTREXYAXAAKVLGG : 460
WP_011354898.1    : FDCFHEXLPQPENRIXPSKTXTDAVGIXRPEITYXIDDYVKRGAVHTREXYAXAAKVLGG : 462
WP_034187894.1    : FDCFHEXLPQPENRIXPSKTXTDAXGIXRPEITYXIDDYVKRGAVHTREXYAXAAKVLGG : 462
WP_017329146.1    : FDCFHEXLPQPENRIXPSKTXTDAXGIXRPEITYXIDDYVKRGAVHTREXYAXAAQVLGG : 460
WP_045565070.1    : FDCFHEXLPQPENRIXPSKTXTDAXGIXRPEITYXIDDYVKRGAVHTREXYAXAAQVLGG : 460
WP_010804580.1    : FDCFHEMLPSPENRIXPSTTXTDAXGIXRPEITYXIDDYVKRGAAHTREIYAXAAKVLCG : 462
WP_042588018.1    : FDCFHEXLPQPENRIXPSKTXTDAXGIXRPEITYXIDDYVKRGAVHTREXYAXAAQVLGG : 460
WP_038746878.1    : FDCFHEXLPQPENRIXPSKTXTDAXGIXRPEITYXIDDYVKRGAVHTREXYAXAAKVLGG : 460
WP_010118596.1    : FDCFHEXLPQPENRIXPSKTXTDAXGIXRPEITYXIDDYVKRGAVHTREXYAXAAKVLGG : 460
WP_010108853.1    : FDCFHEXLPQPENRIXPSKTXTDAXGIXRPEITYXIDDYVKRGAVHTREXYAXAAKVLGG : 460
ZP_02370914       : FDCFHEXLPQPENRIXPSKTXTDAXGIXRPEITYXIDDYVKRGAAHTREXYASAAQVLGG : 460
WP_045602806.1    : FDCFHEXLPQPENRIXPSKTXTDAXGIXRPEITYXIDDYVKRGAAHTREXYASAAQVLGG : 460
WP_004528231.1    : FDCFHEXLPQPENRIXPSRTXTDAXGIXRPEITYXIDDYVKRGAAHTREXYASAAQVLGG : 460
WP_009897186.1    : FDCFHEXLPQPENRIXPSRTXTDAXGIXRPEITYXIDDYVKRGAAHTREXYASAAQVLGG : 460
WP_038763142.1    : FDCFHEXLPQPENRIXPSRTXTDAXGIXRPEITYXIDDYVKRGAAHTREXYAXAAQVLGG : 460
WP_038781432.1    : FDCFHEXLPQPENRIXPSRTXTDAXGIXRPEITYXIDDYVKRGAAHTREXYAXAAQVLGG : 460
WP_038778573.1    : FDCFHEXLPQPENRIMPSRTXTDAXGIXRPEITYXIDDYVKRGAAHTREXYAXAAQVLGG : 460
WP_038779482.1    : FDCFHEXLPQPENRIXPSRTXTDAXGIXRPEITYXIDDYVKRGAAHTREXYAXAAQVLGG : 460
WP_004198666.1    : FDCFHEXLPQPENRIXPSRTXTDAXGIXRPEITYXIDDYVKRGAAHTREXYAXAAQVLGG : 460
WP_041195444.1    : FDCFHEXLPQPENRIXPSRTXTDAXGIXRPEITYXIDDYVKRGAAHTREXYAXAAQVLGG : 460
WP_044490678.1    : FDCFHEXLPQPENRIXPSPTXTDAXGIXRPEITYXIDDYVKRGAAHTREXYAXAAQVLGG : 460
WP_041189202.1    : FDCFHEXLPQPENRIXPSRTXTDAXGIXRPEITYXIDDYVKRGAAHTREXYAXAAQVLGG : 460
WP_038789867.1    : FDCFHEXLPQPENRIXPSRTXTDAXGIXRPEITYXIDDYVKRGAAHTREXYAXAAQVLGG : 460
WP_041198446.1    : FDCFHEXLPQPENRIXPSRTXTDAXGIXRPEITYXIDDYVKRGAAHTREXYAXAAQVLGG : 460
KGT02773.1        : FDCFHEXLPQPENRIXPSRTXTDAXGIXRPEITYXIDDYVKRGAAHTREXYAXAAQVLGG : 460
WP_015602981.1    : FDCFHEXLPQPENRIXPSKTXTDALGIXRPEITYRIDDYVKRGAVHTREXYAXAAQVLGG : 460
WP_006027349.1    : FDCFHEXLPQPENRIXPSKTXTDALGIXRPEITYRIDDYVKRGAVHTREXYAXAAQVLGG : 460
WP_027778581.1    : FDCFHEXLPQPENRIXPSRTETDAXGIARPEITYRIDDYVKRGAAHTREXYANAAKVLGG : 463
```

```
Sequence3       : TIAALALPMSDTLKKEV--  : 539
WP_006396898.1  : TIAALALRMSDTLKKEV--  : 539
WP_035974223.1  : TIAALALPMSDTLKKEV--  : 539
EGD03130.1      : TIAALALPMSDTLKKEV--  : 539
WP_040131619.1  : TIAALALPMSDTLKKEV--  : 539
WP_040140036.1  : TIAALALPMSDTLKKEV--  : 539
WP_034204694.1  : TIAALALPMSDTLKKEV--  : 539
WP_044843287.1  : TIAALALPMSDTLKKEV--  : 539
WP_023476482.1  : TIAALALPMSDTLKKEV--  : 539
WP_027780833.1  : TIAALALPMSDTLKKEV--  : 539
WP_011658979.1  : TIAALALPMSDTLKKEV--  : 539
WP_050012791.1  : TIAALALPMSDTLKKEV--  : 539
WP_011547562.1  : TIAALALPMSDTLKKEV--  : 539
WP_034202233.1  : TIAALALPMSDTLKKEV--  : 539
WP_011349244.1  : TIAALALPMSDTLKKEV--  : 539
WP_034180249.1  : TIAALALPMSDTLKKEV--  : 539
WP_006752014.1  : TIAALALPMSDTLKKEV--  : 539
WP_047903069.1  : TIAALALPMSDTLKKEV--  : 539
YP_002234347    : TIAALALPMSDTLKKEV--  : 539
WP_039320756.1  : TIAALALPMSDTLKKEV--  : 539
WP_011882360.1  : TIAALALRISDTLKKEV--  : 539
WP_021162033.1  : TIAALALPMSDTLKKEV--  : 539
WP_014724779.1  : TIAALALRISDTLKKEV--  : 539
WP_012366205.1  : TIAALALPMSDTLKKEV--  : 539
WP_046548034.1  : TIAALALPMSDTLKKEV--  : 539
WP_039351161.1  : TIAALALPMSDTLKKEV--  : 539
WP_027791851.1  : TIAALALPMSDTLKKEV--  : 539
WP_047849808.1  : TIAALALPMSDTLKKEV--  : 539
WP_043184375.1  : TIAALALPMSDTLKKEV--  : 539
WP_014899066.1  : TIAALALPMSDTLKKEV--  : 539
WP_048252127.1  : TIAALALPMSDTLKKEV--  : 539
WP_031400524.1  : TIAALALPMSDTLKKEV--  : 539
WP_010089726.1  : TIAALALRMSDQLKKEV--  : 537
WP_011354898.1  : TIAALALRMSDTLKKEV--  : 539
WP_034187894.1  : TIAALALPMSDTLKKEV--  : 539
WP_017329146.1  : TIAALALRMSDQLKKEV--  : 537
WP_045565070.1  : TIAALALRISDQLKKEV--  : 537
WP_010804580.1  : TIAALALPMADTLKKEV--  : 539
WP_042588018.1  : TIAALALRISDQLKKEV--  : 537
WP_038746878.1  : TIAALALRISDQLKKEI--  : 537
WP_010118596.1  : TIAALALRISDQLKKEI--  : 537
WP_010108853.1  : TIAALALRISDQLKKEI--  : 537
ZP_02370914     : TIAALALRISDQLKKEI--  : 537
WP_045602806.1  : TIAALALRISDQLKKEF--  : 537
WP_004528231.1  : TIAALALRISDQLKKEI--  : 537
WP_009897186.1  : TIAALALRISDQLKKEI--  : 537
WP_038763142.1  : TIAALALRISDQLKREI--  : 537
WP_038781432.1  : TIAALALRISDQLKKEI--  : 537
WP_038778573.1  : TIAALALRISDQLKKEI--  : 537
WP_038779482.1  : TIAALALRISDQLKKEI--  : 537
WP_004198666.1  : TIAALALRISDQLKKEI--  : 537
WP_041195444.1  : TIAALALRISDQLKKEI--  : 537
WP_044490678.1  : TIAALALRISDQLKKEI--  : 537
WP_041189202.1  : TIAALALRISDQLKKEI--  : 537
WP_038789867.1  : TIAALALRISDQLKKEI--  : 537
WP_041198446.1  : TIAALALRISDQLKKEI--  : 537
KGT02773.1      : TIAALALRISDQLKKEI--  : 537
WP_015602981.1  : TIAALALRISDQLKKEI--  : 537
WP_006027349.1  : TIAALALRISDQLKKEI--  : 537
WP_027778581.1  : TIAALALRMADQLKKEV--  : 540
```

Fig. 2-1

```
                             *         20         *         40         *         60
Sequence3         : M  TD--------QK DV VGSGVAGA IVAH  AMAGKAVILLEAGPRMPRWEIVERFRN :  54
WP_020067867.1    : M  KQQS----EQ D V VGSGVAGA IVAH  AQAGK VILLEAGPRMPRWEIVERFRN :  56
WP_027798558.1    : M  KQPG----TQQ D V VGSGVAGA IVAH MAQACK VILLEAGPRMPRWEIVERFRN :  56
WP_017774216.1    : M  ---------LQ D V VGSGVAGA VAH  ALAGK VIMLEAGPR PRWEIVERFRN :  52
WP_035557405.1    : M  SHSQTQPK QQ D V VGSGVAGA IVAH MALAGR VILLEAGPRMPRWEIVERFRN :  60
WP_023194543.1    : M  AQNQ----AEQ D V VGSGVAGA IVAH  ALAGR VILLEAGPRMPRWEIVERFRN :  56
WP_048931828.1    : MP T--------QQ D V VGSGVAGA VAYE APAGK V MLEAGPR PRWEIVERFRN :  52
WP_039597686.1    : M  T--------QQTD V VGSGVAGA VAYE ARAGK V MLEAGPR PRWEIVERFRN :  52
WP_021195199.1    : MP T--------QQ D V VGSGVAGA VAYE ARAGK V MLEAGPR PRWEIVERFRN :  52
WP_027677929.1    : M  T--------QQ D V VGSGVAGA VAYE ARAGK V MLEAGPR PRWEIVERFRN :  52
WP_004629448.1    : M  T--------QQ D V VGSGVAGA VAYE ARAGK V MLEAGPR PRWEIVERFRN :  52
WP_024976326.1    : M  T--------QQ D V VGSGVAGA VAYE ARAGK V MLEAGPR PRWEIVERFRN :  52
WP_045204558.1    : M  T--------QQ D V VGSGVAGA VAYE ARAGK V MLEAGPR PRWEIVERFRN :  52
ZP_02007109       : M  QSEQ----TRQQ D V VGSGVAGA VAYE ARAGK V MLEAGPR PRWEIVERFRN :  56
WP_045786289.1    : MP TQQ-----AAQQ D V VGSGVAGA VAYE ARAGK V MLEAGPR PRWEIVERFRN :  56
WP_009238767.1    : M  QSEQ----TRQ D V VGSGVAGA VAYE ARAGK V MLEAGPR PRWEIVERFRN :  56
CBJ51936.1        : M  TR-----QAEQ D V VGSGVAGA VAYE ARAGK V ILLEAGPR PRWEIVERFRN :  55
WP_020749404.1    : M  TR-----QAEQ D V VGSGVAGA VAYE ARAGK V MLEAGPR PRWEIVERFRN :  55
WP_011000725.1    : M  ETR-----QAEQ D V VGSGVAGA VAYE ARAGK V MLEAGPR PRWEIVERFRN :  55
WP_028852718.1    : M  ETR-----QAEQ D V VGSGVAGA VAYE ARAGK V MLEAGPR PRWEIVERFRN :  55
WP_016727135.1    : M  ETR-----QAEQ D V VGSGVAGA VAYE ARAGK V MLEAGPR PRWEIVERFRN :  55
WP_019717688.1    : M  ETR-----QAEQ D V VGSGVAGA VAYE ARAGK V MLEAGPR PRWEIVERFRN :  55
WP_020831435.1    : M  ETR-----QAEQ D V VGSGVAGA VAYE ARAGK V MLEAGPR PRWEIVERFRN :  55
YP_002260434      : M  TR-----RADQ D V VGSGVAGA VAYE ARAGK V MLEAGPR PRWEIVERFRN :  55
WP_003279244.1    : M  TR-----RADQ D V VGSGVAGA VAYE ARAGK V MLEAGPR PRWEIVERFRN :  55
WP_039568928.1    : M  TR-----RADQ D V VGSGVAGA VAYE ARAGK V MLEAGPR PRWEIVERFRN :  55
WP_050138572.1    : M  ---------LK D V IGSGVAGG VAH  AMAGK V VLEAGPR SRWEIVENFRN :  52
WP_049608172.1    : M  ---------LK D V IGSGVAGG VAYE AMAGR V ILLEAGPR SRWEIVENFRN :  52
WP_050140675.1    : M  ---------LK D V IGSGVAGG VAH  AMAGK V VLEAGPR SRWEIVENFRN :  52
WP_050101384.1    : M  ---------LK D V IGSGVAGG VAH  AMAGK V VLEAGPR SRWEIVENFRN :  52
WP_050151802.1    : M  ---------LK D V IGSGVAGG VAH  AMAGK V ILLEAGPR SRWEIVENFRN :  52
WP_050107996.1    : M  ---------LK D V IGSGVAGG VAH  AMACK V YILEAGPR SRWEIVENFRN :  52
WP_050146890.1    : M  ---------LK D V IGSGVAGG VAH  AMAGK V ILLEAGPR SRWEIVENFRN :  52
WP_050135114.1    : M  ---------LK D V IGSGVAGG VAH  AMAGK V ILLEAGPR SRWEIVENFRN :  52
WP_050122940.1    : M  ---------LK D V IGSGVAGG VAH  AMAGR V ILLEAGPR SRWEIVENFRN :  52
WP_050113306.1    : M  ---------LK D V IGSGVAGG VAH  AMAGK V VLEAGPR SRWEIVENFRN :  52
WP_019081810.1    : M  ---------LK D V IGSGVAGG VAH  AMAGK V VLEAGPR SRWEIVENFRN :  52
CQH40496.1        : M  ---------LK D V IGSGVAGG VAH  AMAGK V VLEAGPR SRWEIVENFRN :  52
WP_050076365.1    : M  ---------LK D V IGSGVAGG VAH  AMAGK V VLEAGPR SRWEIVENFRN :  52
CFQ84255.1        : M  ---------LK D V IGSGVAGG VAH  AMAGK V VLEAGPR SRWEIVENFRN :  52
CFB68626.1        : M  ---------LK D V IGSGVAGG VAH  AMAGK V VLEAGPR SRWEIVENFRN :  52
WP_019083704.1    : M  ---------LK D V IGSGVAGG VAH  AMAGK V VLEAGPR SRWEIVENFRN :  52
WP_004391242.1    : M  ---------LK D VII GSGVAGG VAH  AMAGK V VLEAGPR SRWEIVENFRN :  52
WP_050130822.1    : M  ---------LK DV  IGSGVAGG VAH  AMAGK V VLEAGPR SRWEIVENFRN :  52
WP_048616917.1    : M  ---------LK D V IGSGVAGG VAH  AMAGK V VLEAGPR SRWEIVENFRN :  52
WP_050157528.1    : M  ---------LK D V IGSGVAGG VAH  AMAGK V VLEAGPR SRWEIVENFRN :  52
CNB97617.1        : M  ---------LK D V IGSGVAGG VAH  AMAGK V VLEAGPR SRWEIVENFRN :  52
CRE83670.1        : M  ---------LK D V IGSGVAGG VAH  AMAGK V VLEAGPR SRWEIVENFRN :  52
WP_033635282.1    : M  ---------LK D V IGSGVAGG VAH  AMAGK V VLEAGPR SRWEIVENFRN :  52
CQQ92408.1        : M  ---------LK D V IGSGVAGG VAH  AMAGK V VLEAGPR SRWEIVENFRN :  52
WP_049679386.1    : M  ---------LK D V IGSGVAGG VAH  AMAGK V VLEAGPR SRWEIVENFRN :  52
WP_049648565.1    : M  ---------LK D V IGSGVAGG VAH  AMAGK V VLEAGPR SRWEIVENFRN :  52
WP_050159872.1    : M  ---------LK D V IGSGVAGG VAH  AMAGK V VLEAGPR SRWEIVENFRN :  52
WP_050144494.1    : M  ---------LK D V IGSGVAGG VAH  AMACK V VLEAGPR SRWEIVENFRN :  52
CFR10819.1        : M  ---------LK DV  IGSGVAGG VAH  AMAGK V VLEAGPR SRWEIVENFRN :  52
WP_050299034.1    : M  ---------LK D V IGSGVAGG VAH  AMAGK V VLEAGPR SRWEIVENFRN :  52
WP_049610421.1    : M  ---------LK D V IGSGVAGG VAH  AMAGK V VLEAGPR SRWEIVENFRN :  52
WP_004877956.1    : M  ---------LK D V IGSGVAGG VAH  AMAGK V VLEAGPR SRWEIVENFRN :  52
WP_046050437.1    : M  ---------LK D V IGSGVAGG VAH  AMAGK V VLEAGPR SRWEIVENFRN :  52
CFR23261.1        : M  ---------LK DV IIGSGVAGG VAH  AMAGK V VLEAGPR SRWEIVENFRN :  52
```

Fig. 2-2

```
                           *        80         *       100         *       120
Sequence3         : QPDKMDFNAAYESSPWAPHPEYGP-PNDYVLKGEHKFNSQYIRAVGGTWHWAASAWRF : 113
WP_020067867.1    : QADKMDFNAAYPPSKWAPHPEYYP-PNYYVLKGEHKFNSQYIRAVGGTWHWAASAWRF : 115
WP_027798558.1    : QADKMDFNAAYPPSKWAPHPEYNP-PNYYVLKGEHKFNSQYIRAVGGTWHWAASAWRF : 115
WP_017774216.1    : QFDKMDFNAAYESSPWAPHPEYGP-PNYYVLKGEHKFNSQYIRAVGGTWHWAASAWRF : 111
WP_035557405.1    : QFDKSDNSAAYESSQWAPHPEYGP-PNYYVLKGEHKFNSQYIRAVGGTWHWAASAWRF : 119
WP_028194543.1    : QFDKSDNSAAYESSAWAPHPEYGP-PNYYVLKGEHKFNSQYIRAVGGTWHWAASAWRF : 115
WP_048931828.1    : QADKMDFNAAYPSSPWAPHPEYGP-PNYYVLKGEHKFNSQYIRAVGGTWHWAASTWRF : 111
WP_039597686.1    : QADKMDFNAAYPSSPWAPHPEYGP-PNYYVLKGEHKFNSQYIRAVGGTWHWAASTWRF : 111
WP_021195199.1    : QADKMDFNAAYPSSWAPHPEYGP-PNYYVLKGEHKFNSQYIRAVGGTWHWAASTWRF : 111
WP_027677929.1    : QADKMDFNAAYPSSPWAPHPEYGP-PNYYVLKGEHQFNSQYIRAVGGTWHWAASTWRF : 111
WP_004629448.1    : QADKMDFNAAYPSSPWAPHPEYGP-PNYYVLKGEHQFNSQYIRAVGGTWHWAASTWRF : 111
WP_024976326.1    : QADKMDFNAAYPSSPWAPHPEYGP-PNYYVLKGEHQFNSQYIRAVGGTWHWAASTWRF : 111
WP_045204558.1    : QADKMDFNAAYPSSPWAPHPEYGP-PNYYVLKGEHQFNSQYIRAVGGTWHWAASTWRF : 111
ZP_02007109       : QADKMDFNAAYPSSAWAPHPEYGP-PNYYVLKGEHQFNSQYIRAVGGTWHWAASTWRF : 115
WP_045786289.1    : QADKMDFNAAYESSMPWAPHPEYGP-PNYYVLKGEHQFNSQYIRAVGGTWHWAASTWRF : 115
WP_009238767.1    : QADKMDFNAAYPSSPWAPHPEYGP-PNYYVLKGEHQFNSQYIRAVGGTWHWAASTWRF : 115
CBJ51936.1        : QADKMDFNAAYPSSPWAPHPEYGP-PNYYVLKGEHPFSSQYIRAVGGTWHWAASTWRF : 114
WP_020749404.1    : QADKMDFNAAYPSSPWAPHPEYGP-DNYYMLKGEHRFSSQYIRAVGGTWHWAASTWRF : 114
WP_011000725.1    : QADKMDFNAAYPSSPWAPHPEYGP-DNYYVLKGEHKFSSQYIRAVGGTWHWAASTWRF : 114
WP_028852718.1    : QADKMDFNAAYPSSPWAPHPEYGP-DNYYVLKGEHKFSSQYIRAVGGTWHWAASTWRF : 114
WP_016727135.1    : QADKMDFNAAYPSSPWAPHPEYGP-DNYYVLKGEHKFSSQYIRAVGGTWHWAASTWRF : 114
WP_019717688.1    : QADKMDFNAAYPSSPWAPHPEYGP-DNYYVLKGEHKFSSQYIRAVGGTWHWAASTWRF : 114
WP_020831435.1    : QADKMDFNAAYPSSPWAPHPEYGP-DNYYVLKGEHKFSSQYIRAVGGTWHWAASTWRF : 114
YP_002260434      : QADKMDFNAAYPSSPWAPHPEYGPSPNDYVLKGEHKFSSQYIRAVGGTWHWAASTWRF : 115
WP_003279244.1    : QADKMDFNAAYPSSPWAPHPEYGPSPNDYVLKGEHKFSSQYIRAVGGTWHWAASTWRF : 115
WP_039568928.1    : QADKMDFNAAYPSSPWAPHPEYGPSPNDYVLKGEHKFSSQYIRAVGGTWHWAASTWRF : 115
WP_050138572.1    : QPDKSDNAAYPASSYAPHPESNP-NNYYQKGEHPYDVQYIRAVGGTWHWAASAWRF : 111
WP_049608172.1    : QPDKSDNAAYPASSYAPHPEANP-NNYYQKGEHPYDVQYIRAVGGTWHWAASAWRF : 111
WP_050140675.1    : QPDKSDNAAYPASSPYAPHPESNP-NNYYQKGEHPYDVQYIRAVGGTWHWAASAWRF : 111
WP_050101384.1    : QPDKSDNAAYPASSPYAPHPESNP-NNYYQKGEHPYDVQYIRAVGGTWHWAASAWRF : 111
WP_050151802.1    : QPDKSDNAAYPASSYAPHPESNP-NNYYQKGEHPYDVQYIRAVGGTWHWAASAWRF : 111
WP_050107996.1    : QPDKSDNAAYPASSYAPHPESNP-NNYYQKGEHPYDVQYIRAVGGTWHWAASAWRF : 111
WP_050146890.1    : QPDKSDNAAYPASSYAPHPESNP-NNYYQKGEHPYDVQYIRAVGGTWHWAASAWRF : 111
WP_050135114.1    : QPDKSDNAAYPASSYAPHPESNP-NNYYQKGEHPYDVQYIRAVGGTWHWAASAWRF : 111
WP_050122940.1    : QPDKSDNAAYPASSYAPHPESNP-NNYYQKGEHPYDVQYIRAVGGTWHWAASAWRF : 111
WP_050113306.1    : QPDKSDNAAYPASSYAPHPESNP-NNYYQKGEHPYDVQYIRAVGGTWHWAASAWRF : 111
WP_019081810.1    : QPDKSDNAAYPASSYAPHPESNP-NNYYQKGEHPYDVQYIRAVGGTWHWAASAWRF : 111
CQH40496.1        : QPDKSDNAAYPASSYAPHPESNP-NNYYQKGEHPYDVQYIRAVGGTWHWAASAWRF : 111
WP_050076365.1    : QPDKSDNAAYPASSYAPHPESNP-NNYYQKGEHPYDVQYIRAVGGTWHWAASAWRF : 111
CFQ84255.1        : QPDKSDNAAYPASSYAPHPESNP-NNYYQKGEHPYDVQYIRAVGGTWHWAASAWRF : 111
CFB68626.1        : QPDKSDNAAYPASSYAPHPESNP-NNYYQKGEHPYDVQYIRAVGGTWHWAASAWRF : 111
WP_019083704.1    : QPDKSDNAAYPASSYAPHPESNP-NNYYQKGEHPYDVQYIRAVGGTWHWAASAWRF : 111
WP_004391242.1    : QPDKSDNAAYPASSYAPHPESNP-NNYYQKGEHPYDVQYIRAVGGTWHWAASAWRF : 111
WP_050130822.1    : QPDKSDNAAYPASSYAPHPESNP-NNYYQKGEHPYDVQYIRAVGGTWHWAASAWRF : 111
WP_048616917.1    : QPDKSDNAAYPASSYAPHPESNP-NNYYQKGEHPYDVQYIRAVGGTWHWAASAWRF : 111
WP_050157528.1    : QPDKSDNAAYPASSYAPHPESNP-NNYYQKGEHPYDVQYIRAVGGTWHWAASAWRF : 111
CNB97617.1        : QPDKSDNAAYPASSYAPHPESNP-NNYYQKGEHPYDVQYIRAVGGTWHWAASAWRF : 111
CRE83670.1        : QPDKSDNAAYPASSYAPHPESNP-NNYYQKGEHPYDVQYIRAVGGTWHWAASAWRF : 111
WP_038635282.1    : QPDKSDNAAYPASSYAPHPESNP-NNYYQKGEHPYDVQYIRAVGGTWHWAASAWRF : 111
CQQ92408.1        : QPDKSDNAAYPASSYAPHPESNP-NNYYQKGEHPYDVQYIRAVGGTWHWAASAWRF : 111
WP_049679386.1    : QPDKSDNAAYPASSYAPHPESNP-NNYYQKGEHPYDVQYIRAVGGTWHWAASAWRF : 111
WP_049648565.1    : QPDKSDNAAYPASSYAPHPESNP-NNYYQKGEHPYDVQYIRAVGGTWHWAASAWRF : 111
WP_050159872.1    : QPDKSDNAAYPASSYAPHPESNP-NNYYQKGEHPYDVQYICAVGGTWHWAASAWRF : 111
WP_050144494.1    : QPDKSDNAAYPASSYAPHPESNP-NNYYQKGEHPYDVQYIRAVGGTWHWAASAWRF : 111
CFR10819.1        : QPDKSDNAAYPASSYAPHPESNP-NNYYQKGEHPYDVQYIRAVGGTWHWAASAWRF : 111
WP_050299034.1    : QPDKSDNAAYPASSYAPHPESNP-NNYYQKGEHPYDVQYIRAVGGTWHWAASAWRF : 111
WP_049610421.1    : QPDKSDNAAYPASSYAPHPESNP-NNYYQKGEHPYDVQYIRAVGGTWHWAASAWRF : 111
WP_004877956.1    : QPDKSDNAAYPASSYAPHPESNP-NNYYQKGEHPYDVQYIRAVGGTWHWAASAWRF : 111
WP_046050437.1    : QPDKSDNAAYPASSYAPHPESNP-NNYYQKGEHPYDVQYIRAVGGTWHWAASAWRF : 111
CFR23261.1        : QPDKSDNAAYPASSYAPHPESNP-NNYYQKGEHPYDVQYIRAVGGTWHWAASAWRF : 111
```

Fig. 2-3

```
                          *        140         *        160         *        180
Sequence3       : IPNDFKMSVYGVGRWPLQYDDKEPYYQRAEERLGVWCFGPEEDLYSPPKQPYPNP---P : 171
WP_020067867.1  : MPNDFRMKVYGVGRWPMQYEEKEPYYQRAEERLGVWGP-TREELGSPREQPYPR----P : 172
WP_027798558.1  : MPNDFRMKVYGVGRWPMEYEEKEPYYQRAEERLGVWGP-AREELGSPREQPYPR----P : 172
WP_017774216.1  : IPNDFKMNVVGIARWPLQYDDVEPWYYRAEQELGVWGP-NREDLYSPRKAPYPR----P : 168
WP_035557405.1  : MPNDFHMKVYGVGRWPMEYDEKEPYYQRAEERLGVWGP-TREELGSPREQPYPR----P : 176
WP_028194543.1  : MPNDFRMKTYGVGRWPMDYEEKEPYYQRAEERLGVWGP-TREELGSPREQPYPR----P : 172
WP_048931828.1  : IPNDFKRSVYGIARWPLQYSDKERYYGRAEEALGVWGP-NREDLGSPREQPYPNT---P : 168
WP_039597686.1  : MPNDFKRSVYGIARWPLQYGDKERYYGRAEEALGVWGP-NREDLGSPREQPYPNT---P : 168
WP_021195199.1  : IPNDFKRSVYGIARWPLQYSDKERYYGRAEEALGVWGP-NREDLGSPREQPYPNT---P : 168
WP_027677929.1  : IPNDFKRSVYGIARWPLQYQDKERYYGLAEEALGVWGP-NREDLGSPREQPYPR----P : 168
WP_004629448.1  : IPNDFKRSVYGIARWPLQYQDKERYYGRAEEALGVWGP-NREDLGSPREQPYPR----P : 168
WP_024976326.1  : IPNDFKRSVYGIARWPLQYQDKERYYGLAEEALGVWGP-NREDLGSPREQPYPR----P : 168
WP_045204558.1  : IPNDFKRSVYGIARWPLQYQDKERYYCLAEEALGVWGP-NREDLGSPREQPYPT----P : 168
ZP_02007109     : IPNDFKRSVYGIARWPLQYQDKERYYGLAEEALGVWGP-NREDLGSPREQPYPNT---P : 172
WP_045786289.1  : IPNDFKRSVYGIARWPLQYDDKERYYGLAEEAAGVWGP-NREDLGSPREQPYPR----P : 172
WP_009238767.1  : IPNDFKRSVYGIARWPLQYQDKERYYGLAEEALGVWGP-NREDLGSPREQPYPNT---P : 172
CBJ51936.1      : IPNDFKRSVYGIARWPLQYDDKERYYGQAEAALGVWGP-NREDLGSPRERPYPR----P : 171
WP_020749404.1  : IPNDFKRSVYGIARWPLQYDDKERYYCRAEAALGVWGP-NREALGSPREQPYPR----P : 171
WP_011000725.1  : IPNDFKRSVYGIARWPLQYDDKERYYGRAEAALGVWGP-NREDLGSPREQPYPR----P : 171
WP_028852718.1  : IPNDFKRSVYGIARWPLQYDDKERYYGRAEAALGVWGP-NREDLGSPREQPYPR----P : 171
WP_016727135.1  : IPNDFKRSVYGIARWPLQYDDKERYYGRAEAALGVWGP-NREDLGSPREQPYPR----P : 171
WP_019717688.1  : IPNDFKRSVYGIARWPLQYDDKERYYGRAEAALGVWGP-NREDLGSPREQPYPR----P : 171
WP_020831435.1  : IPNDFKRSVYGIARWPLQYDDKERYYGRAEAALGVWGP-NREDLGSPREQPYPR----P : 171
YP_002260434    : IPNDFKRSVYGIARWPLQYDDKERDYGRAEAALGVWGP-NREDLGSPREQPYPR----P : 172
WP_003279244.1  : IPNDFKRSVYGIARWPLQYDDKERDYGRAEAALGVWGP-NREDLGSPREQPYPNVPLP : 174
WP_039568928.1  : IPNDFKRSVYGIARWPLQYDDKERDYGRAEAALGVWGP-NREDLGSPREQPYPNV---P : 172
WP_050138572.1  : IPNDFKKIIYGVGRNWPFDYAAEKWYLRAEQRLGVWGP-SREDLGSPREAPYPR----P : 168
WP_049608172.1  : IPNDFKKTLYGVGRNWPFDYATEKWYFRAEQRLGVWGP-SREDLGSPREEPYPRV---P : 168
WP_050140675.1  : IPNDFKKVVGVGRPWPFEYAAEKWYFRAEQRLGVWGP-SREDLGSPREEPYPR----P : 168
WP_050101384.1  : IPNDFKKVVGVGRPWPFEYAAEKWYFRAEQRLGVWGP-SREDLGSPREEPYPR----P : 168
WP_050151802.1  : IPNDFKKVVGVGRPWPFEYAAEKWYLRAEQRLGVWGP-SREDLGSPREEPYPR----P : 168
WP_050107996.1  : IPNDFKKVVGVGRPWPFEYAAEKWYFRAEQRLGVWGP-SREDLGSPREEPYPR----P : 168
WP_050146890.1  : IPNDFKKVVGVGRPWPFEYAAEKWYLRAEQRLGVWGP-SREDLGSPREEPYPR----P : 168
WP_050135114.1  : IPNDFKKVVGVGRPWPFEYAAEKWYFRAEQRLGVWGP-SREDLGSPREEPYPR----P : 168
WP_050122940.1  : IPNDFKKVVGVGPWPFEYAAEKWYLRAEQRLGVWGP-SREDLGSPREEPYPR----P : 168
WP_050113306.1  : IPNDFKKIYGVGPWPFDYAAEKWYLRAEQRLGVWGP-SREDLGSPREAPYPR----P : 168
WP_019081810.1  : IPNDFKKIYGVGPWPFDYAAEKWYLRAEQRLGVWGP-SREDLGSPREAPYPR----P : 168
CQH40496.1      : IPNDFKKIYGVGPWPFDYAAEKWYLRAEQRLGVWGP-SREDLGSPREAPYPR----P : 168
WP_050076365.1  : IPNDFKKIYGVGPWPFDYAAEKWYLRAEQRLGVWGP-SREDLGSPREAPYPR----P : 168
CFQ84255.1      : IPNDFKKIYGVGPWPFDYAAEKWYLRAEQRLGVWGP-SREDLGSPREAPYPR----P : 168
CFB68626.1      : IPNDFKKIYGVGPWPFDYAAEKWYLRAEQRLGVWGP-SREDLGSPREAPYPR----P : 168
WP_019083704.1  : IPNDFKKIYGVGPWPFDYAAEKWYLRAEQRLGVWGP-SREDLGSPREAPYPR----P : 168
WP_004391242.1  : IPNDFKKIYGVGPWPFDYATEKWYLRAEQRLGVWGP-SREDLGSPREAPYPR----P : 168
WP_050130822.1  : IPNDFKKVYGVGPWPFEYAAEKWYFRAEQRLGVWGP-SREDLGSPREEPYPR----P : 168
WP_048611917.1  : IPNDFKKVYGVGPWPFEYAAEKWYFRAEQRLGVWGP-SREDLGSPREEPYPR----P : 168
WP_050157529.1  : IPNDFKKIYGVGPWPFDYAAEKWYLRAEQRLGVWGP-SREDLGSPREAPYPR----P : 168
CNB97617.1      : IPNDFKKIYGVGPWPFDYAAEKWYLRAEQRLGVWGP-SREDLGSPREAPYPR----P : 168
CRE83670.1      : IPNDFKKIYGVGPWPFDYAAEKWYLRAEQRLGVWGP-SREDLGSPREAPYPR----P : 168
WP_038635282.1  : IPNDFKKIYGVGPWPFDYAAEKWYLRAEQRLGVWGP-SREDLGSPREAPYPR----P : 168
CQQ92408.1      : IPNDFKKIYGVGPWPFDYAVEKWYLRAEQRLGVWGP-SREDLGSPREAPYPR----P : 168
WP_049679386.1  : IPNDFKKLYGVGRWPFEYAAEKWYLRAEQRLGVWGP-SREDLGSPREEPYPR----P : 168
WP_049648565.1  : IPNDFKKLYGVGRWPFEYAAEKWYLRAEQRLGVWGP-SREDLGSPREEPYPR----P : 168
WP_050159872.1  : IPNDFKKIYGVGPWPFEYAAEKWYLRAEQRLGVWGP-SREDLGSPREAPYPR----P : 168
WP_050144494.1  : IPNDFKKIYGVGPWPFEYAAEKWYFRAEQRLGVWGP-SREDLGSPREEPYPR----P : 168
CFR10819.1      : IPNDFKKVYGVGRWPFEYAAEKWYFRAEQRLGVWGP-SREDLGSPREEPYPR----P : 168
WP_050299034.1  : IPNDFKKLYGVGRWPFEYAAEKWYLRAEQRLGVWGP-SREDLGSPREEPYPR----P : 168
WP_049610421.1  : IPNDFKKLYGVGRWPFEYAAEKWYLRAEQRLGVWGP-SREDLGSPREEPYPR----P : 168
WP_004877956.1  : IPNDFKKLYGVGRWPFEYAAEKWYLRAEQRLGVWGP-SREDLGSPREEPYPR----P : 168
WP_046050437.1  : IPNDFKKIYGVGPWPFDYAAEKWYLRAEQRLGVWGP-SREDLGSPREAPYPR----P : 168
CFR23261.1      : IPNDFKKIYGVGPWPFDYATEKWYLRAEQRLGVWGP-SREDLGSPREAPYPR----P : 168
```

Fig. 2-4

```
                             *         200         *         220         *         240
Sequence3        : LPLSFRQTLKTALNNYDP--------KRHVVTEPVARNSSPYEGRPLCCGNNKCMPICP : 223
WP_020067867.1   : LPLSYRQTLKSKLNAFDS--------RYHVVTEPVARNSSPYEGRPLCCGNNKCMPICP : 224
WP_027798558.1   : LPVSYRQTLKTKLNAFDS--------RYHVVTEPVARNSSPYEGRPLCCGNNKCMPICP : 224
WP_017774216.1   : LPLSYRAILKSKLNAYDA--------AYHVVTEPVARNSVPYEGRPLCCGNNKCMPICP : 220
WP_035557405.1   : LPLSYRQILKGKLNAFDS--------RYHVVTEPVARNSSPYEGRPLCCGNNKCMPICP : 226
WP_028194543.1   : LPLSYRQTLKSKLNAFDS--------GYHVVTEPVARNSSPYEGRPLCCGNNKCMPICP : 224
WP_048931828.1   : LPLSFRERTLKEALNGYDP--------DRHVVTEPVARNSSPYEGRPLCCGNNKCMPICP : 220
WP_039597686.1   : LPLSFRERTLKQALNGYDP--------DRHVVTEPVARNSSPYEGRPLCCGNNKCMPICP : 220
WP_021195199.1   : LPLSFRERTLKEALNGYDP--------DRHVVTEPVARNSSPYEGRPLCCGNNKCMPICP : 220
WP_027677929.1   : LPLSFSERTLKDALNANDA--------SRHVVTEPVARNSSPYEGRPLCCGNNKCMPICP : 220
WP_004629448.1   : LPLSFSERTLKDALNANDA--------SLHVVTEPVARNSSPYEGRPLCCGNNKCMPICP : 220
WP_024976326.1   : PPLSFRERTLKEALNANDA--------SRHVVTEPVARNSSPYEGRPLCCGNNKCMPICP : 220
WP_045204558.1   : LPLSFRERTLKEALNANDA--------SRHVVTEPVARNSSPYEGRPLCCGNNKCMPICP : 220
ZP_02007109      : LPLSFRERTLKEALNANDA--------SRHVVTEPVARNSSPYEGRPLCCGNNKCMPICP : 224
WP_045786289.1   : LPLSFRERTLKEALNANDP--------SYHVVTEPVARNSSPYEGRPLCCGNNKCMPICP : 224
WP_009238767.1   : LPLSFSERTLKDALNANDA--------SRHVVTEPVARNSSPYEGRPLCCGNNKCMPICP : 224
CBJ51936.1       : LPLSFRERTLKEALNANDP--------ARHVVTEPVARNSSPYEGRPLCCGNNKCMPICP : 223
WP_020749404.1   : LPLSFRERTLKDALNANDP--------ALRVVTEPVARNSSPYEGRPLCCGNNKCMPICP : 223
WP_011000725.1   : LPLSFREPTVKDALNANDP--------ALRVVTEPVARNSSPYEGRPLCCGNNKCMPICP : 223
WP_028852718.1   : LPLSFRERTVKDALNANDP--------ALRVVTEPVARNSSPYEGRPLCCGNNKCMPICP : 223
WP_016727135.1   : LPLSFRERTLKDALNANDP--------ALRVVTEPVARNSSPYEGRPLCCGNNKCMPICP : 223
WP_019717688.1   : LPLSFREVTVKDALNANDP--------ALRVVTEPVARNSSPYEGRPLCCGNNKCMPICP : 223
WP_020831435.1   : LPLSFRERTLKDALNANDP--------ALRVVTEPVARNSSPYEGRPLCCGNNKCMPICP : 223
YP_002260434     : LPLSFRERTLKEALNANDP--------ARHVVTEPVARNSSPYEGRPLCCGNNKCMPICP : 224
WP_003279244.1   : LPLSFRERTLKEALNANDP--------ARHVVTEPVARNSSPYEGRPLCCGNNKCMPICP : 226
WP_039568928.1   : LPLSFRERTLKEALNANDP--------ARHVVTEPVARNSSPYEGRPICCGNNKCMPICP : 224
WP_050138572.1   : LPLSWRQRLKTVLNSSTFNGS-----RRDVVTEPVARNSSPYEGRPLCCGNNKCMPICP : 223
WP_049608172.1   : LPLSWRQRLKTVLNSSFTGSGPNDAHNVVTEPVARNSSPYEGRPLCCGNNKCMPICP : 228
WP_050140675.1   : LPLSWRQRLKTVLNSNFNGS-----PRHVVTEPVARNSSPYEGRPLCCGNNKCMPICP : 223
WP_050101384.1   : LPLSWRQRLKTVLNSHFNGS-----PRHVVTEPVARNSSPYEGRPLCCGNNKCMPICP : 223
WP_050151302.1   : LPLSWRQRLKTVLNSSFNGS-----DRNVVTEPVARNSSPYEGRPLCCGNNKCMPICP : 223
WP_050107996.1   : LPLSWRQRLKTVLNSSFNGS-----DRNVVTEPVARNSSPYEGRPLCCGNNKCMPICP : 223
WP_050146890.1   : LPLSWRQRLKTVLNSSFNGS-----DRNVVTEPVARNSSPYEGRPLCCGNNKCMPICP : 223
WP_050135114.1   : LPLSWRQRLKTVLNSSFNGS-----DRNVVTEPVARNSSPYEGRPLCCGNNKCMPICP : 223
WP_050122940.1   : LPLSWRQRLKTVLNSSFNGS-----DRNVVTEPVARNSSPYEGRPLCCGNNKCMPICP : 223
WP_050113306.1   : LPLSWRQRLKTVLNSTFNGS-----NRDVVTEPVARNSSPYEGRPLCCGNNKCMPICP : 223
WP_019081810.1   : LPLSWRQRLKTVLNSTFNGS-----KRDVVTEPVARNSSPYEGRPLCCGNNKCMPICP : 223
CQH40496.1       : LPLSWRQRLKTVLNSTFNGS-----KRDVVTEPVARNSSPYEGRPLCCGNNKCMPICP : 223
WP_050076365.1   : LPLSWRQRLKTVLNSTFNGS-----KRDVVTEPVARNSSPYEGRPLCCGNNKCMPICP : 223
CFQ84255.1       : LPLSWRQRLKTVLNSTFNGS-----KRDVVTEPVARNSSPYEGRPLCCGNNKCMPICP : 223
CFB68626.1       : LPLSWRQRLKTVLNSTFNGS-----KRDVVTEPVARNSSPYEGRPLCCGNNKCMPICP : 223
WP_019083704.1   : LPLSWRQRLKTVLNSTFNGS-----KRDVVTEPVARNSSPYEGRPLCCGNNKCMPICP : 223
WP_004391242.1   : LPLSWRQRLKTVLNSTFNGS-----HRDVVTEPVARNSSPYEGRPLCCGNNKCMPICP : 223
WP_050130822.1   : LPLSWRQRLKTVLNSSFNGS------DRNVVTEPVARNSSPYEGRPLCCGNNKCMPICP : 223
WP_048616917.1   : LPLSWRQRLKTVLNSNFNGSGFSDAHYNVVTEPVARNSSPYEGRPLCCGNNKCMPICP : 228
WP_050157528.1   : LPLSWRQRLKTVLNSTFNGS-----KRDVVTEPVARNSSPYEGRPLCCGNNKCMPICP : 223
CNB97617.1       : LPLSWRQRLKTVLNSTFNGS-----KRDVVTEPVARNSSPYEGRPLCCGNNKCMPICP : 223
CRE83670.1       : LPLSWRQRLKTVLNSTFNGS-----KRDVVTEPVARNSSPYEGRPLCCGNNKCMPICP : 223
WP_038635282.1   : LPLSWRQRLKTVLNSTFNGS-----RRDVVTEPVARNSSPYEGRPLCCGNNKCMPICP : 223
CQQ92408.1       : LPLSWRQRLKTVLNSTFNGS-----KRDVVTEPVARNSSPYEGRPLCCGNNKCMPICP : 223
WP_049679386.1   : LPLSWRQRLKTVLNSNRFTGSGFTDAHNVVTEPVARNSSPYEGRPLCCGNNKCMPICP : 228
WP_049648565.1   : LPLSWRQRLKTVLNSNRFTGSGFTDAHNVVTEPVARNSSPYEGRPLCCGNNKCMPICP : 228
WP_050159872.1   : LPLSWRQRLKTVLNSTFNGS-----KRDVVTEPVARNSSPYEGRPLCCGNNKCMPICP : 223
WP_050144494.1   : LPLSWRQRLKTVLNSNRFTGSGFTDAHNVVTEPVARNSSPYEGRPLCCGNNKCMPICP : 228
CFR10819.1       : LPLSWRQRLKTVLNSSFNGS-----DRNVVTEPVARNSSPYEGRPLCCGNNKCMPICP : 223
WP_050299034.1   : LPLSWRQRLNTVLNSSFNGS-----DRNVVTEPVARNSSPYEGRPLCCGNNKCMPICP : 223
WP_049610421.1   : LPLSWRQRLKSVLNSNRFTGSGFTDAHNVVTEPVARNSSPYEGRPLCCGNNKCMPICP : 228
WP_004877956.1   : LPLSWRQRLKTVLNSNRFTGSGFTDAHNVVTEPVARNSSPYEGRPLCCGNNKCMPICP : 228
WP_046050437.1   : LPLSWRQRLKTVLNSTFNGS-----RRDVVTEPVARNSSPYEGRPLCCGNNKCMPICP : 223
CFR23261.1       : LPLSWRQRLKTVLNSTFNGS-----NRDVVTEPVARNSSPYEGRPLCCGNNKCMPICP : 223
```

Fig. 2-5

```
                             *         260          *         280          *         300
Sequence3       : GAMYKGIVHVEKAERKGAKLIENAVVKLETGPDKRIVAAYKDKTGAKRVEGKYFKL : 283
WP_020067867.1  : GAMYKGIVHVEKAEQKGARLIANAVVKLEKGTDKRITAAYKDAQGSKRVEGKYFKL : 284
WP_027798558.1  : GAMYKGIVHVEKAEQKGAKLIDNAVVKLEKGADKPITAAYKDAEGSKRVEGKYFKL : 284
WP_017774216.1  : GAMYKGIVHVEKAEMKGAKLIDNAVVKRLEKGSNKPIVAAYKDPQHISKRVEGKYFKL : 280
WP_035557405.1  : GAMYKGIVHVEKAEQKGAKLIVNAVVKLEKGADKRIVAALYRDPQGKYRVEGKYFKL : 288
WP_028194543.1  : GAMYKGIVHVEKAEQKGAKLIVNAVVKLEKGADKRITAAYKDPQGSKRVEGKYFKL : 284
WP_048931828.1  : GAMYKGIFHVEKAEQKGARLIENAVVFPLEKGANKRIVAARYKDAKGVKRVEGKWFKL : 280
WP_039597686.1  : GAMYKGIFHVEKAEQKGARLIENAVVFKLEKGTNKRIVAARYKDAKGAKRVEGKWFKL : 280
WP_021195199.1  : GAMYKGIFHVEKAEQKGARLIENAVVFKLEKGANKRIVAARYKDAKGVKRVEGKWFKL : 280
WP_027677929.1  : GAMYKGIVHVEKAEQKGARLIENAVVFKLEKGPNKRIVAARYKDSKGAKRVEGKWFKL : 280
WP_004629448.1  : GAMYKGIVHVEKAEQKGARLIENAVVFKLEKGPNKRIVAARYKDSKGAKRVEGKWFKL : 280
WP_024976326.1  : GAMYKGIVHVEKAEQKGARLIENAVVFKLEKGANKRIVAARYKDSKGAKRVEGKWFKL : 280
WP_045204558.1  : GAMYKGIFHVEKAEQKGARLIENAVVFKLEKGPNKRIVAARYKDAKGAKRVEGKWFKL : 280
ZP_02007109     : GAMYKGIVHVEKAEQKGARLIENAVVFKLEKGPNKRIVAARYKDSKGAKRVEGKWFKL : 284
WP_045786289.1  : GAMYKGIFHVEKAEQKGARLIENAVVKLEKGANKRIVAARYKDSKGGKRVEGKWFKL : 284
WP_009238767.1  : GAMYKGIVHVEKAEQKGARLIENAVVFKLEKGPNKRIVAARYKDSKGAKRVEGKWFKL : 284
CBJ51936.1      : VGAMYKGIVHVEKAEQKGARLIENAVVFKLEKGAGKPIVAHYKDPKGVDKRVEGKWFKL : 283
WP_020749404.1  : GAMYKGIVHVEKAEQKGARLIENAVVKLEKGAGKPIVAAHYKDPQSVDKRVEGKWFKL : 283
WP_011000725.1  : GAMYKGIVHVEKAEQKGARLIENAVVKLEKGAGKRIVAAHYKDPKGVDKRVEGKWFKL : 283
WP_028352718.1  : GAMYKGIVHVEKAEQKGARLIENAVVKLEKGAGKRIVAAHYKDPKGVDKRVEGKWFKL : 283
WP_016727135.1  : GAMYKGIVHVEKAEQKGARLIENAVVKLEKGAGKRIVAAHYKDPKGVDKRVEGKWFAL : 283
WP_019717688.1  : GAMYKGIVHVEKAEQKGARLIENAVVKLEKGAGKRIVAAHYKDPKGVDKRVEGKWFKL : 283
WP_020831435.1  : GAMYKGIVHVEKAEQKGARLIENAVVKLEKGAGKRIVAAHYKDPKGVDKRVEGKWFKL : 283
YP_002260434    : GAMYKGIVHVEKAEQKGARLIENAVVKLEKGAGRRIVAAHYKDPKGVDKRVEGKWFKL : 284
WP_003279244.1  : GAMYKGIVHVEKAEQKGARLIENAVVKLEKGAGRPIVAAHYKDPKGVDKRVEGKWFKL : 266
WP_039568928.1  : GAMYKGIVHVEKAEQKGARLIENAVVKLEKGAGRPIVAAHYKDPKGVDKRVEGKWFKL : 284
WP_050138572.1  : GAMYKAITHVEKAERKGAIVRPQAVVKLEKNDQQQITAAFKDAQGNKRAEGKYFKL : 283
WP_049608172.1  : GAMYKGITHVEKAERKGAIVRPQAVVKLEKNDQQQITAAFKDAQGNKRAEGKFFKL : 288
WP_050140675.1  : GAMYKGITHVEKAERKGAIVRPQAVVKLEKNDQQQITAAFKDAQGNKRAEGKYFKL : 283
WP_050101384.1  : GAMYKGITHVEKAERKGAIVRPQAVVKLEKNDQQQITAAFKDAQGNKRAEGKYFKL : 283
WP_050151802.1  : GAMYKGITHVEKAERKGAIVRPQAVVKLEKNDQQQITAAFKDAQGNKRAEGQYFKL : 283
WP_050107996.1  : GAMYKGITHVEKAERKGAVVRPQAVVKLEKNDQQQITAAFKDAQGNKRAEGQYFKL : 283
WP_050146890.1  : GAMYKGITHVEKAEPKGAIVRPQAVVKLEKNDQQQITAAFKDAQGNKRAEGQYFKL : 283
WP_050135114.1  : GAMYKGITHVEKAERKGAIVRPQAVVKLEKNDQQQITAAFKDAQGNKRAEGQYFKL : 283
WP_050122940.1  : GAMYKGITHVEKAERKGAVVRPQAVVKLEKNDQQQITAAFKDAQGNKRAEGQYFKL : 283
WP_050113306.1  : GAMYKAITHVEKAELKGAIIRPQAVVKLEKNVQQQITAAFKDAQGNKRAEGKYFKL : 283
WP_019081810.1  : GAMYKAITHVEKAELKGAVIRPQAVVKLEKNDQQQITAAFKDAQGNKRAEGKYFKL : 283
CQH40496.1      : GAMYKAITHVEKAELKGAVIRPQAVVKLEKNDQQQITAAFKDAQGNKRAEGKYFKL : 283
WP_050076365.1  : GAMYKAITHVEKAELKGAVIRPQAVVKLEKNDQQQITAAFKDAQGNKRAEGKYFKL : 283
CFQ84255.1      : GAMYKAITHVEKAELKGAIIRPQAVVKLEKNDQQQITAAFKDAQGNKRAEGKYFKL : 283
CFB68626.1      : GAMYKAITHVEKAELKGAIIRPQAVVKLEKNDQQQIAAAFKDAQGNKRAEGKYFKL : 283
WP_019083704.1  : GAMYKAITHVEKAELKGAIIRPQAVVKLEKNDQQQITAAFKDAQGNKRAEGKYFKL : 283
WP_004391242.1  : GAMYKAITHVEKAELKGAIIRPQAVVKLEKDDQQQITAAFKDAQGNKRAEGKYFKL : 283
WP_050130822.1  : GAMYKGITHVEKAERKGAVRPQAVVKLEKNDQQHITAAFKDAQGNKRAEGQYFKL : 283
WP_048616917.1  : GAMYKGITHVEKAELKGAIVRPQAVVQLEKNDQQQITAAFKDAQGNKRAEGKFFKL : 288
WP_050157528.1  : GAMYKAITHVEKAELKGAVIRPQAVVKLEKNDQQQITAAFKDAQGNKRAEGKYFKL : 283
CNB97617.1      : GAMYKAITHVEKAELKGAIIRPQAVVKLEKNDQQQITAAFKDAQGNKRAEGKYFKL : 283
CRE83670.1      : GAMYKAITHVEKAELSGAIIRPQAVVKLEKNDQQQIAAAFKDAQGNKRAEGKYFKL : 283
WP_038635282.1  : GAMYKAITHVEKAELKGAIIRPQAVVQLEKDDQQQITAAFKDAQGNKRAEGKYFKL : 283
CQQ92408.1      : GAMYKAITHVEKAELKGAVIRPQAVVKLEKNDQQQITAAFKDAQGNKRAEGKYFKL : 283
WP_049679386.1  : GAMYKGITHVEKAELKGAIVRPQAVVKLEKNDQQQITAAFKDAQGNKRAEGKFFKL : 288
WP_049648565.1  : GAMYKGITHVEKAELKGAIVRPQAVVKLENEQQQITAAFKDAQGNKRAEGKFFKL : 288
WP_050159872.1  : GAMYKGITHVEKAELKGAIIRPQAVVKLEKNDQQQITAAFKDAQGNKRAEGKYFKL : 283
WP_050144494.1  : GAMYKGITHVEKAELKGAIVRPQAVVKLEKNDQQQITAAFKDAQGNKRAEGKFFKL : 288
CFR10819.1      : GAMYSGITHVEKAEPKGAIVRPQAVVKLEKNDQQHITAAFKDAQGNKRAEGQYFKL : 283
WP_050299034.1  : GAMYKGITHVEKAEPKGAIVRPQAVVKLEKNDQQHITAAFKDAQGNKRAEGQYFKL : 283
WP_049610421.1  : GAMYKGITHVEKAELKGAIVRPQAVVKLEKNDQQQITAAFKDAQGNKRAEGKFFKL : 288
WP_004877956.1  : GAMYKGITHVEKAELKGAIVRPQAVVKLEKNDQQQITAAFKDAQGNQRAEGKFFKL : 288
WP_046050437.1  : GAMYKAITHVEKAELKGAVIRPQAVVKLEKNDQQQITAAFKDAQGNKRAEGKYFKL : 283
CFR23261.1      : GAMYKAITHVEKAELKGAIIRPQAVVKLEKNDQQQITAAFKDAQGNKRAEGKYFKL : 283
```

Fig. 2-6

```
                            *         320         *         340         *         360
Sequence3        : AANGIEIPKILLNSANRDFPNGANSDMVGRNLMDRPGTQSFYASKLWPGRGPQEMT : 343
WP_020067867.1   : AANGIEIPKINLSQHDFPNGGNSDMVGRNLMDRPGTQIFYADKLWPGRGPQEMT : 344
WP_027798558.1   : AANGIEIPKILLNSHDFPNGGNSDMVGRNLMDRPGTQSFYADKLWPGRGPQEMT : 344
WP_017774216.1   : AANGIEIPKILLNSHDFPNGGNSDMVGRNLMDRPGTQSFYADKLWPGRGPQEMT : 340
WP_035557405.1   : AANGIEIPKILLNSHDFPNGGNSDMVGRNLMDRPGTQSFYADKLWPGRGPQEMT : 348
WP_028194543.1   : AANGIEIPKILLNSHDFPHGGNSDMVGRNLMDRPGTQIFYADKLWPGRGPQEMT : 344
WP_048931828.1   : AANGIEIPKILLNSQDFPKGGNSDMVGRNLMDRPGTQSFYADKLWPGRGPQEMT : 340
WP_039597686.1   : AANGIEIPKILLNSQDYPKGGNSDMVGRNLMDRPGTQIFYADRKLWPGRGPQEMT : 340
WP_021195199.1   : AANGIEIPKILLNSQDYPKGGNSDMVGRNLMDRPGTQSFYADRKLWPGRGPQEMT : 340
WP_027677929.1   : AANGIEIPKILLNSQDFPKGGNSDMVGRNLMDRPGTQSFYADRKLWPGRGPQEMT : 340
WP_004629448.1   : AANGIEIPKILLNSQDFPKGGNSDMVGRNLMDRPGTQSFYADRKLWPGRGPQEMT : 340
WP_024976326.1   : AANGIEIPKILLNSQDFPKGGNSDMVGRNLMDRPGTQSFYADRKLWPGRGPQEMT : 340
WP_045204558.1   : AANGIEIPKILLNSQDFPKGGNSDMVGRNLMDRPGTQSFYADRKLWPGRGPQEMT : 340
ZP_02007109      : AANGIEIPKILLNSQDFPKGGNSDMVGRNLMDRPGTQSFYADRKLWPGRGPQEMT : 344
WP_045786289.1   : AANGIEIPKILLNSHDFPKGGNSDMVGRNLMDRPGTQSFYADRKLWPGRGPQEMT : 344
WP_009238767.1   : AANGIEIPKILLNSQDFPKGGNSDMVGRNLMDRPGTQSFYADRKLWPGRGPQEMT : 344
CBJ51936.1       : AANGIEIPKILLNSAAFPRGGNSDMVGRNLMDRPGTQSFYADRKLWPGRGPQEMT : 343
WP_020749404.1   : AANGIEIPKILLNSGADVPKGGNSDMVGRNLMDRPGTQSFYADRKLWPGRGPQEMT : 343
WP_011000725.1   : AANGIEIPKILLNSGADFPKGGNRSDMVGRNLMDRPGTQSFYADRKLWPGRGPQEMT : 343
WP_028852718.1   : AANGIEIPKILLNSGADFPKGGNRSDMVGRNLMDRPGTQSFYADRKLWPGRGPQEMT : 343
WP_016727135.1   : AANGIEIPKILLNSGADFPKGSNSDMVGRNLMDRPGTQSFYADRKLWPGRGPQEMT : 343
WP_019717688.1   : AANGIEIPKILLNSGADFPKGGNSDMVGRNLMDRPGTQSFYADRKLWPGRGPQEMT : 343
WP_020831435.1   : AANGIEIPKILLNSGADFPKGGNRSDMVGRNLMDRPGTQSFYADRKLWPGRGPQEMT : 343
YP_002260434     : AANGIEIPKILLNSEAFPRGGNSDMVGRNLMDRPGTQSFYADRKLWPGRGPQEMT : 344
WP_003279244.1   : AANGIEIPKILLNSEAFPRGGNSDMVGRNLMDRPGTQGFYADRKLWPGRGPQEMT : 346
WP_039568928.1   : AANGIEIPKILLNSEAFPRGGNRSDMVGRNLMDRPGTQSFYADRKLWPGRGPQEMT : 344
WP_050138572.1   : AANGIEIPKILLNSDKNPLGGNSDMVGRNLMDRPGTQTFMANPLWPGRGPQEMT : 343
WP_049608172.1   : AANGIEIPKILLNSDKNPRGGNSDMVGRNLMDRPGTQTFMASPLWPGRGPQEMT : 348
WP_050140675.1   : AANGIEIPKILLNSDKNPLGIGNSDMVGRNLMDRPGTQTFMANPLWPGRGPQEMT : 343
WP_050101384.1   : AANGIEIPKILLNSDKNPLGIGNSDMVGRNLMDRPGTQTFMANPLWPGRGPQEMT : 343
WP_050151802.1   : AANGIEIPKILLSADKNPRGGNSDMVGRNLMDRPGTQTFMASPLWPGRGPQEMT : 343
WP_050107996.1   : AANGIEIPKILLNSNDKNPRGGNSDMVGRNLMDRPGTQTFMASPLWPGRGPQEMT : 343
WP_050146890.1   : AANGIEIPKILLNSDKNPRGGNSDMVGRNLMDRPGTQTFMASPLWPGRGPQEMT : 343
WP_050135114.1   : AANGIEIPKILLNSDKNPRGGNSDMVGRNLMDRPGTQTFMASPLWPGRGPQEMT : 343
WP_050122940.1   : AANGIEIPKILLNSDKNPRGGNSDMVGRNLMDRPGTQTFMANPLWPGRGPQEMT : 343
WP_050113306.1   : AANGIEIPKILLRSINDKNPLGGNSDMVGRNLMDRPGTQTFMASPLWPGRGPQEMT : 343
WP_019081810.1   : AANGIEIPKILLNSDKNPLGGNSDMVGRNLMDRPGTQTFMANPLWPGRGPQEMT : 343
CQH40496.1       : AANGIEIPKILLNSDKNPLGGNSDMVGRNLMDRPGTQTFMANPLWPGRGPQEMT : 343
WP_050076365.1   : AANGIEIPKILLNSDKNPLGGNSDMVGRNLMDRPGTQTFMANPLWPGRGPQEMT : 343
CFQ84255.1       : AANGIEIPKILLNSDKNPLGGNSDMVGRNLMDRPGTQTFMANPLWPGRGPQEMT : 343
CFB68626.1       : AANGIEIPKILLNSDKNPLGGNSDMVGRNLMDRPGTQTFMANPLWPGRGPQEMT : 343
WP_019083704.1   : AANGIEIPKILLNSDKNPLGGNSDMVGRNLMDRPGTQTFMANPLWPGRGPQEMT : 343
WP_004391242.1   : AANGIEIPKILLNSDKNPLGGNSDMVGRNLMDRPGTQTFMASPLWPGRGPQEMT : 343
WP_050130822.1   : AANGIEIPKILLNSDKNPRGGNSDMVGRNLMDRPGTQTFMASPLWPGRGPQEMT : 343
WP_048616917.1   : AANGIEIPKILLNSEKNPRGGNSDMVGRNLMDRPGTQTFMASPLWPGRGPQEMT : 348
WP_050157528.1   : AANGIEIPKILLNSDKNPLGGNSDMVGRNLMDRPGTQTFMANPLWPGRGPQEMT : 343
CNB97617.1       : AANGIEIPKILLNSDKNPLGGNSDMVGRNLMDRPGTQTFMANPLWPGRGPQEMT : 343
CRE83670.1       : AANGIEIPKILLNSDKNPLGGNSDMVGRNLMDRPGTQTFMANPLWPGRGPQEMT : 343
WP_038635282.1   : AANGIEIPKILLNSNDKNPLGGNSDMVGRNLMDRPGTQTFMANPLWPGRGPQEMT : 343
CQQ92408.1       : AANGIEIPKILLNSDKNPLGGNSDMVGRNLMDRPGTQTFMANPLWPGRGPQEMT : 343
WP_049679386.1   : AANGIEIPKILLISEKNPHGGNSDMVGRNLMDRPGTNTFMASPLWPGRGPQEMT : 348
WP_049648565.1   : AANGIEIPKILLISEKNPHGGNSDMVGRNLMDRPGTQTFMASPLWPGRGPQEMT : 348
WP_050159872.1   : AANGIEIPKILLNSDKNPLGGNSDMVGRNLMDRPGTQTFMANPLWPGRGPQEMT : 343
WP_050144494.1   : AANGIEIPKILLISEKNPHGGNSDMVGRNLMDRPGTQTFMASPLWPGRGPQEMT : 348
CFR10819.1       : AANGIEIPKILLNSDKNPLGGNSDMVGRNLMDRPGTQTFMASPLWPGRGPQEMT : 343
WP_050299034.1   : AANGIEIPKILLNSDKNPLGGNSDMVGRNLMDRPGTQTFMASPLWPGRGPQEMT : 343
WP_049610421.1   : AANGIEIPKILLISEQNPHGGNSDMVGRNLMDRPGTQTFMASPLWPGRGPQEMT : 348
WP_004877956.1   : AANGIEIPKILLNSEKNPHGGNSDMVGRNLMDRPGTQTFMASPLWPGRGPQEMT : 348
WP_046050437.1   : AANGIEIPKILLNSDKNPLGGNSDMVGRNLMDRPGTQTFMANPLWPGRGPQEMT : 343
CFR23261.1       : AANGIEIPKILLNSDKNPLGGNSDMVGRNLMDRPGTQTFMASPLWPGRGPQEMT : 343
```

Fig. 2-7

```
                             *       380         *       400         *       420
Sequence3       : SXXGFRDGPFRXTEAXKIHLSNXSRIXQETQKIFXA-XKLMKPDELXAQIRDXSARYVX : 402
WP_020067867.1  : SXXGFRDGPFRXTEAXKIHLSNMSRVXQETQKIFXQ-XKLIKPAELXAQIRDXSARXVE : 403
WP_027798558.1  : SXXGFRDGPFRXTEAXKIHLSNXSRIXQETQRIFGQ-XKLIKPAELXAQIRDXSARXVE : 403
WP_017774216.1  : SXXGFRDGPFRSQQAXKIHLSNXSRIXQETQRIFGQ-XKKLIKPADLXAQIRDXSARYVX : 399
WP_035557405.1  : SXXGFRDGPFRXTEAXKIHLSNXSRIXQETQKIFXQ-XKLIKPAELXAQIRDXSARXVE : 407
WP_028194543.1  : SXXGFRDGPFRXNEAXKIHLSNXSRIXQETQKIFXQ-XKLIKPAELXAQIRDXSARXVE : 403
WP_048931828.1  : SXXGFRDGPFRXTQAGKKLHLSNXSRIEQETQRIFXE-XKLIKPAELXARIRDQXARYVE : 399
WP_039597686.1  : SXXGFRDGPFRXTQAGKKLHLSNXSRIEQETQRIFXE-XKLIKPAELXARIRDQXARXVE : 399
WP_021195199.1  : SXXGFRDGPFRXTQAGKKLHLSNXSRIEQETQRIFXE-XKLIKPAELXARIRDQXARXVE : 399
WP_027677929.1  : SXXGFRDGPFRXTQAGKKLHLSNXSRIEQETQRIFXE-XKLIKPAELXARIRDQXARYVX : 399
WP_004629448.1  : SXXGFRDGPFRXTQAGKKLHLSNMSRIEQETQRIFXE-XKLIKPAELXARIRDQXARYVX : 399
WP_024976326.1  : SXXGFRDGPFRXTQAGKKLHLSNXSRIEQETQRIFXE-XKLIKPAELXARIRDQXARYVX : 399
WP_045204558.1  : SXXGFRDGPFRXTQAGKKLHLSNXSRIEQETQRIFXE-XKLIKPADLXARIRDQXARYVX : 399
ZP_02007109     : SXXGFRDGPFRXTQAGKKLHLSNXSRIEQETQRIFXE-XKLIKPADLXARIRDQXARYVX : 403
WP_045786289.1  : SXXGFRDGPFRXTQAGKKLHLSNXSRIEQETVRIFXE-XKLIKPPELXARIRDQXARYVX : 403
WP_009238767.1  : SXXGFRDGPFRXTQAGKKLHLSNXSRIEQETQRIFXE-XKLIKPADLXARIRDQXARYVX : 403
CBJ51936.1      : SXXGFRDGPFRXTQAGKKLHLSNXSRIEQETARIFXA-XKLKPAELXARIRDQXARYVX : 402
WP_020749404.1  : SXXGFRDGPFRXTQAGKKLHLSNXSRIEQETTRIFXA-XKLKPAELXARIRDQXARYVE : 402
WP_011000725.1  : SXXGFRDGPFRXTQAGKKLHLSNXSRIEQETTRIFXA-XKLKPAELXARIRDQXARYVX : 402
WP_028852718.1  : SXXGFRDGPFRXTQAGKKLHLSNXSRIEQETTRIFXA-XKLKPAELXARIRDQXARYVX : 402
WP_016727135.1  : SXXGFRDGPFRXTQAGKKLHLSNXSRIEQETTRIFXA-XRLKPAELXARIRDQXARYVX : 402
WP_019717688.1  : SXXGFRDGPFRXTQAGKKLHLSNXSRIEQETTRIFXA-XRLKPAELXARIRDQXARYVX : 402
WP_020831435.1  : SXXGFRDGPFRXTQAGKKLHLSNXSRIEQETTRIFXA-XRLKPAELXARIRDQXARYVX : 402
YP_002260434    : SXXGFRDGPFRXMQAGKKLHLSNXSRIEQETARIFXA-XKLKPAELXARIRDQXARYVX : 403
WP_003279244.1  : SXXGFRDGPFRXTQAGKKLHLSNXSRIEQETARIFXA-XKLKPAELXARIRDQXARYVX : 405
WP_039568928.1  : SXXGFRDGPFRXMQAGKKLHLSNXSRIEQETARIFXA-XKLKPAELXARIRDQXARYVX : 403
WP_050138572.1  : SXXGFRDGXFRSEYAXKKIHLSNXSRTXQVTIELLXQ-XGLQLGPQLXAKIRDXARXVX : 402
WP_049608172.1  : SMXGFRDGXFRXDFAXKKIHLSNXSRTXQVTIELLXQ-XDLPLGPQLXAKIRDXAKXVA : 407
WP_050140675.1  : SXXGFRDGXFRSEYAXKKIHLSNXSRTXQVTIEQLXQ-XDLQLGPQLXAKIRDXARXVX : 402
WP_050101384.1  : SXXGFRDGXFRSEYAXKKIHLSNXSRTXQVTIEQLXQ-XDLQLGPQLXAKIRDXARXVX : 402
WP_050151802.1  : SXXGFRDGXFRSEYAXKKIHLSNXSRTXQVTIELLSQ-XDLQLGPQLXAKIRDXARXVX : 402
WP_050107996.1  : SXXGFRDGXFRSEYAXKKIHLSNXSRTXQVTIELLSQ-XDLQLGPQLXAKIRDXARXVX : 402
WP_050146890.1  : SXXGFRDGXFRSEYAXKKIHLSNXSRTXQVTIELLSQ-XDLQLGPQLXAKIRDXAPXVX : 402
WP_050135114.1  : SXXGFRDGXFRSEYAXKKIHLSNXSRTXQVTIELLSQ-XDLQLGPQLXAKIRDXARXVX : 402
WP_050122940.1  : SXXGFRDGXFRSEYAXKKIHLSNXSRTXQVTIELLSQ-XDLQLGPQLXAKIRDXARXVX : 402
WP_050113306.1  : SXXGFRDGXFRXEYAXKKIHLSNXSRTXQVTIELLXQ-XELQLGPQLXAKIRDXARXVX : 402
WP_019081810.1  : SXXGFRDGXFRSEYAXKKIHLSNXSRTXQVTIELLXQ-XELQLGPQLXAKIRDXARXVX : 402
CQH40496.1      : SXXGFRDGXFRSEYAXKKIHLSNXSRTXQVTIELLXQ-XELQLGPQLXAKIRDXARXVX : 402
WP_050076365.1  : SXXGFRDGXFRSEYAXKKIHLSNXSRTXQVTIELLXQ-XELQLGPQLXAKIRDXARXVX : 402
CFQ84255.1      : SXXGFRDGXFRSEYAXKKIHLSNXSRTXQVTIELLXQ-XELQLGPQLXAKIRDXARXVX : 402
CFB68526.1      : SXXGFRDGXFRSEYAXKKIHLSNXSRTXQVTIELLXQ-XELQLGPQLXAKIRDXARXVX : 402
WP_019083704.1  : SXXGFRDGXFRSEYAXKKIHLSNXSRTXQVTIELLXQ-XELQLGPQLXAKIRDXARXVX : 402
WP_004391242.1  : SXXGFRDGXFRXEYAXKKIHLSNXSRTXQVTIELLXQ-XELQLGPQLXAKIRDXARXVX : 402
WP_050130822.1  : SXXGFRDGXFRSEYAXKKIHLSNXSRTXQVTIELLSQ-XDLQLGPQLXAKIRDXARXVX : 402
WP_048616917.1  : SXVGFRDGXFRXDFAXKKIHLSNXSRTXQVTIELLXQ-XDLQLGPQLEAKIRDXARXVX : 407
WP_050157528.1  : SXXGFRDGXFRSEYAXKKIHLSNXSRTXQVTIELLXQ-XELQLGPQLXAKIRDXARXVX : 402
CNB97617.1      : SXXGFRDGXFRSEYAXKKIHLSNXSRTXQVTIELLXQ-XELQLGPQLXAKIRDXARXVX : 402
CRE83670.1      : SXXGFRDGXFRSEYAXKKIHLSNXSRTXQVTIELLXQ-XELQLGPQLXAKIRDXARXVX : 402
WP_038635282.1  : SXXGFRDGXFRXEYAXKKIHLSNXSRTXQVTIELLXQ-XELQLGPQLXAKIRDXARXVX : 402
CQQ92408.1      : SXXGFRDGXFRSEYAXKKIHLSNXSRTXQVTIELLXQ-XELQLGPQLXAKIRDXARXVX : 402
WP_049679386.1  : SMXGFRDGXFRXDFAXKKIHLSNXSRTXQVTIELLXQ-XDLQLGPQLEAKIRDXARXVX : 407
WP_049648565.1  : SMXGFRDGXFRXDFAXKKIHLSNXSRTXQVTIELLXQ-XDLQLGPQLEAKIRDXARXVX : 407
WP_050159872.1  : SXXGFRDGXFRSEYAXKKIHLSNXSRTXQVTIELLXQ-XELQLGPQLXAKIRDXARXVX : 402
WP_050144494.1  : SMVGFRDGXFRXDFAXKKIHLSNXSRTXQVTIELLXQ-XDLQLGPQLEAKIRDXARXVX : 407
CFR10819.1      : SXXGFRDGXFRSEYAXKKIHLSNXSRTXQVTIELLSQ-XDLQLGPQLXAKIRDXARXVX : 402
WP_050299034.1  : SXXGFRDGXFRSEYAXKKIHLSNXSRTXQVTIELLSQ-XDLQLGPQLXAKIRDXARXVX : 402
WP_049610421.1  : SMXGFRDGXFRXDFAXKKIHLSNXSRTXQVTIELLXQ-XDLQLGPQLEAKIRDXARXVX : 407
WP_004877956.1  : SMVGFRDGXFRXDFAXKKIHLSNXSRTXQVTIELLXQ-XDLQLGPQLEAKIRDXARXVX : 407
WP_046050437.1  : SXXGFRDGXFRSEYAXKKIHLSNXSRTXQVTIELLXQ-XELQLGPQLXAKIRDXARXVX : 402
CFR23261.1      : SXXGFRDGXFRXEYAXKKIHLSNXSRTXQVTIELLXQ-XELQLGPQLXAKIRDXARXVX : 402
```

```
                              *         500         *         520         *         540
Sequence3       : D V NDE APNNHITGS MGADAP VVDKHCR FDHPKLF S SATMPTVGTVNVTL : 522
WP_020067867.1  : SDIR DDE APNNHITGA MGSD P VVDKHCR FDHPKLF S SATMPTVGTVNVTL : 523
WP_027798558.1  : DIEYQDE APNNHITGA MGSD R VVDKHCR FDHPNLF S SATMPTVGTVNVTL : 523
WP_017774216.1  :  E DDE APNNHITSSV MGSD RN VVDKHCR FDHPNLFVS ATMPTVGTVNVTL : 519
WP_035557405.1  :  IEYQDE APNNHITGA MGSD R VVDKHCR FDHPNLF S SATMPTVGTVNVTL : 527
WP_028194543.1  :  IEYQDE APNNHITGA MGSD R VVDKHCR FDHPNLF S SATMPTVGTVNVTL : 523
WP_048931828.1  : D  NDD APNNHITGA MGAD   VVDK CR FDHPKLF S S TMPTVGTVNVTL : 519
WP_039597686.1  : D Q NDA APNNHITGA MGAD  AVVDK CR FDHPKLF S S TMPTVGTVNVTL : 519
WP_021195199.1  : D Q NDD APNNHITGA MGAD   VVDK CR FDHPNLF S S TMPTVGTVNVTL : 519
WP_027677929.1  :  N E DDD APNNHITGA MGAD   VVDK CR FDHPNLF S S TMPTVGTVNVTL : 519
WP_004629448.1  :  N E DDD APNNHITGA MGAD  N VVDK CR FDHPNLF S S TMPTVGTVNVTL : 519
WP_024976326.1  :  N E DDD APNNHITGA MGAD   VVDK CR FDHPNLF S S TMPTVGTVNVTL : 519
WP_045204558.1  :  N E DDD APNNHITGA MGAD   VVDK CR FDHPNLF S S TMPTVGTVNVTL : 519
ZP_02007109     :  N E DDD APNNHITGA MGAD   VVDK CR FDHPNLF S S TMPTVGTVNVTL : 523
WP_045786289.1  : D Q DD APNNHITGA MGAD   VVDK CR FDHPNLF S S TMPTVGTVNVTL : 523
WP_009238757.1  :  N E DDD APNNHITGA MGAD   VVDK CR FDHPNLF S S AMPTVGTVNVTL : 523
CBJ51936.1      : D  DD APNNHITGA MGAD   VVDKNCR FDHPNLF S SATMPTVGTVNVTL : 522
WP_020749404.1  : D Q QDD APNNHITGA MGAD   VVDK CR FDHPNLF S SATMPTVGTVNVTL : 522
WP_011000725.1  : D  DDD APNNHITGA MGSD   VVDK CR FDHPKLF S SATMPTVGTVNVTL : 522
WP_028852718.1  : D   DD APNNHITGA MGSD   VVDK CR FDHPNLF S SATMPTVGTVNVTL : 522
WP_016727135.1  : D Q  DD APNNHITGA MGSD   VVDK CR FDHPNLF S SATMPTVGTVNVTL : 522
WP_019717688.1  : D Q DD APNNHITGA MGSD   VVDK CR FDHPNLF SGSATMPTVGTVNVTL : 522
WP_020831435.1  : D Q DD APNNHITGA MGSD   VVDF CR FDHPNLF SGSATMPTVGTVNVTL : 522
YP_002260434    : D Q DD APNNHITGA SMGAD   VVDK CR FDHPNLF S SATMPTVGTVNVTL : 523
WP_003279244.1  : D  DD APNNHITGA MGAD   VVDK CR FDHPKLF S SATMPTVGTVNVTL : 525
WP_039568928.1  : D  DD APNNHITGA MGAD   VVDK CR FDHPKLF S SATMPTVGTVNVTL : 523
WP_050138572.1  :  VQL NN ANNHITGT MGND   VVDS CR HDHKNLF A S VMPTVGSVNCTL : 522
WP_049608172.1  : D K TNN ANNHITGT MGND   VVDS CRAHDHKNLF A S VMPTVGSVNCTL : 527
WP_050140675.1  :  Q NN ANNHITGT MGND   VVDS CR HDHKNLF A S VMPTVGSVNCTL : 522
WP_050101384.1  :  Q NN ANNHITGT MGND   VVDS CR HDHKNLF A S VMPTVGSVNCTL : 522
WP_050151802.1  :  Q NN ANNHITGT MGND   VVDS CR HDHKNLF A S VMPTVGSVNCTL : 522
WP_050107996.1  :  Q NN ANNHITGT MGND   VVDS CR HDHKNLF A S VMPTVGSVNCTL : 522
WP_050146890.1  :  Q NN ANNHITGT MGND   VVDS CR HDHKNLF A S VMPTVGSVNCTL : 522
WP_050135114.1  :  Q NN ANNHITGT MGND   VVDS CR HDHKNLF A S VMPTVGSVNCTL : 522
WP_050122940.1  :  Q NN ANNHITGT MGND   VVDS CR HDHKNLF A S VMPTVGSVNCTL : 522
WP_050113306.1  :  Q NN ANNHITGT MGND   VVDS CR HDHKNLF A S VMPTVGSVNCTL : 522
WP_019081810.1  :  NN ANNHITGT MGND   VVDS CR HDHKNLF A S VMPTVGSVNCTL : 522
CQH40496.1      :  Q NN ANNHITGT MGND   VVDS CR HDHKNLF A S VMPTVGSVNCTL : 522
WP_050076365.1  :  Q NN ANNHITGT MGND   VVDS CR HDHKNLF A S VMPTVGSVNCTL : 522
CFQ84255.1      :  Q NN ANNHITGT MGND   VVDS CR HDHKNLF A S VMPTVGSVNCTL : 522
CFB68626.1      :  Q NN ANNHITGT MGND   VVDS CR HDHKNLF A S VMPTVGSVNCTL : 522
WP_019083704.1  :  Q NN ANNHITGT MGND   VVDS CR HDHKNLF A S VMPTVGSVNCTL : 522
WP_004391242.1  :  Q NN ANNHITGT MGND   VVDS CR HDHKNLF A S VMPTVGSVNCTL : 522
WP_050130822.1  :  Q NN ANNHITGT MGND   VVDS CR HDHKNLF A S VMPTVGSVNCTL : 522
WP_048661917.1  :  K NN ANNHITGT MGDD   VVDS CR HDHKNLF A S VMPTVGSVNCTL : 527
WP_050157529.1  :  Q NN ANNHITGT MGND   VVDS CR HDHKNLF A S VMPTVGSVNCTL : 522
CNB97617.1      :  Q NN ANNHITGT MGND   VVDS CR HDHKNLF A S VMPTVGSVNCTL : 522
CRE83670.1      :  Q NN ANNHITGT MGND   VVDS CR HDHKNLF A S VMPTVGSVNCTL : 522
WP_038635282.1  :  Q NN ANNHITGT MGND   VVDS CRSHDHKNLF A S VMPTVGSVNCTL : 522
CQQ92408.1      :  Q NN ANNHITGT MGND   VVDS CR HDHKNLF A S VMPTVGSVNCTL : 522
WP_049679386.1  :  K NN ANNHITGT MGDD   VVDS CR HDHKNLF A S VMPTVGSVNCTL : 527
WP_049648565.1  :  K NN ANNHITGT MGDD   VVDS CR HDHKNLF A S VMPTVGSVNCTL : 527
WP_050159872.1  :  Q NN ANNHITGT MGND   VVDS CR HDHKNLF A S VMPTVGSVNCTL : 522
WP_050144494.1  :  K NN ANNHITGT MGDD   VVDS CR HDHKNLF A S VMPTVGSVNCTL : 527
CFR10819.1      :  Q NN ANNHITGT MGND   VVDS CR HDHKNLF A S VMPTVGSVNCTL : 522
WP_050299034.1  : A Q NN ANNHITGT MGND   VVDS CR HDHKNLF A S VMPTVGSVNCTL : 522
WP_049610421.1  :  K NN ANNHITGT MGDD   VVDS CR HDHKNLF A S VMPTVGSVNCTL : 527
WP_004877956.1  :  IK NN ANNHITGT MGDD   VVDS CR HDHKNLF A S VMPTVGSVNCTL : 527
WP_046050437.1  :  Q NN ANNHITGT MGND   VVDS CR HDHKNLF A S VMPTVGSVNCTL : 522
CFR23261.1      :  Q NN ANNHITGT MGND   VVDSHCR HDHKNLF A S VMPTVGSVNCTL : 522
```

Fig. 2-10

```
Sequence3        : XIAALALRMSDTLKKEX-- : 539
WP_020067867.1   : XIAALALRMXDQLKKEX-- : 540
WP_027798558.1   : XIAALALRMXDQLKKEA-- : 540
WP_017774216.1   : XIAALALRMXDQLKKEX-- : 536
WP_035557405.1   : SIAALALRMXDQLKKEX-- : 544
WP_028194543.1   : XIAALALRMXDQLKKEX-- : 540
WP_048931828.1   : XIAALALRXXDQLKKEA-- : 536
WP_039597686.1   : XIAALALRXXDQLKKEA-- : 536
WP_021195199.1   : XIAALALRXXDQLKKEA-- : 536
WP_027677929.1   : XIAALALRXXDQLKKEA-- : 536
WP_004629448.1   : XIAALALRXXDQLKKEA-- : 536
WP_024976326.1   : XIAALALRXXDQLKKEA-- : 536
WP_045204558.1   : XIAALALRXXDQLKKEA-- : 536
ZP_02007109      : XIAALALRXXDQLKQEA-- : 540
WP_045786289.1   : XIAALALRXXDQLKKEA-- : 540
WP_009238767.1   : XIAALALRXXDQLKKEA-- : 540
CBJ51936.1       : XIAALALRXXDQLKKEA-- : 539
WP_020749404.1   : XIAALALRXXDQLKKEA-- : 539
WP_011000725.1   : XIAALALRXXDQLKKEA-- : 539
WP_028852718.1   : XIAALALRXXDQLKKEA-- : 539
WP_016727135.1   : XIAALALRXXDQLKKEA-- : 539
WP_019717688.1   : XIAALALRXXDQLKKEA-- : 539
WP_020831435.1   : XIAALALRXXDQLKKEA-- : 539
YP_002260434     : XIAALALRXXDRLKKEA-- : 540
WP_003279244.1   : XIAALALRXXDRLKKEA-- : 542
WP_039568928.1   : XIAALTLRXXDRLKKEA-- : 540
WP_050138572.1   : XIAALSLRXXETLKAEX-- : 539
WP_049608172.1   : XIAALSLRXXETLKAEX-- : 544
WP_050140675.1   : XIAALSLRXXETLKAEX-- : 539
WP_050101384.1   : XIAALSLRXXETLKAEX-- : 539
WP_050151802.1   : XIAALSLRXXETLKAEX-- : 539
WP_050107996.1   : XIAALSLRXXETLKAEX-- : 539
WP_050146890.1   : XIAALSLRXXETLKAEX-- : 539
WP_050135114.1   : XIAALSLRXXETLKAEX-- : 539
WP_050122940.1   : XIAALSLRXXETLKAEX-- : 539
WP_050113306.1   : XIAALSLRXXETLKAEX-- : 539
WP_019081810.1   : XIAALSLRXXETLKAEX-- : 539
CQH40496.1       : XIAALSLRXXETLKAEX-- : 539
WP_050076365.1   : XIAALSLRXXETLKAEX-- : 539
CFQ84255.1       : XIAALSLRXXETLKAEX-- : 539
CFB68626.1       : XIAALSLRXXETLKAEX-- : 539
WP_019083704.1   : XIAALSLRXXETLKAEX-- : 539
WP_004391242.1   : XIAALSLRXXETLKAEX-- : 539
WP_050130822.1   : XIAALSLRXXETLKAEX-- : 539
WP_048616917.1   : XIAALSLRXXETLKAEX-- : 544
WP_050157528.1   : XIAALSLRXXETLKAEX-- : 539
CNB97617.1       : XIAALSLRXXETLKAEX-- : 539
CRE83670.1       : XIAALSLRXXETLKAEX-- : 539
WP_038635282.1   : XIAALSLRXXETLKAEX-- : 539
CQQ92408.1       : XIAALSLRXXETLKAEX-- : 539
WP_049679386.1   : XIAALSLRXXETLKAEX-- : 544
WP_049648565.1   : XIAALSLRXXETLKAEX-- : 544
WP_050159872.1   : XIAALSLRXXETLKAEX-- : 539
WP_050144494.1   : XIAALSLRXXETLKAEX-- : 544
CFR10819.1       : XIAALSLRXXETLKAEX-- : 539
WP_050299034.1   : XIAALSLRXXETLKAEX-- : 539
WP_049610421.1   : XIAALSLRXXETLKAEX-- : 544
WP_004877956.1   : XIAALSLRXXETLKTEX-- : 544
WP_046050437.1   : XIAALSLRXXETLKAEX-- : 539
CFR23261.1       : XIAALSLRXXETLKAEX-- : 539
```

Fig. 3-1

```
                              *         20         *         40         *         60
Sequence3        : MADTD------TQKADVKVGSGVAGAIVAQQAMAGKAVILLEAGPRMPRWEIVERFRN :  54
WP_013650283.1   : MAD--------TKADIKIGSGVAGIVAQIAMAGKAVILLEAGPRISRWEIVEKFRN    :  52
CQJ52766.1       : MAD--------TKADIKIGSGVAGIVAQIAMAGKAVILLEAGPRISRWEIVEKFRN    :  52
WP_050539080.1   : MAD--------TKADIKIGSGVAGIVAQIAMAGKAVILLEAGPRISRWEIVEKFRN    :  52
WP_049562931.1   : MAD--------TKADIIIGSGVAGIVAQIAMAGKAVILLEAGPRISRWEIVEKFRN    :  52
CCV62536.1       : MAD--------TKADIKIGSGVAGIVAQIAMAGKAVILLEAGPRISRWEIVEKFRN    :  52
WP_005172530.1   : MAD--------TKADIKIGSGVAGIVAQIAMAGKAVILLEAGPRISRWEIVEKFRN    :  52
WP_011815792.1   : MAD--------TKADIKIGSGVAGIVAQIAMAGRAVILLEAGPRISRWEIVEKFRN    :  52
WP_050290584.1   : MAD--------TKADIIIGSGVAGIVAQIAMAGRAVILLEAGPRISRWEIVEKFRN    :  52
WP_004707861.1   : MAD--------TKADVKIGSGVAGIVAQIAMAGKSVILLEAGPRISRWEIVEKFRN    :  52
CQJ18911.1       : MAD--------TKADIKIGSGVAGIVAQIAMAGKAVILLEAGPRISRWEIVEKFRN    :  52
WP_049600682.1   : MAD--------TKADIIIGSGVAGIVAQIAMAGKAVILLEAGPRISRWEIVEKFRN    :  52
WP_049603209.1   : MAD--------TTADIIIGSGVAGIVAQIAMAGKAVILLEAGPRISRWEIVEKFRN    :  52
CFQ30984.1       : MAD--------TKADIKIGSGVAGIVAQIAMAGKAVILLEAGPRISRWEIVEKFRN    :  52
WP_004702484.1   : MAD--------TTADIIIGSGVAGIVAQIAMAGKAVILLEAGPRISRWEIVEKFER    :  52
WP_049688140.1   : MAD--------TTADIIIGSGVAGIVAQIAMAGKAVILLEAGPRISRWEIVEKFRN    :  52
WP_042548059.1   : MAD--------TTADIIIGSGVAGIVAQIAMAGKAVILLEAGPRISRWEIVEKFRN    :  52
CRX73404.1       : MAD--------IKADIKIGSGVAGIVAQIAMAGKAVILLEAGPRISRWEIVEKFRN    :  52
WP_014609437.1   : MAD--------IKADIKIGSGVAGIVAQIAMAGKAVILLEAGPRISRWEIVEKFRN    :  52
CFQ15314.1       : MAD--------IKADIKIGSGVAGIVAQIAMAGKAVILLEAGPRISRWEIVEKFRN    :  52
WP_050128783.1   : MAD--------IKADIKIGSGVAGIVAQIAMAGKAVILLEAGPRISRWEIVEKFRN    :  52
WP_018433926.1   : MAN--------TQSADIKVGSGVAGSVAQIALAGAVILLEAGPRIPRQIVEKFRN     :  52
WP_018424152.1   : MAN--------TQSADIKVGSGVAGSVAQMALAGAVILLEAGPRIPRQIVEKFRN     :  52
WP_008921043.1   : MAN--------TQSADIKVGSGVAGSVAQIALAGAVILLEAGPRIPRQIVEKFRN     :  52
WP_013092964.1   : MAN--------TQSADIKVGSGVAGSVAQIALAGAVILLEAGPRIPRQIVEKFRN     :  52
WP_027195331.1   : MAN--------TQSADIKVGSGVAGSVAQIALAGAVILLEAGPRIPRQIVEKFRN     :  52
WP_028223852.1   : MAI--------DNSADVKVGSGVAGSVAYQIAQAGAVILLEAGPRIARRQIVEKFRN   :  52
WP_027796285.1   : MAI--------ENSADVKVGSGVAGSVAQIAQAGAVILLEAGPRIARRQIVEKFRN    :  52
WP_028196142.1   : MAN--------SNSADIKVGSGVAGSVAQMALAGAVILLEAGPRIPRQIVEKFRN     :  52
YP_001890482     : MAN--------KNSADIKVGSGVAGSVAQMALAGAVILLEAGPRIPRQIVEKFRN     :  52
```

Fig. 3-2

```
                              *         80         *        100         *        120
Sequence3          :          NDF A YPSSPWAPHP  YGP-PNDY  LKG  KFNSQY R VGGTTWHWAA AWR  : 113
WP_013650283.1     :          DN A YPS S APHP  NP-NN YI KGE  D QY RAVGGTTWHWAA AWR  : 111
CQJ52766.1         :          DN A YPS S APHP  NP-NN YI KGE  D QY RAVGGTTWHWAA AWR  : 111
WP_050539080.1     :          DN A YPS S APHP  NP-NN YI KGE  D QY RAVGGTTWHWAA AWR  : 111
WP_049562931.1     :          DN A YPS S APHP  NP-NN YI KGE  D QY RAVGGTTWHWAA AWR  : 111
CCV62586.1         :          DN A YPS S APHP  NP-NN YI KGE  D QY RAVGGTTWHWAA AWR  : 111
WP_005172530.1     :          DN A YPS S APHP  NP-NN YI KGE  D QY RAVGGTTWHWAA AWR  : 111
WP_011815792.1     :          DN A YPS S APHP  NP-NN YI KGE  D QY RAVGGTTWHWAA AWR  : 111
WP_050290584.1     :          DN A YPS S APHP  NP-NN YI KGE  D QY RAVGGTTWHWAA AWR  : 111
WP_004707861.1     :          DN AAYPS S APHP  NP-NN YI KGE  D QY RAVGGTTWHWAA AWR  : 111
CQJ18911.1         :          DN A YPS S APHP  NP-NN YI KGE  D QY RAVGGTTWHWAA AWR  : 111
WP_049600682.1     :          DN A YPS S APHPQANP-NN YI KGE  D QY RAVGGTTWHWAA AWR  : 111
WP_049603209.1     :          DN A YPS P APHP  NP-NN YI KGE  D QY RAVGGTTWHWAA AWR  : 111
CFQ30984.1         :          DN A YPS S APHPQANP-NN YI KGE  D QYVRAVGGTTWHWAA AWR  : 111
WP_004702484.1     :          DN A YPS P APHP  NP-NN YI KGE  D QY RAVGGTTWHWAA AWR  : 111
WP_049688140.1     :          DN A YPS P APHP  NP-NN YI KGE  D QY RAVGGTTWHWAA AWR  : 111
WP_042548059.1     : S        DN A YPS S APHP  NP-NN YI KGE  D QY RAVGGTTWHWAA AWR  : 111
CRX73404.1         :          DN A YPS S APHP  NP-NN YI KGE  D QY RAVGGTTWHWAA AWR  : 111
WP_014609437.1     :          DN A YPS S APHP  NP-NN YI KGE  D QY RAVGGTTWHWAA AWR  : 111
CFQ15314.1         :          DN A YPS S APHP  NP-NN YI KGE  D QY RAVGGTTWHWAA AWR  : 111
WP_050128783.1     :          DN A YPS S APHP  NP-NN YI KGE  D QY RAVGGTTWHWAA AWR  : 111
WP_018433926.1     : S A  DFAT YPS P APHP  YAP-AN YI KGDY  NSQYVRLVGGTTWHWAAAAWRL  : 111
WP_013424152.1     : S A  DFAT YPS L APHP  YAP-AN YI KGDY  NSQYVRLVGGTTWHWAAAAWRL  : 111
WP_008921043.1     : S V ADFAT YPS P APHP  YAP-AN YI KGDY  NSQYVRLVGGTTWHWAAAAWRL  : 111
WP_013092964.1     : S A  DFAT YPS P APHP  YAP-AN YI KGDY  NSQYVRLVGGTTWHWAAAAWRL  : 111
WP_027195331.1     : S VP DFAT YPS P APHP  YAP-AN YI KGDY  NSQYVRLVGGTTWHWAAAAWRL  : 111
WP_028223852.1     : S A ADFAT YPSSP APHP  YSP-AN YI KGDY  NSQYLRLVGGTTWHWAAAAWRL  : 111
WP_027796285.1     : S A ADFAT YPSSVWAPHP  YSP-PNDYMI KGDY  NSQYLRLVGGTTWHWAAAAWRL  : 111
WP_028196142.1     : S A  DFAT YPS P APHP  YSP-AN YI KGDY  NSQYVRLVGGTTWHWAAAAWRL  : 111
YP_001890482       : S V  DFAT YPS P APHP  YAP-AN YI KGDY  SSQYLRLVGGTTWHWAAAAWRL  : 111
```

```
                            *         200         *         220         *         240
Sequence3        : LPLSFNEQTIKYALNNYDP----------KFHVVIEPVARNSRPYGRPTCCGNNNCMPIQP : 223
WP_013650283.1   : LPLSYNEQRIKVLNSHTENGS------HFDVVIEPVARNSRPYGRPTCCGNNNCMPIQP : 223
CQJ52766.1       : LPLSYNEQRIKVLNSHTENGN------HFDVVIEPVARNSRPYGRPTCCGNNNCMPIQP : 223
WP_050539080.1   : LPLSYNEQRIKVLNSNRETGGFTDAHFNVVIEPVARNSRPYGRPTCCGNNNCMPIQP : 228
WP_049562931.1   : LPLSYNEQRIKVLNSHTENGS------NFDVVIEPVARNSRPYGRPTCCGNNNCMPIQP : 223
CCV62586.1       : LPLSYNEQRIKVLNSHTENGS------HFDVVIEPVARNSRPYGRPTCCGNNNCMPIQP : 223
WP_005172530.1   : LPLSYNEQRIKVLNSHTENGS------HFDVVIEPVARNSRPYGRPTCCGNNNCMPIQP : 223
WP_011815792.1   : LPLSYNEQRIKVLNSHTENGS------HFDVVIEPVARNSRPYGRPTCCGNNNCMPIQP : 223
WP_050290584.1   : LPLSYNEQRIKVLNSHTENGS------NFDVVIEPVARNSRPYNGRPTCCGNNNCMPIQP : 223
WP_004707861.1   : LPLSYNEQRIKVLESHSENGS------DFNVVIEPVARNSRPYGRPTCCGNNNCMPIQP : 223
CQJ18911.1       : LPLSYNEQRIKVLNSHTENGS------HFDVVIEPVARNSRPYGRPTCCGNNNCMPIQP : 223
WP_049600682.1   : LPLSYNEQRIKVLNSNRETGGFTDAHFNVVIEPVARNSRPYGRPTCCGNNNCMPIQP : 228
WP_049603209.1   : LPLSYNEQRIKVLNSNSENGS------RFNVVIEPVARNSRPYGRPTCCGNNNCMPIQP : 223
CFQ30984.1       : LPLSYNEQRIKVLNSNRETGGFTDAHFNVVIEPVARNSRPYGRPTCCGNNNCMPIQP : 228
WP_004702484.1   : LPLSYNEQRIKVLNSNSENGS------RFNVVIEPVARNSRPYGRPTCCGNNNCMPIQP : 223
WP_049668140.1   : LPLSYNEQRIKVLNRNSENGS------RFNVVIEPVARNSRPYGRPTCCGNNNCMPIQP : 223
WP_042548059.1   : LPLSYNEQRIKVLNSNSENGS------RFNVVIEPVARNSRPYGRPTCCGNNNCMPIQP : 223
CRX73404.1       : LPLSYNEQRIKVLNSHTENGS------HFDVVIEPVARNSRPYGRPTCCGNNNCMPIQP : 223
WP_014609437.1   : LPLSYNEQRIKVLNSHTENGS------HFDVVIEPVARNSRPYGRPTCCGNNNCMPIQP : 223
CFQ15314.1       : LPLSYNEQRIKVLNSHTENGS------YFDVVIEPVARNSRPYGRPTCCGNNNCMPIQP : 223
WP_050128783.1   : LPLSYNEQRIKVLNSHTENGS------HFDVVIEPVARNSRPYGRPTCCGNNNCMPIQP : 223
WP_018433926.1   : LPLSYMDQKFSDVLNAQG----------FKVVPEPVARNSRPYARPTCCGNNNCMPIQP : 219
WP_018424152.1   : LPLSYMDQKFSDVLNAQG----------FKVVPEPVARNSRPYARPTCCGNNNCMPIQP : 219
WP_008921043.1   : LPLSYMDQKFSDVLNAQG----------FKVVPEPVARNSRPYARPTCCGNNNCMPIQP : 219
WP_013092964.1   : LPLSYMDQKFSDVLNAQG----------FKVVPEPVARNSRPYARPTCCGNNNCMPIQP : 219
WP_027195331.1   : LPLSYMDQKFSDVLNAQG----------FKVVPEPVARNSRPYARPTCCGNNNCMPIQP : 219
WP_028223852.1   : LPLSYMDQKFSDVLNANG----------FHVVPEPVARNSRPYARPTCCGNNNCMPIQP : 219
WP_027796285.1   : LPLSYMDQKFSDVLNANG----------FHVVPEPVARNSRPYARPTCCGNNNCMPIQP : 219
WP_028196142.1   : LPLSYMDQKFSDVLNAQG----------FKVVPEPVARNSRPYARPTCCGNNNCMPIQP : 219
YP_001890482     : LPLSYMDQKFSDVLNAQG----------FKVVPEPVARNSRPYARPTCCGNNNCMPIQP : 219
```

Fig. 3-5

```
                             *         260         *         280         *         300
Sequence3        : IGAMYXGIVHVEKAERAGAKLIENAVXYKXETGPDKPXVAAXYKDKTGAXXPVEGXYFVL : 283
WP_013650283.1   : IGAMYXAXTHVEKAELAGAVIXXQAVXYKLEVNXQQXXIAALXKDAXGXEXPAXGXYFVL : 283
CQJ52766.1       : IGAMYXAXTHVEKAELAGAVIXXQAVXYKLEVNXQQXXTAALXKDAXGXEXPAXGXYFVL : 283
WP_050539080.1   : IGAMYXXXTHVEKAELAGAVIXXQAVXYKLEVNXQQXXIAALXKDAXGXQXKAXGXFFVL : 288
WP_049562931.1   : IGAMYXAXTHVEKAELAGAIIXXQAVXYKLEVDXQQXXTAALXKDAXGXEHRAXGXYFVL : 283
CCV62586.1       : IGAMYXAXTHVEKAELAGAVIXXQAVXYKLEVNXQQXXIAALXKDAXGXEXPAXGXYFVL : 283
WP_005172530.1   : IGAMYXAXTHVEKAELAGAVIXXQAVXYKLEVNXQQXXIAALXKDAXGXEXPAXGXYFVL : 283
WP_011615792.1   : IGAMYXAXTHVEKAELAGAVIXXQAVXYKLEVNXQQXXIAALXKDAXGXEXPAXGXYFVL : 283
WP_050290584.1   : IGAMYXAXTHVEKAELAGAIIXXQAVXYKLEVNXQQXXIAALXKDAXGXEXPAXGXYFVL : 283
WP_004707861.1   : IGAMYSXXTHVEKAERAGAIVXXQAVXYKLEVNXQQHXTAALXKDAXGXEXPAXGQYFVL : 283
CQJ18911.1       : IGAMYXAXTHVEKAELAGAVIXXQAVXYKLEVNXQQXXIAALXKDAXGXEXPAXGXYFVL : 283
WP_049600682.1   : IGAMYXXXTHVEKAELAGAIVXXQAVXYQLEVNXQQXXTAALXKDAXGXEHRAXGQFFVL : 288
WP_049603209.1   : IGAMYXXXTVEKAELAGAIVXXQAVXYQLEVNXQQXXTAALXKDAXGXEXRVGXFFVL : 283
CFQ30984.1       : IGAMYXXXTHVEKAELAGAIVXXQAVXYQLEVNXQQXXTAALXKDAXGXEHRAXGQFFVL : 288
WP_004702484.1   : IGAMYXXXTHVEKAELAGAVIXXQAVXYQLEVNXQQXXTAALXKDAXGXEXRAXGXFFVL : 283
WP_049688140.1   : IGAMYXXXTHVEKAELAGAVIXXQAVXYQLEVNXQQXXTAALXKDAXGXEXPAXGXFFVL : 283
WP_042548059.1   : IGAMYXXXTHVEKAELAGAVIXXQAVXYQLEVNXQQXXTAALXKDAXGXEHRAXGXFFVL : 283
CRX73404.1       : IGAMYXAXTHVEKAELAGAVIXXQAVXYKLEVNXQQXXIAALXKDAXGXEXRAXGXYFVL : 283
WP_014609437.1   : IGAMYXAXTHVEKAELAGAVIXXQAVXYKLEVNXQQXXIAALXKDAXGXEXPAXGXYFVL : 283
CFQ15314.1       : IGAMYXAXTHVEKAELAGAVIXXQAVXYKLEVNXQQXXIAALXKDAXGXEXPAXGXYFVL : 283
WP_050128783.1   : IGAMYXAXTHVEKAELAGAVIXXQAVXYKLEVNXQQXXIAALXKDAXGXEXPAXGXYFVL : 283
WP_018433926.1   : IAAMYXXVIHAEKAEQAGAKLIXEAVXYRIEADXKGLXXAVHYKDPNGXSTRVTGXLFVL : 279
WP_018424152.1   : IAAMYXXVIHAEKAEQAGAKLIXEAVXYRIEADXKGLXXAVHYKDPNGXSTRVTGXLFVL : 279
WP_008921043.1   : IAAMYXXVIHAEKAEQAGAKLIXEAVXYRVEADXKGLXXAVHYKDPNGXVTRVSGXLFVL : 279
WP_013092964.1   : IAAMYXXVIHAEKAEQAGAKLIXEAVXYRIEADXKGLVXAVHYKDPNGXSTRVSGXLFVL : 279
WP_027195331.1   : IAAMYXXVIHAEKAEQAGAKLIXEAVXYRIEADXKGLXXAVHYKDPNGXSTRVTGXLFVL : 279
WP_028223852.1   : IAAMYGXXVHAEKAEHAGARLIAXAVXYRVEADNKGLXXAVHYKDPNGXSTRVTGXLFVL : 279
WP_027796285.1   : IAAMYGXVVHAEKAERAGAKLVXEAVXYRIEADNKGLXXAVHYKDPNGXSTRVTGXLFVL : 279
WP_028196142.1   : IAAMYXXVVHAEKAEQAGAKLIAEAVXYRVEADXKGLXXAVHYKDPNGXSTRVTGXLFVL : 279
YP_001890482     : IAAMYXXVVHAEKAEQAGAKLIXEAVXYRVEADNKGLXXAVHYKDPNGXSTRVTGXLFVL : 279
```

Fig. 3-6

```
                          *         320         *         340         *         360
Sequence3        : AANGIEIPKILLRSANRDFRNGRANSSDRVGRNLMDHPGTQVSEYASEKLWPGRGPQEMT : 343
WP_013650283.1   : AANGIEIPKRLRSRRKRRLGRGNSSDRVGRNLMDHPGTQVRFMANERLWPGRGPQEMT : 343
CQJ52766.1       : AANGIEIPKRLRSRRKRRLGVGNSSDRVGRNLMDHPGTQVRFMANERLWPGRGPQEMT : 343
WP_050539080.1   : AANGIEIPKRLRSREKRHGRGNSSDRVGRNLMDHPGTQVRFMASERLWPGRGPQEMT : 348
WP_049562931.1   : AANGIEIPKRLRSRRKRRLRRGNSSDRVGRNLMDHPGTQVRFMASERLWPGRGPQEMT : 343
CCV62586.1       : AANGIEIPKRLRSRRKRRLGRGNSSDRVGRNLMDHPGTQVRFMANERLWPGRGPQEMT : 343
WP_005172530.1   : AANGIEIPKRLRSRRKRRLGRGNSSDRVGRNLMDHPGTQVRFMANERLWPGRGPQEMT : 343
WP_011815792.1   : AANGIEIPKRLRSRRKRRLGRGNSSDRVGRNLMDHPGTQVRFMANERLWPGRGPQEMT : 343
WP_050290584.1   : AANGIEIPKRLRSRRKRRLGRGNSSDRVGRNLMDHPGTQVRFMASERLWPGRGPQEMT : 343
WP_004707861.1   : AANGIEIPKRLRSRRKRRPGRGNSSDRVGRNLMDHPGTQVRFMASERLWPGRGPQEMT : 343
CQJ18911.1       : AANGIEIPKRLRSRRKRRLGRGNSSDRVGRNLMDHPGTQVRFMANERLWPGRGPQEMT : 343
WP_049600682.1   : AANGIEIPKRLRSRERRRGRGNSSDRVGRNLMDHPGTQVRFMASERLWPGRGPQEMT : 348
WP_049603209.1   : AANGIEIPKRLRSRGKRRLGRGNSSDRVGRNLMDHPGTQVRFMANERLWPGRGPQEMT : 343
CFQ30984.1       : AANGIEIPKRLRSREKRRGRGNSSDRVGRNLMDHPGTQVRFMASERLWPGRGPQEMT : 348
WP_004702484.1   : AANGIEIPKRLRSRGKRRLGRGNSSDRVGRNLMDHPGTQVRFMANERLWPGRGPQEMT : 343
WP_049688140.1   : AANGIEIPKRLRSRGRRLSRGNSSDRVGRNLMDHPGTQVRFMANERLWPGRGPQEMT : 343
WP_042548059.1   : AANGIEIPKRLRSRGRRLSRGNSSDRVGRNLMDHPGTQVRFMANERLWPGRGPQEMT : 343
CRX73404.1       : AANGIEIPKRLRSRRKRRLGRGNSSDRVGRNLMDHPGTQVRFMANERLWPGRGPQEMT : 343
WP_014609437.1   : AANGIEIPKRLRSRRKRRLGRGNSSDRVGRNLMDHPGTQVRFMANERLWPGRGPQEMT : 343
CFQ15314.1       : AANGIEIPKRLRSRRKRRLGRGNSSDRVGRNLMDHPGTQVRFMANERLWPGRGPQEMT : 343
WP_050128783.1   : AANGIEIPKRLRSRRKRRLGRGNSSDRVGRNLMDHPGTQVRFMANERLWPGRGPQEMT : 343
WP_018433926.1   : AANGIEIPKRLRSRRARFRHGRNSSDQVGRNLMDHPGTQVRFLANERLWPGRGPMEMT : 339
WP_018424152.1   : AANGIEIPKRLRSRRRFRHGRNSSDQVGRNLMDHPGTQVRFLANERLWPGRGPMEMT : 339
WP_008921043.1   : AANGIEIPKRLRSRARFRHGRNSSDQVGRNLMDHPGTQVRFLANERLWPGRGPMEMT : 339
WP_013092964.1   : AANGIEIPKRLRSRARFRHGRNSSDQVGRNLMDHPGTQVRFLANERLWPGRGPMEMT : 339
WP_027195331.1   : AANGIEIPKRMLSSRRKFRHGRNSSDQVGRNLMDHPGTQVSFLANERLWPGRGPMEMT : 339
WP_028223852.1   : AANGIEIPKRIMSVRAFRHGIRNSSDQVGRNLMDHPGTQVAFLANERLWPGRGPMEMT : 339
WP_027796285.1   : AANGIEIPKRLISRRAFAHGIRNSSDQVGRNLMDHPGTQVRFLANERLWPGRGPMEMT : 339
WP_028196142.1   : AANGIEIPKRLRSRDRFRHGRNSSDQVGRNLMDHPGTQVRFLANERLWPGRGPMEMT : 339
YP_001890482     : AANGIEIPKRLRSRRDRFRHGRNSSDQVGRNLMDHPGTQVRFLANERALWPGRGPMEMT : 339
```

Fig. 3-7

```
                           *         380         *         400         *         420
Sequence3        : SLIGFRDGPFRATEAKKIHLSNGRIDDEFQKIFKA-KKMKPDEFRQIPDRSARYVQ : 402
WP_013650283.1   : SFIGFRDGFRSEYAKKIHLSNGSRDDVEILDKG-GELQIGPQDAKIRDRAARFVQ : 402
CQJ52766.1       : SLIGFRDGAFRSEYAKKIHLSNGSRDDVEILDKG-GELQIGPQDAKIRDRAARFVQ : 402
WP_050539080.1   : SMVGFRDGFFRADFAKKIHLSNGSRDDVEILDKG-GDLQIGPQEAKIRDRAARFVQ : 407
WP_049562931.1   : SLIGFRDGFFRAEYAKKIHLSNGSRDDVEILDKG-GELQIGPQDAKIRDRAARFVQ : 402
CCV62586.1       : SFIGFRDGAFRSEYAKKIHLSNGSRAEDVEILDKG-GELQIGPQDAKIPDRAARFVQ : 402
WP_005172530.1   : SLIGFRDGAFRSEYAKKIHLSNGSRDDVEILDKG-GELQIGPQDAKIRDRAARFVQ : 402
WP_011815792.1   : SLIGFRDGAFRSEYAKKIHLSNGSRDDVEILDKG-GGLQIGPQDAKIRDRAARFVQ : 402
WP_050290584.1   : SLIGFRDGAFRAEYAKKIHLSNGSRDDVEILDKG-GELQIGPQDAKIRDRAARFVQ : 402
WP_004707861.1   : SLIGFRDGAFRSEYAKKIHLSNGSRDDVEFLSK-GDEPLGPQDAKIRDRAARFVQ : 402
CQJ18911.1       : SLIGFRDGAFRSEYAKKIHLSNGSRDDVEILDKG-GELQIGPQDAKIRDRAARFVQ : 402
WP_049600682.1   : SLVGFRDGFFRADFAKKIHLSNGSRDDVEILDKG-GDLQLGPQEAKIRDRAARFVQ : 407
WP_049603209.1   : SMVGFRDGFRAEYAKKIHLSNGSRDDMAILDKG-GDLQIGPQEAKIRDRAARFVQ : 402
CFQ30984.1       : SLVGFRDGFFRADFAKKIHLSNGSRDDVEILDKG-GDLQIGPQEAKIRDRAARFVQ : 407
WP_004702484.1   : SMVGFRDGAFRAEYAKKIHLSNGSRDDMAILDKG-GDLQIGPQEAKIRDRAARFVQ : 402
WP_049688140.1   : SMVGFRDGAFRAEYAKKIHLSNGSRDDMAILDKG-GDLQIGPQEAKIRDRAARFVQ : 402
WP_042548059.1   : SMVGFRDGAFRAEYAKKIHLSNGSRDDMAILDKG-GDLQIGPQEAKIRDRAARFVQ : 402
CRX73404.1       : SFIGFRDGAFRSEYAKKIHLSNGSRDDVEILDKG-GELQIGPQDAKIRDRAARFVQ : 402
WP_014609437.1   : SFIGFRDGAFRSEYAKKIHLSNGSRDDVEILDKG-GELQIGPQDAKIRDRAARFVQ : 402
CFQ15314.1       : SFIGFRDGAFRSEYAKKIHLSNGSRDDVEILDKG-GELQIGPQDAKIRDRAARFVQ : 402
WP_050128783.1   : SFIGFRDGAFRSEYAKKIHLSNGSRDDVEILDKG-GPLQIGPQDAKIRDRAARFVQ : 402
WP_018433926.1   : SIVNFRDGAFRSDYASKKLHLSNGVPSMGSADAEK---GLTQAEFPQIRDRAARTLS : 396
WP_018424152.1   : SIVNFRDGFRSDYASKKLHLSNGVPSMGSADAEK---GLTQAEDRQIRDRAARTLN : 396
WP_008921043.1   : SIVNFRDGFRSDYASKKLHLSNGVPSLSSAGAEK---GLTQAEFDRQIRDRASKTLT : 396
WP_013092964.1   : SIVNFRDGFRSDYASKKLHLSNGVPSMGSADAEK---GLTQAEDRQIRDRAARTLS : 396
WP_027195331.1   : SIVNFRDGFRSDYASKKLHLSNGVPSMGSADAEK---GLTQAEDRQIRDRAARTLN : 396
WP_028223852.1   : SVVNFRDGFRSDYASKKLHLSNGVGSMASAAAIEN---GVTQAEDRQIPDRAARTLN : 396
WP_027796285.1   : SVVNFRDGSFRSDYASKKLHLSNGVGSMASAATQS---GLTQAEDRQIRDRAARTLN : 396
WP_028196142.1   : SIVNFRDGFRSDYASKKLHLSNGVPSMGSADAEK---GVTQAEDRQIRDRAARTLN : 396
YP_001890482     : SIVNFRDGFRSDYASKKLHLSNGVPSMSSADAEK---GLTQAEDRQIRDRAARTLN : 396
```

Fig. 3-8

```
                             *         440          *         460          *         480
Sequence3       : F  FHE L QP NR VPSK ATD  GI RPE ITY I  DYVKRGAA TRE VYAT AKVLGG : 462
WP_013650283.1  : F  FHE L  VENR  PSPT  D  GI  KPE YYAM DYVK  AV TQ  YA  AR   GG : 462
CQJ52766.1      : F  FHE L  VENP  PSPT  DS GI  KPE YYAM DYV   AV TQ  YA  AR   GG : 462
WP_050539080.1  : F  FHE L  VENR  PSST  DT GI  KPE YYAM DYVK  AV TQ  YA  AR   GG : 467
WP_049562931.1  : F  FHE L  VENR  PSPT  D  GI  KPE YYAM DYVR  AV TQ  YA  AR   GG : 462
CCV62586.1      : F  FHE L  VENR  PSPT  D  GI  KPE YYAM DYVR  AV TQ  YA  AR   GG : 462
WP_005172530.1  : F  FHE L  VENR  PSPT  D  GI  KPE YYAM DYVR  AV TQ  YA  AR   GG : 462
WP_011815792.1  : F  FHE L  VENR  PSPT  D  GI  KPE YYAM DYVR  AV TQ  YA  AR   GG : 462
WP_050290584.1  : F  FHE L  VENR  PSPT  D  GI  KPE YYAM DYVP  AV TQ  YA  AR   GG : 462
WP_004707861.1  : F  FHE L  VENR  PSA   D  GI  KPE YYAM DYVR  AV TQ  YA  AR   GG : 462
CQJ18911.1      : F  FHE L  VENR  PSPT  DS GI  KPE YYAM DYVR  AV TQ  YA  AR   GG : 462
WP_049600682.1  : F  FHE L  VENP  PSA   D  GI  KPE YYAM DYVR  AV TQ  IYA AR   GG : 467
WP_049603209.1  : F  FHE L  VENR  PSA   D  GI  KPE YYAM DYVR  AV TQ  YA  AR   GG : 462
CFQ30984.1      : F  FHE L  VENR  PSA   D  GI  KPE YYAM DYVR  AV TQ  IYA AR   GG : 467
WP_004702484.1  : F  FHE L  VENR  PSA   D  GI  KPE YYAM DYVR  AV TQ  YA  AR   GG : 462
WP_049698140.1  : F  FHE L  VENR  PSA   D  GI  KPE YYAM DYVR  AV TQ  YA  AR   GG : 462
WP_042548059.1  : F  FHE L  VENR  PSA   D  GI  KPE YYAM DYVR  AV TQ  YA  AR   GG : 462
CRX73404.1      : F  FHE L  VENR  PSPT  D  GI  KPE YYAM DYVR  AV TQ  YA  AR   GG : 462
WP_014609437.1  : F  FHE L  VENR  PSPT  D  GI  KPE YYAM DYVR  AV TQ  YA  AR   GG : 462
CFQ15314.1      : F  FHE L  VENR  PSPT  D  GI  KPE YYAM DYVR  AV TQ  YA  AR   GG : 462
WP_050126783.1  : F  FHE L  VENR  PSPT  D  GI  KPE YYAM DYVR  AV TQ  YA  AR   GG : 462
WP_018433926.1  : IN FHEH  EPQNR VPSADH D  LGI QPEI YSINDYVK  AADTHEQYAKIAA FGG : 456
WP_018424152.1  : IN FHEH  EPQNR VPSADH D  LGI QPEI YSINDYVK  AANTHELYAQIAT FGG : 456
WP_008921043.1  : IN FHEH  EPQNR VPSADH D  LGI QPEI YSINDYVK  AADTHELYARIAS FGG : 456
WP_013092964.1  : IN FHEH  EPQNR VPSADH D  LGI LPEI YSINDYVK  AADTHEQYAKIAA FGG : 456
WP_027195331.1  : IN FHEH  EPQNR VPSADH D  LGIAQPEI YSINDYVK  AANTHELYAQIAT FGG : 456
WP_028223852.1  : IN FHEH  EPQNRVLESGER D  LGI QPEI YSINDYVK  AANTHDLYAQIAQ FGG : 456
WP_027796285.1  : IN FHEH  EPQNRVLESGEH DSLGI QPEI YSINDYVK  AANTHDLYAQIAQ FGG : 456
WP_028196142.1  : IN FHEH  EPQNRVPSADH D  LGIAQPEI YSINDYVK  AANTHELYAQIAA FGG : 456
YP_001890482    : IN FHEH AEPQNRVVPSADR DSLGI QPEI YSINDYVK  AANTHELYAQIAA FGG : 456
```

Fig. 3-9

```
                              *         500         *         520         *         540
Sequence3        : DVVFNDEFAPNNHIMGSTIMGANARSVVDACRIFDHPNLFISSSATMPVGIVNVTL : 522
WP_013650283.1   : EVQFHNNFANNHIGGTTIMGNRKSVVDACRIDHKNLFIASSSMPVGSVNSTL : 522
CQJ52766.1       : EVQFHNNFANNHIGGTTIMGNRKSVVDACRIDHKNLFIASSSMPVGSVNSTL : 522
WP_050539080.1   : EVKFNNNFANNHIGGTTIMGDRKSVVDSCRIDHKNLFIASSSMPVGSVNSTL : 527
WP_049562931.1   : EVQFHNNFANNHIGGTTIMGNRKSVVDSHCRIDHKNLFIASSSMPVGSVNSTL : 522
CCV62586.1       : EVQFHNNFANNHIGGTTIMGNRKSVVDACRSIDHKNLFIASSSMPVGSVNSTL : 522
WP_005172530.1   : EVQFHNNFANNHIGGTTIMGNRKSVVDSCRSIDHKNLFIASSSMPVGSVNSTL : 522
WP_011815792.1   : EVQFHNNFANNHIGGTTIMGNRKSVVDACRIDHKNLFIASSSMPVGSVNSTL : 522
WP_050290584.1   : EVQFHNNFANNHIGGTTIMGNRKSVVDSCRIDHKNLFIASSSMPVGSVNSTL : 522
WP_004707861.1   : EVQFHNNFANNHIGGTTIMGNRKSVVDSCRIDHKNLFIASSSMPVGSVNSTL : 522
CQJ18911.1       : EVQFHNNFANNHIGGTTIMGNRKSVVDSCRIDHKNLFIASSSMPVGSVNSTL : 522
WP_049600682.1   : EVKFNNNFANNHIGGTTIMGDRKSVVDSCRSIDHKNLFIASSSMPVGSVNSTL : 527
WP_049603209.1   : EVQFHNNFANNHIGGTTIMGDRKSVVDSCRIDHKNLFIASSSMPVGSVNSTL : 522
CFQ30984.1       : EVKFNNNFANNHIGGTTIMGDRKSVVDSCRSIDHKNLFIASSSMPVGSVNSTL : 527
WP_004702484.1   : EVQFHNNFANNHIGGTTIMGDRKSVVDSCRIDHKNLFIASSSMPVGSVNSTL : 522
WP_049668140.1   : EVQFHNNFANNHIGGTTIMGDRKSVVDSCRIDHKNLFIASSSMPVGSVNSTL : 522
WP_042548059.1   : EVQFHNNFANNHIGGTTIMGDRKSVVDSCRIDHKNLFIASSSMPVGSVNSTL : 522
CRX73404.1       : EVQFHNNFANNHIGGTTIMGNRKSVVDSCRIDHKNLFIASSSMPVGSVNSTL : 522
WP_014609437.1   : EVQFHNNFANNHIGGTTIMGNRKSVVDSCRIDHKNLFIASSSMPVGSVNSTL : 522
CFQ15314.1       : EVQFHNNFANNHIGGTTIMGNRKSVVDSCRIDHKNLFIASSSMPVGSVNSTL : 522
WP_050128783.1   : EVQFHNNFANNHIGGTTIMGNRKSVVDSCRIDHKNLFIASSSMPVGSVNSTL : 522
WP_018433926.1   : VSFDDSFAPNHIMGTTIMGSAASSVVDPCRIDHANLFISGSMPSAAAVNSTL : 516
WP_018424152.1   : VSFDDSFAPNHIMGTTIMGSAASSVVDACRIDHSNLFISGSMPSAAAVNSTL : 516
WP_008921043.1   : VSFDDSFAPNHIMGTTIMGSAASSVVDACRIDHSNLFISGSMPSAAAVNSTL : 516
WP_013092964.1   : VSFDDSFAPNHIMGTTIMGSAASSVVDPCRIDHANLFISGSMPSAAAVNSTL : 516
WP_027195331.1   : VSFDDSFAPNHIMGTTIIGTAASSVVDACRIDHSNLFISASMPSAAAVNSTL : 516
WP_028223852.1   : VAFDDTFAPNHIMGTTIMGANAASVVDACRIDHSNLFISASMPSAAAVNSTL : 516
WP_027796285.1   : VSFDDTFAPNHIMGTTIMGANAASVVDACRIDHSNLFISASMPSAAAVNSTL : 516
WP_028196142.1   : AVSFDDTFAPNHIMGTTIMGSIGSVVDVCRIDHSNLFIASGSMPSAAAVNSTL : 516
YP_001890482     : AVTFDDTFAPNHIMGTTIMGSIGASVVDACRIDHSNLFISGSMPSAAAVNSTL : 516
```

Fig. 3-10

```
Sequence3        : TIAAXAXRMSDTXKXV-- : 539
WP_013650283.1   : TIAAXXRIXETXAXV-- : 539
CQJ52766.1       : TIAAXXRIXETXAXV-- : 539
WP_050539080.1   : TIAAXXRIXETXAXV-- : 544
WP_049562931.1   : TIAAXXRIXETXAXV-- : 539
CCV62586.1       : TIAAXXRIXETXAXV-- : 539
WP_005172530.1   : TIAAXXRIXETXAXV-- : 539
WP_011815792.1   : TIAAXXRIXETXAXV-- : 539
WP_050290584.1   : TIAAXXRIXETXAXV-- : 539
WP_004707861.1   : TIAAXXRIXETXAXV-- : 539
CQJ18911.1       : TIAAXXRIXETXAXV-- : 539
WP_049600682.1   : TIAAXXRIXETXAXV-- : 544
WP_049603209.1   : TIAAXXRIXETXAXV-- : 539
CFQ30984.1       : TIAAXXRIXETXAXV-- : 544
WP_004702484.1   : TIAAXXRIXETXAXV-- : 539
WP_049688140.1   : TIAAXXRIXETXAXV-- : 539
WP_042548059.1   : TIAAXXRIXETXAXV-- : 539
CRX73404.1       : TIAAXAYS--------- : 531
WP_014609437.1   : TIAAXAYR--------- : 531
CFQ15314.1       : TIAAXAYR--------- : 531
WP_050128783.1   : TIAAFXAYR--------- : 531
WP_018433926.1   : TIAAXXKLXDKXRXI-- : 533
WP_018424152.1   : TIAAXXKLGDKXRXI-- : 533
WP_008921043.1   : TIAAXXKLXDKXRXI-- : 533
WP_013092964.1   : TIAAXXKLXDRXRXI-- : 533
WP_027195331.1   : TIAAXXKLXDKXRXI-- : 533
WP_028223852.1   : TIAAXXKLXDKXRHXL-- : 533
WP_027796285.1   : TIAAXXKLXDKXRHXL-- : 533
WP_028196142.1   : TIAAXXKLXDKXRXI-- : 533
YP_001890482     : TIAAXXKLXDKXRXI-- : 533
```

MUTANT-TYPE GLUCOSE DEHYDROGENASE AND USE THEREOF

TECHNICAL FIELD

The present invention relates to a mutant-type glucose dehydrogenase (GDH) with improved substrate specificity. More specifically, the present invention relates to a GDH having a mutant α subunit. The GDH of the present invention can be suitably used for glucose sensors, glucose assay kits, and the like, and are useful in the fields of biochemistry, clinical medicine, and the like.

BACKGROUND ART

At present, a wild-type cytochrome-c-containing GDH (CyGDH) and PQQGDH which uses pyrroloquinoline quinone as a coenzyme are used for self-monitoring blood glucose sensors. However, the wild-type CyGDH and PQQGDH have a drawback in that they are incapable of accurate measurement of the blood glucose level because they react not only with glucose, but also with xylose.

JP 2012-090563 discloses a mutant GDH having low reactivity with disaccharides, wherein mutations are present at positions 326, 365, and 472 in the α-subunit. However, its low reactivity has been shown only for maltose, and mutant GDHs having decreased reactivity with xylose or galactose have not been known.

SUMMARY OF THE INVENTION

An object of the present invention is to provide a GDH having decreased reactivity with xylose, preferably with xylose and galactose, and having improved substrate specificity to glucose.

As a result of intensive study to solve the problem described above, the present inventors discovered that, by substituting, in the amino acid sequence of a GDH α-subunit of 520 to 550 amino acids containing the following peptide sequences (i) to (v) in this order, one or more of the glycine at position 10 in the peptide sequence (iii), the histidine at position 4 in the peptide sequence (iv), and the asparagine at position 4 in the peptide sequence (v) with another/other amino acid(s), reactivity with xylose and galactose can be decreased, and substrate specificity to glucose can be improved. Based on this findings, mutant GDHs useful for glucose sensors and the like were successfully obtained, thereby completed the present invention.

That is, the present invention is as follows.

<1> A mutant-type glucose dehydrogenase having glucose dehydrogenase activity and having decreased reactivity with xylose, wherein said mutant-type glucose dehydrogenase comprises a mutant-type α-subunit comprising an amino acid sequence of 520 to 550 amino acids containing the following peptide sequences (i) to (v) in this order, except that one or more amino acid residue(s) selected from the group consisting of the glycine at position 10 in the peptide sequence (iii), the histidine at position 4 in the peptide sequence (iv), and the asparagine at position 4 in the peptide sequence (v) is/are substituted with another/other amino acid(s):
(i) Val/Ile Val/Ile Val/Ile Gly Ser Gly Val Ala Gly (SEQ ID NO: 21);
(ii) Cys Cys Gly Asn Asn Asn Cys Met Pro Ile Cys (SEQ ID NO: 22);
(iii) Val Gly Arg Asn Leu Met Asp His Pro Gly Thr Gly (SEQ ID NO: 23);
(iv) Lys Lys Ile/Leu His Leu Ser Asn (SEQ ID NO: 24);
(v) Phe Ala Pro/Asn Asn Asn His Ile (SEQ ID NO: 25).

<2> The mutant-type glucose dehydrogenase according to <1>, wherein the amino acid residue(s) corresponding to at least one amino acid residue(s) selected from the group consisting of Met at position 8 in the peptide sequence (ii), Gly at position 12 in the peptide sequence (iii), Ser at position 6 in the peptide sequence (iv), Ala at position 2 in the peptide sequence (v), Pro/Asn at position 3 in the peptide sequence (v), Asn at position 5 in the peptide sequence (v), and Ile at position 7 in the peptide sequence (v) is/are substituted with another/other amino acid residue(s).

<3> The mutant-type glucose dehydrogenase according to <1> or <2>, further having decreased reactivity with galactose.

<4> The mutant-type glucose dehydrogenase according to any one of <1> to <3>, wherein said mutant-type α-subunit comprises an amino acid sequence at least 60% identical to SEQ ID NO: 3.

<5> The mutant-type glucose dehydrogenase according to any one of <1> to <3>, wherein said mutant-type α-subunit comprises an amino acid sequence at least 80% identical to an amino acid sequence selected from the group consisting of SEQ ID NO: 3 and 7-11.

<6> The mutant-type glucose dehydrogenase according to any one of <1> to <4>, wherein said mutant-type α-subunit comprises an amino acid sequence selected from the group consisting of SEQ ID NO: 3 and 7-11 except that one or several amino acids are substituted deleted, inserted, and/or added.

<7> A mutant-type glucose dehydrogenase having glucose dehydrogenase activity and having decreased reactivity with xylose, wherein said mutant-type glucose dehydrogenase comprises a mutant-type α-subunit comprising an amino acid sequence at least 60% identical to SEQ ID NO: 3, wherein the amino acid residue corresponding to the asparagine at position 474 in SEQ ID NO: 3 is substituted with serine; the amino acid residue corresponding to the glycine at position 322 in SEQ ID NO: 3 is substituted with glutamine; the amino acid residue corresponding to the histidine at position 363 in SEQ ID NO: 3 is substituted with glutamine or serine; and the amino acid residue corresponding to the asparagine at position 475 in SEQ ID NO: 3 is substituted with serine in said amino acid sequence.

<8> The mutant-type glucose dehydrogenase according to any one of <1> to <7> further comprising an electron transfer subunit.

<9> The mutant glucose-type dehydrogenase according to <8>, wherein said electron transfer subunit is cytochrome c.

<10> A DNA encoding the mutant-type glucose dehydrogenase according to any one of <1> to <9>.

<11> A recombinant vector comprising the DNA according to <10>.

<12> A microorganism transformed with the recombinant vector according to <11>.

<13> A glucose assay kit comprising the mutant glucose dehydrogenase according to any one of <1> to <9>.

<14> A glucose sensor comprising the mutant-type glucose dehydrogenase according to any one of <1> to <9>.

EFFECT OF THE INVENTION

By the present invention, GDHs having improved specificity to glucose are provided, and the GDHs can be suitably used for uses such as glucose sensors.

BRIEF DESCRIPTION OF THE DRAWINGS

FIG. 1-1 is a diagram showing an alignment of GDH sequences—Part 1.
FIG. 1-2 is a diagram showing an alignment of GDH sequences—Part 1 (continued).
FIG. 1-3 is a diagram showing an alignment of GDH sequences—Part 1 (continued).
FIG. 1-4 is a diagram showing an alignment of GDH sequences—Part 1 (continued).
FIG. 1-5 is a diagram showing an alignment of GDH sequences—Part 1 (continued).
FIG. 1-6 is a diagram showing an alignment of GDH sequences—Part 1 (continued).
FIG. 1-7 is a diagram showing an alignment of GDH sequences—Part 1 (continued).
FIG. 1-8 is a diagram showing an alignment of GDH sequences—Part 1 (continued).
FIG. 1-9 is a diagram showing an alignment of GDH sequences—Part 1 (continued).
FIG. 1-10 is a diagram showing an alignment of GDH sequences—Part 1 (continued).
FIG. 2-1 is a diagram showing an alignment of GDH sequences—Part 2.
FIG. 2-2 is a diagram showing an alignment of GDH sequences—Part 2 (continued).
FIG. 2-3 is a diagram showing an alignment of GDH sequences—Part 2 (continued).
FIG. 2-4 is a diagram showing an alignment of GDH sequences—Part 2 (continued).
FIG. 2-5 is a diagram showing an alignment of GDH sequences—Part 2 (continued).
FIG. 2-6 is a diagram showing an alignment of GDH sequences—Part 2 (continued).
FIG. 2-7 is a diagram showing an alignment of GDH sequences—Part 2 (continued).
FIG. 2-8 is a diagram showing an alignment of GDH sequences—Part 2 (continued).
FIG. 2-9 is a diagram showing an alignment of GDH sequences—Part 2 (continued).
FIG. 2-10 is a diagram showing an alignment of GDH sequences—Part 2 (continued).
FIG. 3-1 is a diagram showing an alignment of GDH sequences—Part 3.
FIG. 3-2 is a diagram showing an alignment of GDH sequences—Part 3 (continued).
FIG. 3-3 is a diagram showing an alignment of GDH sequences—Part 3 (continued).
FIG. 3-4 is a diagram showing an alignment of GDH sequences—Part 3 (continued).
FIG. 3-5 is a diagram showing an alignment of GDH sequences—Part 3 (continued).
FIG. 3-6 is a diagram showing an alignment of GDH sequences—Part 3 (continued).
FIG. 3-7 is a diagram showing an alignment of GDH sequences—Part 3 (continued).
FIG. 3-8 is a diagram showing an alignment of GDH sequences—Part 3 (continued).
FIG. 3-9 is a diagram showing an alignment of GDH sequences—Part 3 (continued).
FIG. 3-10 is a diagram showing an alignment of GDH sequences—Part 3 (continued).

EMBODIMENTS FOR CARRYING OUT THE INVENTION

The present invention is described below in detail.

The mutant-type GDH of the present invention has glucose dehydrogenase activity and has decreased reactivity with xylose and comprises a mutant-type α-subunit comprising an amino acid sequence of a GDH α-subunit of 520 to 550 amino acids containing the following peptide sequences (i) to (v) in this order, except that one or more amino acid residue(s) selected from the group consisting of the glycine at position 10 in the peptide sequence (iii), the histidine at position 4 in the peptide sequence (iv), and the asparagine at position 4 in the peptide sequence (v) is/are substituted with another/other amino acid(s):

(i)
(SEQ ID NO: 21)
Val/Ile Val/Ile Val/Ile Gly Ser Gly Val Ala Gly;

(ii)
(SEQ ID NO: 22)
Cys Cys Gly Asn Asn Asn Cys Met Pro Ile Cys;

(iii)
(SEQ ID NO: 23)
Val Gly Arg Asn Leu Met Asp His Pro Gly Thr Gly;

(iv)
(SEQ ID NO: 24)
Lys Lys Ile/Leu His Leu Ser Asn;

(v)
(SEQ ID NO: 25)
Phe Ala Pro/Asn Asn Asn His Ile.

The peptide sequences (i) to (v) are conserved among various GDH α-subunit proteins as shown in FIGS. 1-1 to 3-10, and are regions important for the GDH activity.

The sequences in FIG. 1-1 to FIG. 1-10 are as follows.
Sequence 3 SEQ ID NO: 3 (CyGDH)
WP_006396898.1 Choline dehydrogenase [*Burkholderia multivorans*]
WP_035974223.1 MULTISPECIES: Choline dehydrogenase [*Burkholderia cepacia* complex]
EGD03130.1 Glucose-methanol-choline oxidoreductase [*Burkholderia* sp. TJI49]
WP_040131619.1 Choline dehydrogenase [*Burkholderia cenocepacia*]
WP_040140036.1 Choline dehydrogenase [*Burkholderia cenocepacia*]
WP_034204694.1 Choline dehydrogenase [*Burkholderia cepacia*]
WP_044843287.1 Choline dehydrogenase [*Burkholderia* sp. USM B20]
WP_023476482.1 Glucose dehydrogenase [*Burkholderia cenocepacia*]
WP_027780833.1 Choline dehydrogenase [*Burkholderia cepacia*]
WP_011658979.1 Choline dehydrogenase [*Burkholderia ambifaria*]
WP_050012791.1 Choline dehydrogenase [*Burkholderia cenocepacia*]
WP_011547562.1 Choline dehydrogenase [*Burkholderia cenocepacia*]
WP_034202233.1 Choline dehydrogenase [*Burkholderia cepacia*]

WP_011349244.1 Choline dehydrogenase [*Burkholderia lata*]
WP_034180249.1 Choline dehydrogenase [*Burkholderia pyrrocinia*]
WP_006752014.1 Choline dehydrogenase [*Burkholderia ambifaria*]
WP_047903069.1 Choline dehydrogenase [*Burkholderia pyrrocinia*]
YP_002234347 Putative oxidoreductase [*Burkholderia cenocepacia* J2315] (SEQ ID NO: 7)
WP_039320756.1 Choline dehydrogenase [*Burkholderia* sp. A9]
WP_011882360.1 MULTISPECIES: Choline dehydrogenase [*Burkholderia*]
WP_021162033.1 MULTISPECIES: Glucose dehydrogenase [*Burkholderia*]
WP_014724779.1 MULTISPECIES: Choline dehydrogenase [*Burkholderia*]
WP_012366205.1 Choline dehydrogenase [*Burkholderia ambifaria*]
WP_046548034.1 Choline dehydrogenase [*Burkholderia contaminans*]
WP_039351161.1 Choline dehydrogenase [*Burkholderia contaminans*]
WP_027791851.1 MULTISPECIES: Choline dehydrogenase [*Burkholderia cepacia* complex]
WP_047849808.1 Choline dehydrogenase [*Burkholderia contaminans*]
WP_043184375.1 Choline dehydrogenase [*Burkholderia cepacia*]
WP_014899066.1 Choline dehydrogenase [*Burkholderia cepacia*]
WP_048252127.1 Choline dehydrogenase [*Burkholderia cepacia*]
WP_031400524.1 MULTISPECIES: Choline dehydrogenase [*Burkholderia*]
WP_010089726.1 Choline dehydrogenase [*Burkholderia ubonensis*]
WP_011354898.1 Choline dehydrogenase [*Burkholderia lata*]
WP_034187894.1 Choline dehydrogenase [*Burkholderia cenocepacia*]
WP_017329146.1 Choline dehydrogenase [*Burkholderia pyrrocinia*]
WP_045565070.1 Choline dehydrogenase [*Burkholderia ubonensis*]
WP_010804580.1 Glucose-methanol-choline oxidoreductase [*Pandoraea* sp. SD6-2]
WP_042588018.1 Choline dehydrogenase [*Burkholderia* sp. MSHR3999]
WP_038746878.1 Choline dehydrogenase [*Burkholderia pseudomallei*]
WP_010118596.1 Choline dehydrogenase [*Burkholderia oklahomensis*]
WP_010108853.1 Choline dehydrogenase [*Burkholderia oklahomensis*]
ZP_02370914 Hypothetical protein BthaT_07876 [*Burkholderia thailandensis* TXDOH] (SEQ ID NO: 8)
WP_045602806.1 Choline dehydrogenase [*Burkholderia thailandensis*]
WP_004528231.1 MULTISPECIES: Choline dehydrogenase [*Burkholderia*]
WP_009897186.1 Choline dehydrogenase [*Burkholderia thailandensis*]
WP_038763142.1 Choline dehydrogenase [*Burkholderia pseudomallei*]
WP_038781432.1 Choline dehydrogenase [*Burkholderia pseudomallei*]
WP_038778573.1 Choline dehydrogenase [*Burkholderia pseudomallei*]
WP_038779482.1 Choline dehydrogenase [*Burkholderia pseudomallei*]
WP_004198666.1 MULTISPECIES: Choline dehydrogenase [*pseudomallei* group]
WP_041195444.1 Choline dehydrogenase [*Burkholderia pseudomallei*]
WP_044490678.1 Choline dehydrogenase [*Burkholderia pseudomallei*]
WP_041189202.1 Choline dehydrogenase [*Burkholderia pseudomallei*]
WP_038789867.1 MULTISPECIES: Choline dehydrogenase [*pseudomallei* group]
WP_041198446.1 Choline dehydrogenase [*Burkholderia pseudomallei*]
KGT02773.1 FAD dependent oxidoreductase family protein [*Burkholderia pseudomallei*]
WP_015602981.1 FAD-binding protein [*Burkholderia thailandensis*]
WP_006027349.1 MULTISPECIES: Choline dehydrogenase [*Burkholderia*]
WP_027778581.1 Choline dehydrogenase [*Burkholderia caledonica*]

The sequences in FIG. 2-1 to FIG. 2-10 are as follows.
Sequence 3 SEQ ID NO: 3 (CyGDH)
WP_038789867.1 MULTISPECIES: Choline dehydrogenase [*pseudomallei* group]
WP_041198446.1 Choline dehydrogenase [*Burkholderia pseudomallei*]
KGT02773.1 FAD dependent oxidoreductase family protein [*Burkholderia pseudomallei*]
WP_015602981.1 FAD-binding protein [*Burkholderia thailandensis*]
WP_006027349.1 MULTISPECIES: Choline dehydrogenase [*Burkholderia*]
WP_027778581.1 Choline dehydrogenase [*Burkholderia caledonica*]
WP_020067867.1 Choline dehydrogenase [*Burkholderia bryophila*]
WP_027798558.1 Choline dehydrogenase [*Burkholderia dilworthii*]
WP_017774216.1 Choline dehydrogenase [*Burkholderia kururiensis*]
WP_035557405.1 Choline dehydrogenase [*Burkholderia* sp. 9120]
WP_028194543.1 MULTISPECIES: Choline dehydrogenase [*Burkholderia*]
WP_048931828.1 Choline dehydrogenase [*Ralstonia* sp. MD27]
WP_039597686.1 Choline dehydrogenase [*Ralstonia* sp. A12]
WP_021195199.1 MULTISPECIES: Choline dehydrogenase [*Ralstonia*]
WP_027677929.1 Choline dehydrogenase [*Ralstonia* sp. UNC404CL21Col]
WP_004629448.1 MULTISPECIES: Choline dehydrogenase [*Ralstonia*]
WP_024976326.1 Choline dehydrogenase [*Ralstonia pickettii*]
WP_045204558.1 Choline dehydrogenase [Burkholderiaceae bacterium 26]
ZP_02007109 FAD dependent oxidoreductase [*Ralstonia pickettii* 12D] (SEQ ID NO: 9)

WP_045786289.1 Choline dehydrogenase [*Ralstonia mannitolilytica*]
WP_009238767.1 MULTISPECIES: Choline dehydrogenase [Bacteria]
CBJ51936.1 Putative transmembrane dehydrogenase (Large subunit) oxidoreductase [*Ralstonia solanacearum* PSI07]
WP_020749404.1 Dehydrogenase (Large subunit) oxidoreductase [*Ralstonia so lanacearum*]
WP_011000725.1 Choline dehydrogenase [*Ralstonia solanacearum*]
WP_028852718.1 Choline dehydrogenase [*Ralstonia solanacearum*]
WP_016727135.1 Choline dehydrogenase [*Ralstonia solanacearum*]
WP_019717688.1 Choline dehydrogenase [*Ralstonia solanacearum*]
WP_020831435.1 2-Keto-D-gluconate dehydrogenase [*Ralstonia solanacearum*]
YP_002260434 Transmembrane dehydrogenase (large subunit) protein [Ralston ia *solanacearum* IPO1609] (SEQ ID NO: 10)
WP_003279244.1 Choline dehydrogenase [*Ralstonia solanacearum*]
WP_039568928.1 Choline dehydrogenase [*Ralstonia solanacearum*]
WP_050138572.1 Choline dehydrogenase [*Yersinia enterocolitica*]
WP_049608172.1 Choline dehydrogenase [*Yersinia pekkanenii*]
WP_050140675.1 Choline dehydrogenase [*Yersinia frederiksenii*]
WP_050101384.1 Choline dehydrogenase [*Yersinia frederiksenii*]
WP_050151802.1 Choline dehydrogenase [*Yersinia frederiksenii*]
WP_050107996.1 Choline dehydrogenase [*Yersinia frederiksenii*]
WP_050146890.1 Choline dehydrogenase [*Yersinia frederiksenii*]
WP_050135114.1 Choline dehydrogenase [*Yersinia frederiksenii*]
WP_050122940.1 Choline dehydrogenase [*Yersinia frederiksenii*]
WP_050113306.1 Choline dehydrogenase [*Yersinia kristensenii*]
WP_019081810.1 Choline dehydrogenase [*Yersinia enterocolitica*]
CQH40496.1 2-Keto-D-gluconate dehydrogenase membrane-bound flavoprotein [*Yersinia enterocolitica*]
WP_050076365.1 MULTISPECIES: Choline dehydrogenase [*Yersinia*]
CFQ84255.1 2-Keto-D-gluconate dehydrogenase membrane-bound flavoprotein [*Yersinia enterocolitica*]
CFB68626.1 2-Keto-D-gluconate dehydrogenase membrane-bound flavoprotein [*Yersinia enterocolitica*]
WP_019083704.1 Choline dehydrogenase [*Yersinia enterocolitica*]
WP_004391242.1 Choline dehydrogenase [*Yersinia kristensenii*]
WP_050130822.1 Choline dehydrogenase [*Yersinia frederiksenii*]
WP_048616917.1 MULTISPECIES: Choline dehydrogenase [*Yersinia*]
WP_050157528.1 Choline dehydrogenase [*Yersinia enterocolitica*]
CNB97617.1 2-Keto-D-gluconate dehydrogenase membrane-bound flavoprotein [*Yersinia enterocolitica*]
CRE83670.1 2-Keto-D-gluconate dehydrogenase membrane-bound flavoprotein [*Yersinia enterocolitica*]
WP_038635282.1 MULTISPECIES: Choline dehydrogenase [*Yersinia*]
CQQ92408.1 2-Keto-D-gluconate dehydrogenase membrane-bound flavoprotein [*Yersinia enterocolitica*]
WP_049679386.1 Choline dehydrogenase [*Yersinia mollaretii*]
WP_049648565.1 Choline dehydrogenase [*Yersinia mollaretii*]
WP_050159872.1 Choline dehydrogenase [*Yersinia enterocolitica*]
WP_050144494.1 Choline dehydrogenase [*Yersinia enterocolitica*]
CFR10819.1 2-Keto-D-gluconate dehydrogenase membrane-bound flavoprotein [*Yersinia frederiksenii*]
WP_050299034.1 Choline dehydrogenase [*Yersinia frederiksenii*]
WP_049610421.1 Choline dehydrogenase [*Yersinia mollaretii*]
WP_004877956.1 Choline dehydrogenase [*Yersinia mollaretii*]
WP_046050437.1 Choline dehydrogenase [*Yersinia enterocolitica*]
CFR23261.1 2-Keto-D-gluconate dehydrogenase membrane-bound flavoprotein [*Yersinia kristensenii*]

The sequences in FIG. 3-1 to FIG. 3-10 are as follows.
Sequence 3 SEQ ID NO: 3 (CyGDH)
WP_013650283.1 Choline dehydrogenase [*Yersinia enterocolitica*]
CQJ52766.1 2-Keto-D-gluconate dehydrogenase membrane-bound flavoprotein [*Yersinia enterocolitica*]
WP_050539080.1 Choline dehydrogenase [*Yersinia mollaretii*]
WP_049562931.1 Choline dehydrogenase [*Yersinia kristensenii*]
CCV62586.1 Hypothetical protein YE3094_31131 [*Yersinia enterocolitica* (type O:2) str. YE3094/96]
WP_005172530.1 Choline dehydrogenase [*Yersinia enterocolitica*]
WP_011815792.1 Choline dehydrogenase [*Yersinia enterocolitica*]
WP_050290584.1 Choline dehydrogenase [*Yersinia kristensenii*]
WP_004707861.1 Choline dehydrogenase [*Yersinia frederiksenii*]
CQJ18911.1 2-Keto-D-gluconate dehydrogenase membrane-bound flavoprotein [*Yersinia enterocolitica*]
WP_049600682.1 Choline dehydrogenase [*Yersinia bercovieri*]
WP_049603209.1 Choline dehydrogenase [*Yersinia aldovae*]
CFQ30984.1 2-Keto-D-gluconate dehydrogenase membrane-bound flavoprotein [*Yersinia enterocolitica*]
WP_004702484.1 Choline dehydrogenase [*Yersinia aldovae*]
WP_049688140.1 Choline dehydrogenase [*Yersinia aldovae*]
WP_042548059.1 Choline dehydrogenase [*Yersinia aldovae*]
CRX73404.1 2-Keto-D-gluconate dehydrogenase membrane-bound flavoprotein [*Yersinia enterocolitica*]
WP_014609437.1 Choline dehydrogenase [*Yersinia enterocolitica*]
CFQ15314.1 2-Keto-D-gluconate dehydrogenase membrane-bound flavoprotein [*Yersinia enterocolitica*]

WP_050128783.1 Choline dehydrogenase [*Yersinia enterocolitica*]
WP_018433926.1 Choline dehydrogenase [*Burkholderia* sp. JPY251]
WP_018424152.1 Choline dehydrogenase [*Burkholderia* sp. WSM4176]
WP_008921043.1 Choline dehydrogenase [*Burkholderia* sp. H160]
WP_013092964.1 Choline dehydrogenase [*Burkholderia* sp. CCGE1002]
WP_027195331.1 Choline dehydrogenase [*Burkholderia sprentiae*]
WP_028223852.1 Choline dehydrogenase [*Burkholderia ferrariae*]
WP_027796285.1 Choline dehydrogenase [*Burkholderia acidipaludis*]
WP_028196142.1 Choline dehydrogenase [*Burkholderia fungorum*]
YP_001890482 Glucose-methanol-Choline oxidoreductase [*Burkholderia phytofirmans*]

Thus, in the present invention, the sequence of GDH α-subunit before the introduction of the mutation(s) for decreasing reactivity with xylose is not limited as long as the sequence has these peptide sequences (i) to (v), has a total length of 520 to 550 (preferably 525 to 544) amino acids, and retains the GDH activity.

The sequence of GDH α-subunit before the introduction of the mutation(s) for decreasing reactivity with xylose in the present invention preferably has an identity of not less than 60% to SEQ ID NO: 3.

The "identity" may be a value calculated by using a homology search program known by those skilled in the art and can be calculated, for example, by using a parameter of default (initial setting) in the homology algorithm BLAST (Basic local alignment search tool: ncbi.nlm.nih.gov/BLAST/) in NCBI (National Center for Biotechnology Information).

SEQ ID NO: 3 is the amino acid sequence of the GDH α-subunit of *Burkholderia cepacia* KS1 strain. The KS1 strain has been deposited with the International Patent Organism Depositary, National Institute of Advanced Industrial Science and Technology (Tsukuba Central 6, 1-1-1 Higashi, Tsukuba, Ibaraki 305-8566, Japan) on Sep. 25, 2000, under Accession No. FERM BP-7306. The peptide sequences (i) to (v) correspond to the regions of amino acid positions 12-20, 212-222, 313-324, 360-366, and 471-477, respectively, in SEQ ID NO: 3.

Examples of the amino acid sequence of the GDH α-subunit having an identity of not less than 60% to SEQ ID NO: 3 include the amino acid sequences of α-subunits of a putative oxidoreductase of the *Burkholderia cenocepacia* J2315 strain (SEQ ID NO: 7), a hypothetical protein BthaT #07876 of the *Burkholderia thailandensis* TXDOH strain (SEQ ID NO: 8), a FAD-dependent oxidoreductase of the *Ralstonia pickettii* 12D strain (SEQ ID NO: 9), a transmembrane dehydrogenase of the *Ralstonia solanacearum* IPO1609 strain (SEQ ID NO: 10), and a glucose-methanol-choline oxidoreductase of the *Burkholderia phytofirmans* PsJN strain (SEQ ID NO: 11).

All amino acid sequences shown in SEQ ID NOs: 7 to 11 have been registered in a database in the National Center for Biotechnology Information (NCBI) in the United States. Their accession numbers are as follows: SEQ ID NO: 7, YP_002234347; SEQ ID NO: 8, ZP_02370914; SEQ ID NO: 9, YP_002980762; SEQ ID NO: 10, YP_002260434; and SEQ ID NO: 11, YP_001890482.

The *Burkholderia cenocepacia* J2315 strain has been deposited as LMG 16656, ATCC BAA-245, CCM 4899, CCUG 48434, and NCTC 13227. The *Burkholderia phytofirmans* PsJN strain has been deposited as LMG 22487 and CCUG 49060.

Examples of the GDH α-subunit having an identity of not less than 60% to SEQ ID NO: 3 also include the GDH α-subunits derived from JCM2800, JCM2801, JCM5506, JCM5507, and IFO14595 (SEQ ID NOs: 12 to 16), which are *Burkholderia cepacia* strains belonging to the same genus as the *Burkholderia cepacia* KS1 strain. The JCM2800, JCM2801, JCM5506, and JCM5507 have been stored in Japan Collection of Microorganisms (JCM), RIKEN. IFO14595 has been stored in Institute for Fermentation, Osaka (IFO).

The amino acid sequence shown in SEQ ID NO: 3 has amino acid sequence identities of 96%, 93%, 82%, 82%, and 63% to SEQ ID NOs: 7 to 11, respectively.

FIGS. 1-1 to 3-10 show sequence alignments of 149 GDH α-subunit sequences including these, against SEQ ID NO: 3. Among the various GDH α-subunit sequences shown in FIGS. 1-1 to 3-10, YP_001890482 has the lowest identity to SEQ ID NO: 3. It has an identity of 63% to SEQ ID NO: 3. Thus, a number of kinds of GDH α-subunits are known. Any of these has an identity of not less than 60% to SEQ ID NO: 3, and the regions described above are conserved. The mutant GDH comprising a mutant GDH α-subunit of the present invention can be obtained by substituting, in an amino acid sequence of a GDH α-subunit of 520 to 550 amino acids containing the peptide sequences (i) to (v) in this order, preferably in an amino acid sequence of 520 to 550 amino acids containing the peptide sequences (i) to (v) in this order and having an identity of not less than 60% (preferably not less than 63%) to SEQ ID NO: 3, one or more of the glycine at position 10 in the peptide sequence (iii), the histidine at position 4 in the peptide sequence (iv), and the asparagine at position 4 in the peptide sequence (v) with another/other amino acid(s).

The amino acid with which the glycine at position 10 in the peptide sequence (iii) is substituted is not limited as long as it is an amino acid other than glycine. The amino acid is preferably glutamine, histidine, methionine, asparagine, aspartic acid, cysteine, valine, leucine, alanine, isoleucine, phenylalanine, glutamic acid, serine, threonine, or arginine. Glutamine is especially preferred.

The amino acid with which the histidine at position 4 in the peptide sequence (iv) is substituted is not limited as long as it is an amino acid other than histidine. The amino acid is preferably glutamine, asparagine, arginine, or serine. Glutamine is especially preferred.

The amino acid with which the asparagine at position 4 in the peptide sequence (v) is substituted is not limited as long as it is an amino acid other than asparagine. The amino acid is preferably serine, glycine, alanine, valine, isoleucine, glutamine, methionine, tyrosine, cysteine, threonine, glutamic acid, or aspartic acid. Serine is especially preferred.

The mutant-type GDH α-subunit of the present invention has any of these three mutations. The mutant GDH α-subunit of the present invention preferably has two or more of these mutations, especially preferably has the three mutations.

The mutations are preferably the combination of substitution of the glycine at position 10 in the peptide sequence (iii) and substitution of the asparagine at position 4 in the peptide sequence (v), more preferably the combination of substitution of the glycine at position 10 in the peptide sequence (iii), substitution of the asparagine at position 4 in the peptide sequence (v), and substitution of the histidine at position 4 in the peptide sequence (iv).

The glycine at position 10 in the peptide sequence (iii) corresponds to the glycine at position 322 in SEQ ID NO: 3, the glycine at position 322 in SEQ ID NO: 7, the glycine at position 320 in SEQ ID NO: 8, the glycine at position 323 in SEQ ID NO: 9, the glycine at position 323 in SEQ ID NO: 10, and the glycine at position 318 in SEQ ID NO: 11.

The histidine at position 4 in the peptide sequence (iv) corresponds to the histidine at position 363 in SEQ ID NO: 3, the histidine at position 363 in SEQ ID NO: 7, the histidine at position 361 in SEQ ID NO: 8, the histidine at position 364 in SEQ ID NO: 9, the histidine at position 364 in SEQ ID NO: 10, and the histidine at position 359 in SEQ ID NO: 11.

The asparagine at position 4 in the peptide sequence (v) corresponds to the asparagine at position 474 in SEQ ID NO: 3, the asparagine at position 474 in SEQ ID NO: 7, the asparagine at position 472 in SEQ ID NO: 8, the asparagine at position 475 in SEQ ID NO: 9, the asparagine at position 475 in SEQ ID NO: 10, and the asparagine at position 468 in SEQ ID NO: 11.

The positions of the amino acid substitution mutations described above are those in SEQ ID NOs: 3, 7, 8, 9, 10, and 11. In homologues and variants of the GDH α-subunit whose amino acid sequences have a substitution, deletion, insertion, and/or addition of one or several amino acid residues in addition to the above particular mutation(s) in the amino acid sequences of SEQ ID NOs: 3, 7, 8, 9, 10, and 11, the above-described positions represent the corresponding positions of the amino acid substitutions in an alignment with the original amino acid sequence. For example, the methionine residue at the N-terminus is eliminated after translation in some cases. In a conservative variant of a GDH α-subunit having deletion of one amino acid residue in the region of positions 1 to 321, the position 322 represents the position 321 of the variant.

Examples of the mutant-type α-subunit of the present invention include a protein having the same amino acid sequence as the amino acid sequence of any of SEQ ID NOs: 3 and 7 to 11 except for the particular mutation(s) described above. As long as the mutant-type α-subunit has the GDH activity and decreased reactivity with xylose, it may be a protein having the same amino acid sequence as the amino acid sequence of any of SEQ ID NOs: 3 and 7 to 11 except that it has substitution, deletion, insertion, and/or addition of one or several amino acid residues in addition to the above particular mutation(s). The term "one or several" means, for example, 1 to 20, preferably 1 to 10, more preferably 1 to 5, especially preferably 1 to 3. The substitution is preferably conservative substitution. "Conservative substitution" means substitution between amino acids having similar properties, such as substitution between acidic amino acids, substitution between neutral amino acids, or substitution between basic amino acids.

The mutant-type α-subunit of the present invention is preferably a protein having an amino acid identity of at least 80%, more preferably at least 85%, further more preferably at least 90%, to the amino acid sequence of any of SEQ ID NOs: 3 and 7 to 11.

The mutant-type α-subunit of the present invention may have, in addition to the mutation(s) described above, substitution of an amino acid residue(s) corresponding to at least one amino acid residue selected from the group consisting of the methionine at position 8 in the peptide sequence (ii), the glycine at position 12 in the peptide sequence (iii), the serine at position 6 in the peptide sequence (iv), the alanine at position 2 in the peptide sequence (v), the proline or asparagine at position 3 in the peptide sequence (v), the asparagine at position 5 in the peptide sequence (v), and the isoleucine at position 7 in the peptide sequence (v), with another/other amino acid residue(s).

These amino acids correspond to the following positions in SEQ ID NO: 3.

The methionine at position 8 in the peptide sequence (ii) . . . the methionine at position 219 in SEQ ID NO: 3

The glycine at position 12 in the peptide sequence (iii) . . . the glycine at position 324 in SEQ ID NO: 3

The serine at position 6 in the peptide sequence (iv) . . . the serine at position 365 in SEQ ID NO: 3

The alanine at position 2 in the peptide sequence (v) . . . the alanine at position 472 in SEQ ID NO: 3

The proline or asparagine at position 3 in the peptide sequence (v) . . . the proline at position 473 in SEQ ID NO: 3

The asparagine at position 5 in the peptide sequence (v) . . . the asparagine at position 475 in SEQ ID NO: 3

The isoleucine at position 7 in the peptide sequence (v) . . . the isoleucine at position 477 in SEQ ID NO: 3

In addition, one or more amino acids corresponding to the following amino acids may be substituted: the methionine at position 59 in SEQ ID NO: 3, the phenylalanine at position 61 in SEQ ID NO: 3, the serine at position 326 in SEQ ID NO: 3, the glutamic acid at position 341 in SEQ ID NO: 3, the leucine at position 367 in SEQ ID NO:3, the arginine at position 369 in SEQ ID NO:3, the tyrosine at position 400 in SEQ ID NO: 3, the glutamine at position 402 in SEQ ID NO: 3, and the aspartic acid at position 404 in SEQ ID NO: 3.

The following are examples of preferred mutants.
G322Q-H363Q-N474S-N475S
G322Q-H363Q-S365A-N474S-N475S
G322Q-H363Q-S365G-N474S-N475S
G322Q-H363S-S365N-N474S-N475S
G322Q-H324Q-N474S-N475S
G322Q-H324S-N474S-N475S
G322Q-D404E-N474S-N475S
G322Q-A472M-N474S-N475S These mutation sites represent positions in SEQ ID NO: 3. For example, G322Q-H363Q-N474S-N475S represent a mutant prepared by substituting, in SEQ ID NO: 3, the glycine at position 322 to glutamine, the histidine at position 363 to glutamine, the asparagine at position 474 to serine, and the asparagine at position 475 to serine, respectively. A mutation(s) may also be introduced to an amino acid(s) other than these in SEQ ID NO: 3. Mutants prepared by introducing a mutation(s) to one or more of the same positions in other GDH sequences such as SEQ ID NOs: 7 to 11 are also included, of course, in the mutant-type GDH of the present invention.

For example, the following mutants are included in the mutant of the present invention.

A mutant-type GDH having decreased reactivity with xylose, which comprises α-subunit comprising an amino acid sequence at least 60% identical to SEQ ID NO: 3 and having glucose dehydrogenase activity, wherein the amino acid residue corresponding to the asparagine at position 474 in SEQ ID NO: 3 is substituted with serine; the amino acid residue corresponding to the glycine at position 322 in SEQ ID NO: 3 is substituted with glutamine; and the amino acid residue corresponding to the asparagine at position 475 in SEQ ID NO: 3 is substituted with serine.

A mutant-type GDH having decreased reactivity with xylose, which comprises α-subunit comprising an amino acid sequence at least 60% identical to SEQ ID NO: 3 and having glucose dehydrogenase activity, wherein the amino acid residue corresponding to the asparagine at position 474 in SEQ ID NO: 3 is substituted with serine; the amino acid residue corresponding to the glycine at position 322 in SEQ ID NO: 3 is substituted with glutamine; the amino acid residue corresponding to the histidine at position 363 in SEQ ID NO: 3 is substituted with glutamine or serine; and the amino acid residue corresponding to the asparagine at position 475 in SEQ ID NO: 3 is substituted with serine.

Since the mutant-type GDH of the present invention has the particular mutation(s) described above, it has decreased reactivity with xylose. The reactivity with xylose is, for example, not more than 50%, preferably not more than 20%, more preferably not more than 10%, relative to that of the wild-type GDH.

The "decreased reactivity with xylose" also includes cases where the reactivity with xylose relative to the reactivity with glucose is decreased. For example, the "decreased reactivity with xylose" includes cases where the substrate specificity (Xyl/Glc) described below is decreased relative to that of the wild-type GDH. The substrate specificity (Xyl/Glc) is, for example, not more than 50%, preferably not more than 20%, more preferably not more than 10%, relative to that of the wild-type GDH.

Substrate specificity=(specific activity to xylose/
specific activity to glucose)×100

Since the mutant-type GDH of the present invention has the particular mutation(s) described above, it has decreased reactivity not only with xylose, but also with galactose, as compared to the reactivities of the wild-type GDH. The reactivity with galactose is, for example, not more than 50%, preferably not more than 20%, more preferably not more than 10%, relative to that of the wild-type GDH.

The "decreased reactivity with galactose" also includes cases where the reactivity with galactose relative to the reactivity with glucose is decreased. For example, the "decreased reactivity with galactose" includes cases where the substrate specificity (Gal/Glc) described below is decreased relative to that of the wild-type GDH. The substrate specificity (Gal/Glc) is, for example, not more than 50%, preferably not more than 20%, more preferably not more than 10%, relative to that of the wild-type GDH.

Substrate specificity=specific activity to galactose/
specific activity to glucose)×100

The mutant GDH of the present invention may be an α-subunit(s) alone, or may be a complex of an α-subunit(s) and a β-subunit(s), a complex of an α-subunit(s) and a γ-subunit(s), or a complex composed of an α-subunit(s), β-subunit(s), and γ-subunit(s).

SEQ ID NO: 1 shows the nucleotide sequence of a chromosomal DNA fragment containing the GDH α-subunit gene and a part of the GDH β-subunit gene of the *Burkholderia cepacia* KS1 strain (US 2004/0023330 A). This nucleotide sequence has three open reading frames (ORFs), and the second and third ORFs from the 5'-end side encode an α-subunit (SEQ ID NO: 3) and a β-subunit (SEQ ID NO: 4), respectively. The first ORF encodes a γ-subunit (SEQ ID NO: 2). SEQ ID NO: 5 shows the nucleotide sequence of a fragment containing the full-length β-subunit gene. SEQ ID NO: 6 shows the amino acid sequence of the β-subunit (EP 1498484 A). In SEQ ID NO: 6, amino acid positions 1 to 22 correspond to a signal peptide.

In cases where the mutant GDH of the present invention contains a β-subunit, the β-subunit is not limited as long as it functions as a β-subunit, and β-subunits derived from various organisms, including those already known, may be used. More specifically, for example, a protein having the amino acid sequence corresponding to amino acid positions 23 to 425 in SEQ ID NO: 6, which is derived from the *Burkholderia cepacia* KS1 strain, may be used. As long as the subunit can function as a GDH β-subunit, it may be a protein having the same amino acid sequence as the amino acid sequence composed of amino acid positions 23 to 425 in SEQ ID NO: 6 except that one or several amino acid residues are substituted, deleted, inserted, and/or added. As long as the subunit can function as a GDH β-subunit, it may be a protein having the same amino acid sequence as the amino acid sequence of a β-subunit of a strain other than the KS1 strain except that one or several amino acid residues are substituted, deleted, inserted, and/or added. The term "one or several" means preferably 1 to 20, more preferably 1 to 10, especially preferably 1 to 5. The term "functions as a GDH β-subunit" means that, when a complex is formed together with an α-subunit(s), the β-subunit functions as an electron transfer subunit, that is, cytochrome c, without losing the GDH activity of the complex.

In cases where the mutant-type GDH of the present invention contains a γ-subunit, the γ-subunit is not limited as long as it functions as a γ-subunit, and γ-subunits derived from various organisms, including those already known, may be used. More specifically, for example, a protein having the amino acid sequence of SEQ ID NO: 2, which is derived from the *Burkholderia cepacia* KS1 strain, may be used. As long as the subunit can function as a γ-subunit, it may be a protein having the same amino acid sequence as the amino acid sequence composed of SEQ ID NO: 2 except that one or several amino acid residues are substituted, deleted, inserted, and/or added. As long as the subunit can function as a γ-subunit, it may be a protein having the same amino acid sequence as the amino acid sequence of a γ-subunit of a strain other than the KS1 strain except that one or several amino acid residues are substituted, deleted, inserted, and/or added. The term "one or several" means preferably 1 to 20, more preferably 1 to 10, especially preferably 1 to 5. The term "functions as a γ-subunit" means that, when a complex is formed together with an α-subunit(s), the γ-subunit has a function to increase the GDH activity of the complex.

The gene encoding the mutant-type GDH α-subunit of the present invention may be one having a nucleotide sequence corresponding to the amino acid sequence of the mutant-type GDH α-subunit. Specific examples of the gene include a DNA comprising the nucleotide sequence composed of nucleotides 764 to 2380 in SEQ ID NO: 1 including codon substitution corresponding to each amino acid substitution. The α-subunit gene may be a DNA which hybridizes, under stringent conditions, with a DNA comprising the nucleotide sequence composed of nucleotides 764 to 2380 in the nucleotide sequence of SEQ ID NO: 1 or a probe prepared therefrom, and which encodes a protein having the GDH activity.

Specific examples of the β-subunit gene include a DNA comprising the nucleotide sequence composed of nucleotides 187 to 1398 in SEQ ID NO: 5. The β-subunit gene may be a DNA which hybridizes, under stringent conditions, with a DNA having the nucleotide sequence composed of nucleotides 187 to 1398 in SEQ ID NO: 5, or a probe prepared therefrom, and which encodes a protein that can function as a β-subunit.

Specific examples of the γ-subunit gene include a DNA comprising the nucleotide sequence composed of nucleotides 258 to 761 in SEQ ID NO: 1. The γ-subunit gene may be a DNA which hybridizes, under stringent conditions, with a DNA having a nucleotide sequence composed of nucleotides 258 to 761 in SEQ ID NO: 1 or a probe prepared therefrom, and which encodes a protein that can function as a γ-subunit.

Examples of the stringent conditions described above include conditions that allow hybridization of DNAs having an identity of preferably 80%, more preferably not less than 90%, especially preferably not less than 95%, with each other. More specifically, for example, such conditions include washing with 0.1×SSC and 0.1% SDS at 60° C.

The α-subunit gene, β-subunit gene, and γ-subunit gene can be obtained by, for example, PCR using chromosomal DNA of the *Burkholderia cepacia* KS1 strain as a template. Primers for the PCR can be prepared by chemical synthesis based on the base sequences described above. Alternatively, those genes can be obtained from chromosomal DNA of the *Burkholderia cepacia* KS1 strain by hybridization using, as probes, oligonucleotides prepared based on the above sequences. Besides the KS1 strain, the following strains may be used: the *Burkholderia cenocepacia* J2315 strain, *Burkholderia thailandensis* TXDOH strain, *Ralstonia pickettii* 12D strain, *Ralstonia solanacearum* IPO1609 strain, and *Burkholderia phytofirmans* PsJN strain.

A GDH α-subunit having a desired mutation(s) can be obtained by introducing a nucleotide mutation(s) corresponding to the desired amino acid mutation(s) into a DNA encoding a GDH α-subunit (α-subunit gene) by site-directed mutagenesis, and allowing expression of the resulting mutant DNA using an appropriate expression system. A mutant-type CyGDH complex can be obtained by allowing expression of a DNA encoding a mutant-type GDH α-subunit in addition to a DNA encoding a β-subunit β-subunit gene), or in addition to a β-subunit gene and a DNA encoding a γ-subunit (γ-subunit gene). For the introduction of the mutation(s) into the DNA encoding a GDH α-subunit, a polycistronic DNA fragment encoding a γ-subunit, α-subunit, and β-subunit in this order may be used.

The polycistronic DNA fragment encoding a γ-subunit, α-subunit, and β-subunit in this order can be obtained by, for example, PCR using chromosomal DNA of the *Burkholderia cepacia* KS1 strain as a template, and oligonucleotides having the nucleotide sequences of SEQ ID NOs: 19 and 20 as primers.

Examples of vectors that may be used for obtaining the GDH subunit genes, introducing the mutation(s), and/or allowing expression of the genes include vectors that can function in *Escherichia* bacteria, such as pTrc99A, pBR322, pUC18, pUC118, pUC19, pUC119, pACYC184, and pBBR122. Examples of promoters that may be used for the gene expression include lac, trp, tac, trc, PL, tet, and PhoA. By inserting an α-subunit gene and/or another/other subunit gene(s) into an appropriate site(s) in an expression vector containing a promoter, insertion of the gene(s) to the vector and linking of the promoter to the gene(s) can be carried out in a single step. Examples of such an expression vector include pTrc99A, pBluescript, and pKK223-3.

Alternatively, the α-subunit gene and/or the other subunit gene(s) may be incorporated into chromosomal DNA of a host microorganism such that their expression is possible.

Examples of the method for transformation of the microorganism with the recombinant vector include the competent cell method by calcium treatment, the protoplast method, and the electroporation method.

Examples of the host microorganism include *Bacillus* bacteria such as *Bacillus subtilis*; yeasts such as *Saccharomyces cerevisiae*; and filamentous fungi such as *Aspergillus niger*. The host microorganism is not limited to these, and another host microorganism may be used as long as it is suitable for production of a foreign protein.

The substrate specificities of a GDH containing a mutant α-subunit to sugars can be determined by, for example, investigating the reactivities of the GDH with the sugars by the method described in Examples, and then comparing the observed reactivities with the reactivities of a GDH containing a wild-type α-subunit.

The GDH containing the mutant-type α-subunit of the present invention, or a microorganism expressing it, can be used as a constituent of an enzyme electrode for a glucose sensor. Examples of the glucose sensor include glucose sensors that use, as a working electrode, an enzyme electrode formed by immobilization of the GDH containing the mutant α-subunit of the present invention on a surface of an electrode such as a gold electrode, platinum electrode, or carbon electrode. The sensor means a measurement system for electrochemically measuring the concentration of a test substance of interest, and usually contains the following three electrodes: a working electrode (enzyme electrode), a counter electrode (platinum or the like), and a reference electrode (Ag/AgCl or the like). Alternatively, the sensor may be a two-electrode system constituted by a working electrode and a counter electrode, such as the ones used in conventional, simple blood glucose level systems. The sensor preferably further contains a constant-temperature cell in which a buffer and a test sample are to be placed; a power source for applying a voltage to the working electrode; an ammeter; a recorder; and/or the like. The sensor may be either a batch-type sensor or a flow-type sensor. The flow-type sensor may be a sensor which can continuously measure the blood glucose level. That is, the sensor may be one having a two-electrode system or a three-electrode system on which the enzyme of the present invention is immobilized, which electrode system is introduced into a blood sample or a dialysis sample that is continuously supplied, or into blood or interstitial fluid to perform the measurement. The structure of such an enzyme sensor is well known in the art, and described in, for example, Biosensors—Fundamental and Applications—Anthony P. F. Turner, Isao Karube, and Geroge S. Wilson, Oxford University Press 1987.

The measurement of the glucose level using the glucose sensor of the present invention can be carried out as follows. A buffer is placed in a constant-temperature cell, and the temperature of the cell is kept constant. As a working electrode, an enzyme electrode on which the mutant-type GDH of the present invention is immobilized is used. As a counter electrode, for example, a platinum electrode is used. As a reference electrode, for example, an Ag/AgCl electrode is used. A constant voltage is applied to the working electrode. After the electric current becomes constant, a sample containing glucose is placed in the constant-temperature cell, and the increase in the electric current is measured. According to a calibration curve prepared using glucose solutions having standard concentrations, the glucose concentration in the sample can be calculated.

A GDH containing the mutant-type α-subunit of the present invention can be used as a constituent of a glucose assay kit. The glucose assay kit may contain, in addition to the GDH containing the mutant-type α-subunit of the present invention, a coloring or luminescence reagent, a dilution buffer, a standard substance, manufacturer's instructions, and/or the like.

A glucose sensor and a glucose assay kit using the wild-type GDH of *Burkholderia cepacia* are described in US 2004/0023330 A. The mutant-type GDH of the present invention can be used in the same manner.

EXAMPLES

The present invention is described below more concretely by way of Examples. However, the present invention is not limited to these Examples.

Example 1

Construction of Plasmid which Expresses *Burkholderia cepacia* GDH

As a plasmid which expresses a *Burkholderia cepacia* GDH, a plasmid which expresses a GDH α-subunit and a γ-subunit was provided.

As the plasmid which expresses an α-subunit and a γ-subunit, a plasmid described in WO 02/036779 (which corresponds to EP 1331272 A), pTrc99A/γ+α was used. This plasmid is a plasmid prepared by inserting a DNA fragment consecutively containing a γ-subunit structural gene and an α-subunit structural gene of the GDH of the *Burkholderia cepacia* KS1 strain into the cloning site NcoI/HindIII of the pTrc99A vector. The GDHγα gene in this plasmid is regulated by the trc promoter. The pTrc99A/γ+α has an ampicillin resistance gene.

Using the plasmid pTrc99A/γ+α as a template, and oligonucleotides having the following sequences as primers, PCR was carried out to amplify the whole plasmid including a DNA fragment encoding six histidine residues added to the C-terminus of the GDH α-subunit.

[Forward Primer]
(SEQ ID NO: 17)
5'-ACCACCACTGATAAGGAGGTCTGACCGTGCGGAAATCTAC-3'

[Reverse Primer]
(SEQ ID NO: 18)
5'-AGCCTGTGCGACTTCTTCCTTCAGCGATCGGTGGTGGTGG-3'

Both ends of the amplified fragment were blunted, and the 5'-ends were phosphorylated, followed by circularization of the fragment by ligation. *Escherichia coli* DH5α was transformed with the obtained recombinant vector. A colony formed on LB agar medium supplemented with 50 μg/mL ampicillin was collected. The obtained transformant was cultured in liquid LB medium, and the plasmid was extracted, followed by analyzing the DNA fragment inserted therein. As a result, an inserted fragment of about 2.1 kb could be observed. The structural genes for the GDH in this plasmid are regulated by the trc promoter. This plasmid has an ampicillin resistance gene.

Example 2

Introduction of Mutations to GDH α-Subunit Gene

The GDH α-subunit gene contained in pTrc99A/γ+α, which was obtained in Example 1, was subjected to site-directed mutagenesis such that a mutation(s) was introduced to an amino acid(s) of the α-subunit encoded by the gene. More specifically, using a commercially available site-directed mutagenesis kit (QuikChange II Site-Directed Mutagenesis Kit, Stratagene), codon modification of the GDH α-subunit gene contained in the pTrc99A/γ+α plasmid described in Example 1 was carried out such that an amino acid(s), for example, the glycine at position 322, the histidine at position 363, and/or the asparagine at position 474, was/were substituted with another/other amino acid(s).

Table 1 shows the mutants constructed. In each notation representing a mutation, the number represents the position in the amino acid sequence; the alphabet before the number represents the amino acid residue before the amino acid substitution, and the alphabet after the number represents the amino acid residue after the amino acid substitution. For example, N474G represents substitution of the asparagine at position 474 with glycine.

Example 3

Analysis of Substrate Specificities of Mutant GDHs

Using the mutant GDH-expressing plasmids obtained in Example 2, mutant-type GDHs were produced, and their substrate specificities were studied.
(1) Culture Each mutant-type GDH-expressing plasmid was introduced into the *Escherichia coli* BL21 strain, and the resulting bacterial cells were cultured in 3 mL of LB medium (supplemented with 100 μg/mL carbenicillin) using an L-shaped tube at 37° C. for 4 hours, and then at 25° C. for additional 20 hours.
(2) Preparation of Crude Enzyme Sample Bacterial cells were collected from the culture liquid obtained by the culture, and suspended in 400 μL of Bug-Buster (manufactured by Merck Millipore). The resulting suspension was subjected to high-speed shaking at room temperature for 20 minutes to homogenize the bacterial cells. The suspension was centrifuged (15,000×g, 20 minutes, 4° C.), and the resulting residue was removed. The supernatant (water-soluble fraction) obtained was provided as a crude enzyme sample.
(3) Measurement of GDH Activity The enzyme activity was evaluated based on the decoloration of DCIP (2,6-dichlorophenolindophenol) caused by its reduction due to the reaction of the dehydrogenase with a substrate. The decoloration was measured by quantifying the changes in the absorbance at 600 nm with time. The reaction conditions were as follows unless otherwise specified. The reaction was started by adding a substrate (glucose, xylose, or galactose) to a reaction solution (10 mM potassium phosphate (pH 6.5)+6.0 mM PMS (methylphenazine methosulfate)+0.12 mM DCIP; all concentrations are represented as final concentrations) containing the enzyme solution, and the changes in the absorbance at 600 nm was measured. Table 1 shows the results obtained with the substrate at a final concentration of 40 mM. As a wild-type GDH, SM4γα was used.

TABLE 1

| | 40 mM Xyl/Glc % | 40 mM Gal/Glc % |
|---|---|---|
| SM4γα | 13.8 | 102.1 |
| N474G | 0.9 | 41.7 |
| N474A | 1.8 | 50.8 |
| N474V | 0.7 | 25.4 |
| N474L | 3.1 | 31.1 |
| N474I | 1.1 | 24.7 |
| N474M | 1.3 | 79.9 |
| N474F | 2.8 | 23.9 |
| N474S | 1.4 | 41.2 |

TABLE 1-continued

| | 40 mM Xyl/Glc % | 40 mM Gal/Glc % |
|---|---|---|
| N474T | 2 | 49.4 |
| N474Q | 2 | 65.2 |
| N474R | 2.5 | 55.7 |
| N474K | 3.8 | 98.5 |
| N474D | 2.9 | 77.1 |
| N474E | 5.5 | 92.9 |
| N474Y | 1.5 | 27.2 |
| N474C | 1.2 | 38.4 |
| M219A-N474V | 9.6 | 18.7 |
| M219I-N474V | 4 | 21.2 |
| M219Q-N474V | 1.3 | 26 |
| M219Q-N474F | 3.3 | 12.8 |
| M219Q-N474Y | 3.4 | 20.5 |
| G324M | 11 | 65.2 |
| G324M-N474G | 2.6 | 53.6 |
| G324M-N474A | 4.7 | 67.1 |
| G324M-N474V | 0.9 | 18.6 |
| G324M-N474Q | 4.5 | 80.1 |
| G324M-N474S | 3.5 | 50.1 |
| S365Y | 3 | 105 |
| S365Y-N474G | 1.3 | 56 |
| S365Y-N474A | 1.2 | 55.5 |
| S365Y-N474V | 2.6 | 33.8 |
| S365Y-N474S | 1.7 | 52.1 |
| S365Y-N474Q | 1.6 | 78.4 |
| A472Y | 1.3 | 75.6 |
| A472Y-N474G | 0.9 | 56.6 |
| A472Y-N474A | 0.9 | 40.3 |
| A472Y-N474V | 1.1 | 21.9 |
| A472Y-N474L | 5.1 | 27.4 |
| A472Y-N474I | 3.1 | 18.6 |
| A472Y-N474M | 0.8 | 47.5 |
| A472Y-N474P | 10.7 | 30.6 |
| A472Y-N474F | 2.4 | 14.6 |
| A472Y-N474Y | 2.8 | 26.3 |
| A472Y-N474C | 0.8 | 38.8 |
| A472Y-N474D | 1.1 | 107.2 |
| A472Y-N474E | 1.1 | 56.5 |
| A472Y-N474Q | 1 | 58.7 |
| A472Y-N474S | 1 | 47.6 |
| A472Y-N474T | 1.3 | 47.7 |
| A472Y-N474R | 3.4 | 65.5 |
| A472Y-N474H | 4.2 | 79.7 |
| A472Y-N474K | 3.1 | 110.7 |
| A472G-N474S | 3.1 | 71.8 |
| A472V-N474S | 1.4 | 54.4 |
| A472L-N474S | 1.4 | 58.9 |
| A472I-N474S | 1.4 | 60.1 |
| A472M-N474S | 1.4 | 56.5 |
| A472P-N474S | 0.9 | 53.4 |
| A472W-N474S | 0.8 | 40.2 |
| A472F-N474S | 1.5 | 65.9 |
| A472C-N474S | 0.8 | 46.5 |
| A472D-N474S | 1.3 | 58.8 |
| A472E-N474S | 1.2 | 51.9 |
| A472N-N474S | 2.3 | 70.6 |
| A472Q-N474S | 1.8 | 63.3 |
| A472S-N474S | 1.7 | 64.3 |
| A472T-N474S | 2.2 | 70.6 |
| A472K-N474S | 3.5 | 85.1 |
| A472R-N474S | 2.4 | 72.5 |
| A472H-N474S | 1.7 | 66.2 |
| S365Y-N474S-N475S | 2.9 | 48.5 |
| S365Y-A472Y-N474S | 1.3 | 43.3 |
| P473G | 7.7 | 101.8 |
| P473G-N474G | 0.9 | 49.3 |
| P473G-N474A | 1.4 | 54.3 |
| P473G-N474V | 0.8 | 9.5 |
| P473G-N474I | 1.4 | 20.9 |
| P473G-N474F | 4 | 38.7 |
| P473G-N474Q | 2.8 | 81.1 |
| P473G-N474S | 1.7 | 51.5 |
| P473G-N474E | 3.5 | 78.7 |
| N475G | 0.9 | 83.6 |
| N474G-N475G | 4.5 | 24.2 |
| N474A-N475G | 1.4 | 23.1 |
| N474V-N475G | 6.5 | 18.8 |
| N474I-N475G | 1.3 | 26.8 |
| N474Q-N475G | 1.3 | 46.9 |
| N474E-N475G | 4.9 | 75.4 |
| N474S-N475G | 1.6 | 20.9 |
| N474S-N475A | 1 | 21.4 |
| N474S-N475M | 2.9 | 26.1 |
| N474S-N475F | 2 | 24.5 |
| N474S-N475Y | 1.6 | 23.3 |
| N474S-N475C | 2.7 | 19.3 |
| N474S-N475D | 1.3 | 10.2 |
| N474S-N475E | 1.3 | 12.5 |
| N474S-N475Q | 1.4 | 23.2 |
| N474S-N475S | 0.6 | 25.1 |
| N474S-N475K | 6.5 | 28 |
| N474S-N475R | 9.9 | 40.8 |
| N474S-N475H | 1.2 | 45.2 |
| N474S-I477G | 1.6 | 60.5 |
| N474S-I477A | 1.4 | 47.5 |
| N474S-I477V | 2 | 50.7 |
| N474S-I477L | 1.4 | 51.8 |
| N474S-I477M | 2.2 | 54 |
| N474S-I477P | 1.4 | 60.2 |
| N474S-I477W | 0.8 | 33.6 |
| N474S-I477F | 0.9 | 27.8 |
| N474S-I477Y | 1.3 | 38.5 |
| N474S-I477C | 1.6 | 50.8 |
| N474S-I477D | 3.6 | 38.8 |
| N474S-I477E | 1.5 | 52.4 |
| N474S-I477N | 1.7 | 72.9 |
| N474S-I477Q | 1.2 | 41.9 |
| N474S-I477S | 1 | 38.5 |
| N474S-I477T | 1.8 | 50.1 |
| N474S-I477K | 1.7 | 55.1 |
| N474S-I477H | 1 | 38.8 |
| G322A | 8 | 88.7 |
| G322L | 2.4 | 55.7 |
| G322M | 3.2 | 59.1 |
| G322Y | 6.1 | 32.2 |
| G322C | 1.4 | 94.4 |
| G322D | 4 | 70.7 |
| G322E | 7.1 | 86.6 |
| G322N | 3.2 | 98.8 |
| G322S | 9.9 | 76.3 |
| G322T | 4.9 | 80.9 |
| G322K | 4.3 | 73.8 |
| G322R | 2.4 | 74.8 |
| G322H | 1 | 46 |
| G322M-A472Y | 2.3 | 55.3 |
| G322M-N474S | 1.9 | 36.4 |
| G322M-N475G | 4.7 | 17.1 |
| G322N-N474G | 1.7 | 68.7 |
| G322N-N474A | 2.6 | 64.7 |
| G322N-N474V | 1 | 27.5 |
| G322N-N474Q | 2.9 | 90.5 |
| G322N-N474S | 3.1 | 62 |
| G322N-S365Y | 4 | 110.3 |
| G322N-A472Y | 1.7 | 115.4 |
| G322N-A472Y-N474S | 0.9 | 34.1 |
| G322N-S365Y-A472Y | 2.1 | 89.5 |
| G322D-N474G | 1.6 | 69.5 |
| G322D-N474A | 2.4 | 73.9 |
| G322D-N474V | 1.1 | 28.9 |
| G322D-N474Q | 4.6 | 81.2 |
| G322D-N474S | 4.1 | 69.8 |
| G322H-N474S | 3 | 42.1 |
| G322H-S365Y | 2.1 | 59.3 |
| G322H-A472Y | 0.9 | 35.2 |
| G322H-A472Y-N474S | 1.6 | 36.6 |
| G322W-N474S | 0.7 | 16.6 |
| G322W-N474A | 1.5 | 19 |
| G322W-A472Y | 1.4 | 26 |
| A472G-N474S-N475S | 0.7 | 27.4 |
| A472V-N474S-N475S | 0.6 | 26.3 |
| A472L-N474S-N475S | 0.8 | 31.1 |
| A472I-N474S-N475S | 0.7 | 27.3 |
| A472P-N474S-N475S | 1.3 | 22.7 |
| A472W-N474S-N475S | 6 | 67.5 |

TABLE 1-continued

| | 40 mM Xyl/Glc % | 40 mM Gal/Glc % |
|---|---|---|
| A472F-N474S-N475S | 0.8 | 28.8 |
| A472Y-N474S-N475S | 0.6 | 28.3 |
| A472C-N474S-N475S | 0.7 | 27.1 |
| A472D-N474S-N475S | 0.7 | 30.8 |
| A472E-N474S-N475S | 1 | 38.3 |
| A472N-N474S-N475S | 0.9 | 29.8 |
| A472Q-N474S-N475S | 1.1 | 34.5 |
| A472S-N474S-N475S | 0.9 | 30.3 |
| A472T-N474S-N475S | 0.8 | 24.2 |
| A472K-N474S-N475S | 1 | 31.1 |
| A472R-N474S-N475S | 0.9 | 30.6 |
| A472H-N474S-N475S | 0.8 | 32.4 |
| G322A-N474S-N475S | 1 | 41.2 |
| G322V-N474S-N475S | 1.3 | 23.4 |
| G322L-N474S-N475S | 0.9 | 11.8 |
| G322I-N474S-N475S | 1.1 | 14.1 |
| G322M-N474S-N475S | 1.1 | 24.1 |
| G322P-N474S-N475S | 9.3 | 34.6 |
| G322W-N474S-N475S | 7.7 | 14.8 |
| G322F-N474S-N475S | 1.2 | 16.1 |
| G322Y-N474S-N475S | 3.3 | 22.4 |
| G322C-N474S-N475S | 2.8 | 19.6 |
| G322D-N474S-N475S | 1.1 | 38.8 |
| G322E-N474S-N475S | 1.2 | 24.5 |
| G322N-N474S-N475S | 0.9 | 30.4 |
| G322Q-N474S-N475S | 0.9 | 20 |
| G322S-N474S-N475S | 1 | 57.5 |
| G322T-N474S-N475S | 1.4 | 28 |
| G322R-N474S-N475S | 1.4 | 19.6 |
| G322H-N474S-N475S | 0.6 | 11.9 |
| G324A-N474S-N475S | 0.8 | 20.5 |
| G324L-N474S-N475S | 0.9 | 23.7 |
| G324I-N474S-N475S | 0.6 | 24.8 |
| G324M-N474S-N475S | 0.9 | 24.8 |
| G324P-N474S-N475S | 7.1 | 20.7 |
| G324W-N474S-N475S | 0.7 | 19.5 |
| G324F-N474S-N475S | 0.7 | 25.5 |
| G324Y-N474S-N475S | 0.7 | 18.5 |
| G324C-N474S-N475S | 0.9 | 28.6 |
| G324D-N474S-N475S | 0.9 | 24.8 |
| G324E-N474S-N475S | 0.9 | 26.5 |
| G324N-N474S-N475S | 1 | 27 |
| G324Q-N474S-N475S | 0.6 | 18.6 |
| G324S-N474S-N475S | 0.8 | 23.6 |
| G324T-N474S-N475S | 0.8 | 23 |
| G324K-N474S-N475S | 0.8 | 26.1 |
| G324R-N474S-N475S | 0.6 | 24.9 |
| G324H-N474S-N475S | 1 | 23.2 |
| G322Q-A472G-N474S-N475S | 1.1 | 21.9 |
| G322Q-A472V-N474S-N475S | 0.9 | 16 |
| G322Q-A472L-N474S-N475S | 1.1 | 20.2 |
| G322Q-A472I-N474S-N475S | 0.9 | 15 |
| G322Q-A472M-N474S-N475S | 0.9 | 19.6 |
| G322Q-A472P-N474S-N475S | 0.8 | 14.7 |
| G322Q-A472W-N474S-N475S | 1 | 21.7 |
| G322Q-A472F-N474S-N475S | 1 | 22.7 |
| G322Q-A472Y-N474S-N475S | 1 | 17.1 |
| G322Q-A472C-N474S-N475S | 0.8 | 19.5 |
| G322Q-A472D-N474S-N475S | 0.9 | 16.9 |
| G322Q-A472E-N474S-N475S | 1 | 15.5 |
| G322Q-A472Q-N474S-N475S | 1.1 | 18.7 |
| G322Q-A472S-N474S-N475S | 1.1 | 17.9 |
| G322Q-A472T-N474S-N475S | 1.2 | 16.7 |
| G322Q-A472K-N474S-N475S | 1.5 | 25.5 |
| G322Q-A472R-N474S-N475S | 1.2 | 23.9 |
| G322Q-A472H-N474S-N475S | 1.1 | 25.2 |
| 6324M-A472F-N474S-N475S | 1.2 | 29 |
| G324W-A472F-N474S-N475S | 1.1 | 25.1 |
| G322A-A472F-N474S-N475S | 1.3 | 44.3 |
| G322V-A472F-N474S-N475S | 1.2 | 20 |
| G322S-A472F-N474S-N475S | 1.1 | 43 |
| G322T-A472F-N474S-N475S | 1.1 | 21.2 |
| G322Q-S365G-N474S-N475S | 0.8 | 19.5 |
| G322Q-S365A-N474S-N475S | 0.9 | 20.4 |
| G322Q-S365V-N474S-N475S | 1.8 | 25.8 |
| G322Q-S.365L-N474S-N475S | 1.2 | 25.3 |
| G322Q-S365I-N474S-N475S | 1.1 | 20.7 |
| G322Q-S365M-N474S-N475S | 1 | 18.7 |
| G322Q-S365P-N474S-N475S | 2 | 39.8 |
| G322Q-S365F-N474S-N475S | 1.3 | 23.3 |
| G322Q-S365Y-N474S-N475S | 1.1 | 39.5 |
| G322Q-S365C-N474S-N475S | 1.3 | 22.4 |
| G322Q-S365D-N474S-N475S | 1.1 | 18.1 |
| G322Q-S365E-N474S-N475S | 3.7 | 26 |
| G322Q-S365N-N474S-N475S | 1.4 | 22.2 |
| G322Q-S365Q-N474S-N475S | 2.4 | 27.7 |
| G322Q-S365T-N474S-N475S | 1.3 | 20.6 |
| G322Q-S365K-N474S-N475S | 3.5 | 50.1 |
| G322Q-S365R-N474S-N475S | 1.9 | 32.4 |
| G322Q-S365H-N474S-N475S | 3.6 | 39.7 |
| G322A-S365Y-N474S-N475S | 0.9 | 53.3 |
| G322T-S365Y-N474S-N475S | 1.2 | 51.4 |
| G324Q-S365Y-N474S-N475S | 0.8 | 34 |
| G322Q-G324F-N474S-N475S | 0.9 | 16 |
| G322Q-G324L-N474S-N475S | 0.9 | 18.6 |
| G322Q-G324M-N474S-N475S | 0.9 | 17.6 |
| G322Q-G324D-N474S-N475S | 0.8 | 17 |
| G322Q-G324Q-N474S-N475S | 0.8 | 15.8 |
| G322Q-G324S-N474S-N475S | 0.8 | 16.5 |
| G322Q-G324R-N474S-N475S | 0.9 | 20.2 |
| G322Q-S326Q-N474S-N475S | 0.9 | 20.6 |
| G322Q-S326F-N474S-N475S | 0.9 | 20.7 |
| G322Q-H363S-N474S-N475S | 9.8 | 10.2 |
| G322Q-L367F-N474S-N475S | 1.2 | 21.8 |
| G322Q-L367S-N474S-N475S | 1.1 | 24 |
| G322Q-R369F-N474S-N475S | 0.9 | 17.1 |
| G322Q-R369S-N474S-N475S | 0.8 | 15.3 |
| G322Q-Y400F-N474S-N475S | 1.1 | 22.5 |
| G322Q-Y400S-N474S-N475S | 1.1 | 22.5 |
| G322Q-Q402F-N474S-N475S | 2.2 | 21.1 |
| G322Q-Q402S-N474S-N475S | 1 | 24.3 |
| G322Q-Q402L-N474S-N475S | 1.2 | 23.1 |
| G322Q-Q402I-N474S-N475S | 1.2 | 29.9 |
| G322Q-Q402M-N474S-N475S | 0.9 | 24.1 |
| G322Q-Q402V-N4748-N475S | 0.9 | 27.8 |
| G322Q-Q402A-N474S-N475S | 1 | 23 |
| G322Q-Q402E-N474S-N475S | 0.6 | 22.6 |
| G322Q-Q402N-N474S-N475S | 0.7 | 23.5 |
| G322Q-Q402R-N474S-N475S | 0.7 | 30 |
| G322Q-D404F-N474S-N475S | 2.9 | 24.7 |
| G322Q-D404S-N474S-N475S | 1.2 | 38.7 |
| G322Q-D404L-N474S-N475S | 1.3 | 21 |
| G322Q-D404I-N474S-N475S | 4.4 | 12.6 |
| G322Q-D404M-N474S-N475S | 0.9 | 41.9 |
| G322Q-D404V-N474S-N475S | 4.1 | 12.5 |
| G322Q-D404A-N4748-N475S | 0.9 | 37.3 |
| G322Q-D404E-N474S-N475S | 0.8 | 15.2 |
| G322Q-D404N-N474S-N475S | 0.7 | 24 |
| G322Q-D404R-N474S-N475S | 0.4 | 25.7 |
| M59F-G322Q-N474S-N475S | 1 | 20.1 |
| M59S-G322Q-N474S-N475S | 1 | 20.9 |
| F61S-G322Q-N474S-N475S | 1.1 | 16.7 |
| G322Q-E341N-S365F-N474S-N475S | 13.1 | 31.2 |
| G322Q-H363Q-S365F-N474S-N475S | 1.2 | 30.6 |
| G322Q-H363N-S365F-N474S-N475S | 2.2 | 16.5 |
| G322Q-H363S-S365F-N474S-N475S | 9.4 | 13.1 |
| G322Q-H363E-S365N-N474S-N475S | 2.9 | 8.8 |
| G322Q-H363D-S365N-N474S-N475S | 7.6 | 7.7 |
| G322Q-H363Q-S365N-N474S-N475S | 2.1 | 10.7 |
| G322Q-H363N-S365N-N474S-N475S | 3.6 | 13.7 |
| G322Q-H363R-S365N-N474S-N475S | 0.9 | 20.7 |
| G322Q-H363S-S365N-N474S-N475S | 0.9 | 19.2 |
| H363L | 6.6 | 56.4 |
| G322Q-H363Q-S365G-N474S-N475S | 1.7 | 8.9 |
| G322Q-H363Q-S365A-N474S-N475S | 1.5 | 8.8 |
| G322Q-H363Q-S365V-N474S-N475S | 4.9 | 10.1 |
| G322Q-H363Q-S365L-N474S-N475S | 3 | 6.8 |
| G322Q-H363Q-S365I-N474S-N475S | 3.9 | 9.7 |
| G322Q-H363Q-S365M-N474S-N475S | 1.6 | 8 |
| G322Q-H363Q-S365P-N474S-N475S | 2.5 | 11.9 |
| G322Q-H363Q-S365W-N474S-N475S | 3.1 | 14 |
| G322Q-H363Q-S365F-N474S-N475S | 1.9 | 12.4 |
| G322Q-H363Q-S365Y-N474S-N475S | 2.5 | 19.6 |
| G322Q-H363Q-S365C-N474S-N475S | 2.1 | 8.2 |

TABLE 1-continued

|  | 40 mM Xyl/Glc % | 40 mM Gal/Glc % |
|---|---|---|
| G322Q-H363Q-S365D-N474S-N475S | 1.8 | 9.1 |
| G322Q-H363Q-S365E-N474S-N475S | 5.3 | 10.5 |
| G322Q-H363Q-S365N-N474S-N475S | 2.2 | 10.2 |
| G322Q-H363Q-S365Q-N474S-N475S | 2.6 | 6 |
| G322Q-H363Q-S365T-N474S-N475S | 2.2 | 9.5 |
| G322Q-H363Q-S365K-N474S-N475S | 3.3 | 12.6 |
| G322Q-H363Q-S365R-N474S-N475S | 3.8 | 9 |
| G322Q-H363Q-S365H-N474S-N475S | 3.4 | 13 |

As a result, it was found that, in cases where one or more of the glycine at position 322, histidine at position 363, and asparagine at position 474 is/are substituted, the reactivity with glucose is maintained while the reactivity with xylose decreases, and that most of these mutants also show decreased reactivity with galactose.

INDUSTRIAL APPLICABILITY

The mutant-type GDH of the present invention has improved substrate specificity to glucose, and can be suitably used for measurement of glucose using a glucose sensor or the like.

While the invention has been described in detail with reference to preferred embodiments thereof, it will be apparent to one skilled in the art that various changes can be made, and equivalents employed, without departing from the scope of the invention. Each of the aforementioned documents as well as JP2015-213085 is incorporated by reference herein in its entirety.

What is claimed is:

1. A mutant glucose dehydrogenase having glucose dehydrogenase activity and decreased reactivity with xylose compared to a wild glucose dehydrogenase comprising the polypeptides of SEQ ID NO: 2, 3, and 6,
wherein said mutant glucose dehydrogenase comprises a mutant α-subunit having an amino acid sequence at least 93% identical to SEQ ID NO: 3, 7, 8, 9 or 10, wherein said mutant α-subunit comprises SEQ ID NO: 21, SEQ ID NO: 22, SEQ ID NO: 23, SEQ ID NO: 24 and SEQ ID NO: 25 in this order from N-terminus to C-terminus, except that the asparagine at position 4 in SEQ ID NO: 25 is substituted with another amino acid.

2. A mutant glucose dehydrogenase having glucose dehydrogenase activity and decreased reactivity with xylose compared to a wild glucose dehydrogenase comprising the polypeptides of SEQ ID NO: 2, 3, and 6,
wherein said mutant glucose dehydrogenase comprises a mutant α-subunit having an amino acid sequence at least 93% identical to SEQ ID NO: 3, 7, 8, 9 or 10, wherein said mutant α-subunit comprises SEQ ID NO: 21, SEQ ID NO: 22, SEQ ID NO: 23, SEQ ID NO: 24 and SEQ ID NO: 25 in this order from N-terminus to C-terminus, except that
the asparagine at position 4 in SEQ ID NO: 25 is substituted with another amino acid, and
the amino acid residue(s) corresponding to at least one amino acid residue selected from the group consisting of Met at position 8 in SEQ ID NO: 22, Gly at position 10 in SEQ ID NO: 23, Gly at position 12 in SEQ ID NO: 23, His at position 4 in SEQ ID NO: 24, Ser at position 6 in SEQ ID NO: 24, Ala at position 2 in SEQ ID NO: 25, Pro or Asn at position 3 in SEQ ID NO: 25, Asn at position 5 in SEQ ID NO: 25 and Ile at position 7 in SEQ ID NO: 25 is/are substituted with another/other amino acid residue(s).

3. The mutant glucose dehydrogenase according to claim 1, further having decreased reactivity with galactose compared to a wild-type glucose dehydrogenase comprising the polypeptides of SEQ ID NO: 2, 3 and 6.

4. The mutant type glucose dehydrogenase according to claim 1, wherein said mutant α-subunit comprises an amino acid sequence at least 96% identical to an amino acid sequence selected from the group consisting of SEQ ID NO: 3 and 7-10.

5. The mutant glucose dehydrogenase according to claim 1, wherein the mutant α-subunit comprises an amino acid sequence selected from the group consisting of SEQ ID NO: 3 and 7-10, except that the asparagine at position 4 in SEQ ID NO: 25 is substituted with another amino acid and one amino acid in SEQ ID NO: 3, 7, 8, 9, or 10 is substituted, deleted, inserted and/or added.

6. A mutant glucose dehydrogenase having glucose dehydrogenase activity and decreased reactivity with xylose compared to a wild glucose dehydrogenase comprising the polypeptides of SEQ ID NO: 2, 3, and 6,
wherein said mutant glucose dehydrogenase comprises a mutant α-subunit having an amino acid sequence at least 93% identical to SEQ ID NO: 3,
wherein the amino acid residue corresponding to the asparagine at position 474 in SEQ ID NO: 3 is substituted with serine; the amino acid residue corresponding to the glycine at position 322 in SEQ ID NO: 3 is substituted with glutamine; the amino acid residue corresponding to the histidine at position 363 in SEQ ID NO: 3 is substituted with glutamine or serine; and the amino acid residue corresponding to the asparagine at position 475 in SEQ ID NO: 3 is substituted with serine.

7. The mutant glucose dehydrogenase according to claim 1, further comprising an electron transfer subunit.

8. The mutant glucose dehydrogenase according to claim 7, wherein said electron transfer subunit is cytochrome c.

9. A glucose assay kit comprising the mutant glucose dehydrogenase according to claim 1.

10. A glucose sensor comprising the mutant glucose dehydrogenase according to claim 1.

11. The mutant glucose dehydrogenase according to claim 6, wherein said mutant α-subunit comprises the amino acid sequence of SEQ ID NO: 3, except that the amino acid residue corresponding to the asparagine at position 474 in SEQ ID NO: 3 is substituted with serine; the amino acid residue corresponding to the glycine at position 322 in SEQ ID NO: 3 is substituted with glutamine; the amino acid residue corresponding to the histidine at position 363 in SEQ ID NO: 3 is substituted with glutamine or serine; and the amino acid residue corresponding to the asparagine at position 475 in SEQ ID NO: 3 is substituted with serine.

12. A mutant glucose dehydrogenase having glucose dehydrogenase activity and decreased reactivity with xylose compared to a wild glucose dehydrogenase comprising the polypeptides of SEQ ID NO: 2, 3, and 6,
  wherein said mutant glucose dehydrogenase comprises a mutant α-subunit having an amino acid sequence at least 93% identical to SEQ ID NO: 3, 7, 8, 9 or 10, wherein said mutant α-subunit comprises SEQ ID NO: 21, SEQ ID NO: 22, SEQ ID NO: 23, SEQ ID NO: 24 and SEQ ID NO: 25 in this order from N-terminus to C-terminus, except that the glycine at position 10 in SEQ ID NO: 23, the histidine at position 4 in SEQ ID NO: 24, and the asparagine at position 4 in SEQ ID NO: 25 are substituted with other amino acids.

13. The mutant glucose dehydrogenase according to claim 12, wherein said mutant α-subunit an amino acid sequence at least 96% identical to an amino acid sequence selected from the group consisting of SEQ ID NO: 3 and 7-10.

* * * * *

SEQUENCE LISTING

```
<160> NUMBER OF SEQ ID NOS: 25

<210> SEQ ID NO 1
<211> LENGTH: 2467
<212> TYPE: DNA
<213> ORGANISM: Burkhorderia cepacia
<220> FEATURE:
<221> NAME/KEY: CDS
<222> LOCATION: (258)..(761)
<220> FEATURE:
<221> NAME/KEY: CDS
<222> LOCATION: (764)..(2380)
<220> FEATURE:
<221> NAME/KEY: CDS
<222> LOCATION: (2386)..(2466)

<400> SEQUENCE: 1
aagctttctg tttgattgca cgcgattcta accgagcgtc tgtgaggcgg aacgcgacat      60
gcttcgtgtc gcacacgtgt cgcgccgacg acacaaaaat gcagcgaaat ggctgatcgt     120
tacgaatggc tgacacattg aatggactat aaaaccattg tccgttccgg aatgtgcgcg     180
tacatttcag gtccgcgccg atttttgaga aatatcaagc gtggttttcc cgaatccggt     240
gttcgagaga aggaaac atg cac aac gac aac act ccc cac tcg cgt cgc        290
              Met His Asn Asp Asn Thr Pro His Ser Arg Arg
                1               5                   10 cac ggc gac gca gcc gca tca ggc atc acg cgg cgt caa tgg ttg caa      338
His Gly Asp Ala Ala Ala Ser Gly Ile Thr Arg Arg Gln Trp Leu Gln
            15                  20                  25 ggc gcg ctg gcg ctg acc gca gcg ggc ctc acg ggt tcg ctg aca ttg      386
Gly Ala Leu Ala Leu Thr Ala Ala Gly Leu Thr Gly Ser Leu Thr Leu
        30                  35                  40 cgg gcg ctt gca gac aac ccc ggc act gcg ccg ctc gat acg ttc atg      434
Arg Ala Leu Ala Asp Asn Pro Gly Thr Ala Pro Leu Asp Thr Phe Met
    45                  50                  55 acg ctt tcc gaa tcg ctg acc ggc aag aaa ggg ctc agc cgc gtg atc      482
Thr Leu Ser Glu Ser Leu Thr Gly Lys Lys Gly Leu Ser Arg Val Ile
60                  65                  70                  75 ggc gag cgc ctg ctg cag gcg ctg cag aag ggc tcg ttc aag acg gcc      530
Gly Glu Arg Leu Leu Gln Ala Leu Gln Lys Gly Ser Phe Lys Thr Ala
                80                  85                  90 gac agc ctg ccg cag ctc gcc ggc gcg ctc gcg tcc ggt tcg ctg acg      578
Asp Ser Leu Pro Gln Leu Ala Gly Ala Leu Ala Ser Gly Ser Leu Thr
            95                  100                 105 cct gaa cag gaa tcg ctc gca ctg acg atc ctc gag gcc tgg tat ctc      626
Pro Glu Gln Glu Ser Leu Ala Leu Thr Ile Leu Glu Ala Trp Tyr Leu
        110                 115                 120
```

| | | | | | | | | | | | | | | | | |
|---|---|---|---|---|---|---|---|---|---|---|---|---|---|---|---|---|
| ggc | atc | gtc | gac | aac | gtc | gtg | att | acg | tac | gag | gaa | gca | tta | atg | ttc | 674 |
| Gly | Ile | Val | Asp | Asn | Val | Val | Ile | Thr | Tyr | Glu | Glu | Ala | Leu | Met | Phe | |
| | 125 | | | | 130 | | | | | 135 | | | | | | |
| ggc | gtc | gtg | tcc | gat | acg | ctc | gtg | atc | cgt | tcg | tat | tgc | ccc | aac | aaa | 722 |
| Gly | Val | Val | Ser | Asp | Thr | Leu | Val | Ile | Arg | Ser | Tyr | Cys | Pro | Asn | Lys | |
| 140 | | | | | 145 | | | | | 150 | | | | | 155 | |
| ccc | ggc | ttc | tgg | gcc | gac | aaa | ccg | atc | gag | agg | caa | gcc | tg | atg | gcc | 769 |
| Pro | Gly | Phe | Trp | Ala | Asp | Lys | Pro | Ile | Glu | Arg | Gln | Ala | | Met | Ala | |
| | | | 160 | | | | | 165 | | | | | | | 170 | |
| gat | acc | gat | acg | caa | aag | gcc | gac | gtc | gtc | gtc | gtt | gga | tcg | ggt | gtc | 817 |
| Asp | Thr | Asp | Thr | Gln | Lys | Ala | Asp | Val | Val | Val | Val | Gly | Ser | Gly | Val | |
| | | | 175 | | | | | 180 | | | | | 185 | | | |
| gcg | ggc | gcg | atc | gtc | gcg | cat | cag | ctc | gcg | atg | gcg | ggc | aag | gcg | gtg | 865 |
| Ala | Gly | Ala | Ile | Val | Ala | His | Gln | Leu | Ala | Met | Ala | Gly | Lys | Ala | Val | |
| | | 190 | | | | | 195 | | | | | 200 | | | | |
| atc | ctg | ctc | gaa | gcg | ggc | ccg | cgc | atg | ccg | cgc | tgg | gaa | atc | gtc | gag | 913 |
| Ile | Leu | Leu | Glu | Ala | Gly | Pro | Arg | Met | Pro | Arg | Trp | Glu | Ile | Val | Glu | |
| | | 205 | | | | | 210 | | | | | 215 | | | | |
| cgc | ttc | cgc | aat | cag | ccc | gac | aag | atg | gac | ttc | atg | gcg | ccg | tac | ccg | 961 |
| Arg | Phe | Arg | Asn | Gln | Pro | Asp | Lys | Met | Asp | Phe | Met | Ala | Pro | Tyr | Pro | |
| | 220 | | | | | 225 | | | | | 230 | | | | | |
| tcg | agc | ccc | tgg | gcg | ccg | cat | ccc | gag | tac | ggc | ccg | ccg | aac | gac | tac | 1009 |
| Ser | Ser | Pro | Trp | Ala | Pro | His | Pro | Glu | Tyr | Gly | Pro | Pro | Asn | Asp | Tyr | |
| 235 | | | | | 240 | | | | | 245 | | | | | 250 | |
| ctg | atc | ctg | aag | ggc | gag | cac | aag | ttc | aac | tcg | cag | tac | atc | cgc | gcg | 1057 |
| Leu | Ile | Leu | Lys | Gly | Glu | His | Lys | Phe | Asn | Ser | Gln | Tyr | Ile | Arg | Ala | |
| | | | | 255 | | | | | 260 | | | | | 265 | | |
| gtg | ggc | ggc | acg | acg | tgg | cac | tgg | gcc | gcg | tcg | gcg | tgg | cgc | ttc | att | 1105 |
| Val | Gly | Gly | Thr | Thr | Trp | His | Trp | Ala | Ala | Ser | Ala | Trp | Arg | Phe | Ile | |
| | | | 270 | | | | | 275 | | | | | 280 | | | |
| ccg | aac | gac | ttc | aag | atg | aag | agc | gtg | tac | ggc | gtc | ggc | cgc | gac | tgg | 1153 |
| Pro | Asn | Asp | Phe | Lys | Met | Lys | Ser | Val | Tyr | Gly | Val | Gly | Arg | Asp | Trp | |
| | | 285 | | | | | 290 | | | | | 295 | | | | |
| ccg | atc | cag | tac | gac | gat | ctc | gag | ccg | tac | tat | cag | cgc | gcg | gag | gaa | 1201 |
| Pro | Ile | Gln | Tyr | Asp | Asp | Leu | Glu | Pro | Tyr | Tyr | Gln | Arg | Ala | Glu | Glu | |
| | 300 | | | | | 305 | | | | | 310 | | | | | |
| gag | ctc | ggc | gtg | tgg | ggc | ccg | ggc | ccc | gag | gaa | gat | ctg | tac | tcg | ccg | 1249 |
| Glu | Leu | Gly | Val | Trp | Gly | Pro | Gly | Pro | Glu | Glu | Asp | Leu | Tyr | Ser | Pro | |
| 315 | | | | | 320 | | | | | 325 | | | | | 330 | |
| cgc | aag | cag | ccg | tat | ccg | atg | ccg | ccg | ctg | ccg | ttg | tcg | ttc | aac | gag | 1297 |
| Arg | Lys | Gln | Pro | Tyr | Pro | Met | Pro | Pro | Leu | Pro | Leu | Ser | Phe | Asn | Glu | |
| | | | | 335 | | | | | 340 | | | | | 345 | | |
| cag | acc | atc | aag | acg | gcg | ctg | aac | aac | tac | gat | ccg | aag | ttc | cat | gtc | 1345 |
| Gln | Thr | Ile | Lys | Thr | Ala | Leu | Asn | Asn | Tyr | Asp | Pro | Lys | Phe | His | Val | |
| | | | 350 | | | | | 355 | | | | | 360 | | | |
| gtg | acc | gag | ccg | gtc | gcg | cgc | aac | agc | cgc | ccg | tac | gac | ggc | cgc | ccg | 1393 |
| Val | Thr | Glu | Pro | Val | Ala | Arg | Asn | Ser | Arg | Pro | Tyr | Asp | Gly | Arg | Pro | |
| | | 365 | | | | | 370 | | | | | 375 | | | | |
| act | tgt | tgc | ggc | aac | aac | aac | tgc | atg | ccg | atc | tgc | ccg | atc | ggc | gcg | 1441 |
| Thr | Cys | Cys | Gly | Asn | Asn | Asn | Cys | Met | Pro | Ile | Cys | Pro | Ile | Gly | Ala | |
| | 380 | | | | | 385 | | | | | 390 | | | | | |
| atg | tac | aac | ggc | atc | gtg | cac | gtc | gag | aag | gcc | gaa | cgc | gcc | ggc | gcg | 1489 |
| Met | Tyr | Asn | Gly | Ile | Val | His | Val | Glu | Lys | Ala | Glu | Arg | Ala | Gly | Ala | |
| 395 | | | | | 400 | | | | | 405 | | | | | 410 | |
| aag | ctg | atc | gag | aac | gcg | gtc | gtc | tac | aag | ctc | gag | acg | ggc | ccg | gac | 1537 |
| Lys | Leu | Ile | Glu | Asn | Ala | Val | Val | Tyr | Lys | Leu | Glu | Thr | Gly | Pro | Asp | |
| | | | | 415 | | | | | 420 | | | | | 425 | | |
| aag | cgc | atc | gtc | gcg | gcg | ctc | tac | aag | gac | aag | acg | ggc | gcc | gag | cat | 1585 |
| Lys | Arg | Ile | Val | Ala | Ala | Leu | Tyr | Lys | Asp | Lys | Thr | Gly | Ala | Glu | His | |
| | | | 430 | | | | | 435 | | | | | 440 | | | |

| | |
|---|---|
| cgc gtc gaa ggc aag tat ttc gtg ctc gcc gcg aac ggc atc gag acg<br>Arg Val Glu Gly Lys Tyr Phe Val Leu Ala Ala Asn Gly Ile Glu Thr<br>445 450 455 | 1633 |
| ccg aag atc ctg ctg atg tcc gcg aac cgc gat ttc ccg aac ggt gtc<br>Pro Lys Ile Leu Leu Met Ser Ala Asn Arg Asp Phe Pro Asn Gly Val<br>460 465 470 | 1681 |
| gcg aac agc tcg gac atg gtc ggc cgc aac ctg atg gac cat ccg ggc<br>Ala Asn Ser Ser Asp Met Val Gly Arg Asn Leu Met Asp His Pro Gly<br>475 480 485 490 | 1729 |
| acc ggc gtg tcg ttc tat gcg agc gag aag ctg tgg ccg ggc cgc ggc<br>Thr Gly Val Ser Phe Tyr Ala Ser Glu Lys Leu Trp Pro Gly Arg Gly<br>495 500 505 | 1777 |
| ccg cag gag atg acg tcg ctg atc ggt ttc cgc gac ggt ccg ttc cgc<br>Pro Gln Glu Met Thr Ser Leu Ile Gly Phe Arg Asp Gly Pro Phe Arg<br>510 515 520 | 1825 |
| gcg acc gaa gcg gcg aag aag atc cac ctg tcg aac ctg tcg cgc atc<br>Ala Thr Glu Ala Ala Lys Lys Ile His Leu Ser Asn Leu Ser Arg Ile<br>525 530 535 | 1873 |
| gac cag gag acg cag aag atc ttc aag gcc ggc aag ctg atg aag ccc<br>Asp Gln Glu Thr Gln Lys Ile Phe Lys Ala Gly Lys Leu Met Lys Pro<br>540 545 550 | 1921 |
| gac gag ctc gac gcg cag atc cgc gac cgt tcc gca cgc tac gtg cag<br>Asp Glu Leu Asp Ala Gln Ile Arg Asp Arg Ser Ala Arg Tyr Val Gln<br>555 560 565 570 | 1969 |
| ttc gac tgc ttc cac gaa atc ctg ccg caa ccc gag aac cgc atc gtg<br>Phe Asp Cys Phe His Glu Ile Leu Pro Gln Pro Glu Asn Arg Ile Val<br>575 580 585 | 2017 |
| ccg agc aag acg gcg acc gat gcg atc ggc att ccg cgc ccc gag atc<br>Pro Ser Lys Thr Ala Thr Asp Ala Ile Gly Ile Pro Arg Pro Glu Ile<br>590 595 600 | 2065 |
| acg tat gcg atc gac gac tac gtg aag cgc ggc gcc gcg cat acg cgc<br>Thr Tyr Ala Ile Asp Asp Tyr Val Lys Arg Gly Ala Ala His Thr Arg<br>605 610 615 | 2113 |
| gag gtc tac gcg acc gcc gcg aag gtg ctc ggc ggc acg gac gtc gtg<br>Glu Val Tyr Ala Thr Ala Ala Lys Val Leu Gly Gly Thr Asp Val Val<br>620 625 630 | 2161 |
| ttc aac gac gaa ttc gcg ccg aac aat cac atc acg ggc tcg acg atc<br>Phe Asn Asp Glu Phe Ala Pro Asn Asn His Ile Thr Gly Ser Thr Ile<br>635 640 645 650 | 2209 |
| atg ggc gcc gat gcg cgc gac tcc gtc gtc gac aag gac tgc cgc acg<br>Met Gly Ala Asp Ala Arg Asp Ser Val Val Asp Lys Asp Cys Arg Thr<br>655 660 665 | 2257 |
| ttc gac cat ccg aac ctg ttc att tcg agc agc gcg acg atg ccg acc<br>Phe Asp His Pro Asn Leu Phe Ile Ser Ser Ser Ala Thr Met Pro Thr<br>670 675 680 | 2305 |
| gtc ggt acc gta aac gtg acg ctg acg atc gcc gcg ctc gcg ctg cgg<br>Val Gly Thr Val Asn Val Thr Leu Thr Ile Ala Ala Leu Ala Leu Arg<br>685 690 695 | 2353 |
| atg tcg gac acg ctg aag aag gaa gtc tgacc gtg cgg aaa tct act ctc<br>Met Ser Asp Thr Leu Lys Lys Glu Val     Val Arg Lys Ser Thr Leu<br>700 705 710 | 2403 |
| act ttc ctc atc gcc ggc tgc ctc gcg ttg ccg ggc ttc gcg cgc gcg<br>Thr Phe Leu Ile Ala Gly Cys Leu Ala Leu Pro Gly Phe Ala Arg Ala<br>715 720 725 | 2451 |
| gcc gat gcg gcc gat c<br>Ala Asp Ala Ala Asp<br>730 | 2467 |

-continued

```
<210> SEQ ID NO 2
<211> LENGTH: 168
<212> TYPE: PRT
<213> ORGANISM: Burkhorderia cepacia

<400> SEQUENCE: 2

Met His Asn Asp Asn Thr Pro His Ser Arg Arg His Gly Asp Ala Ala
1               5                   10                  15

Ala Ser Gly Ile Thr Arg Arg Gln Trp Leu Gln Gly Ala Leu Ala Leu
            20                  25                  30

Thr Ala Ala Gly Leu Thr Gly Ser Leu Thr Leu Arg Ala Leu Ala Asp
        35                  40                  45

Asn Pro Gly Thr Ala Pro Leu Asp Thr Phe Met Thr Leu Ser Glu Ser
    50                  55                  60

Leu Thr Gly Lys Lys Gly Leu Ser Arg Val Ile Gly Glu Arg Leu Leu
65                  70                  75                  80

Gln Ala Leu Gln Lys Gly Ser Phe Lys Thr Ala Asp Ser Leu Pro Gln
                85                  90                  95

Leu Ala Gly Ala Leu Ala Ser Gly Ser Leu Thr Pro Glu Gln Glu Ser
            100                 105                 110

Leu Ala Leu Thr Ile Leu Glu Ala Trp Tyr Leu Gly Ile Val Asp Asn
        115                 120                 125

Val Val Ile Thr Tyr Glu Glu Ala Leu Met Phe Gly Val Val Ser Asp
    130                 135                 140

Thr Leu Val Ile Arg Ser Tyr Cys Pro Asn Lys Pro Gly Phe Trp Ala
145                 150                 155                 160

Asp Lys Pro Ile Glu Arg Gln Ala
                165

<210> SEQ ID NO 3
<211> LENGTH: 539
<212> TYPE: PRT
<213> ORGANISM: Burkhorderia cepacia

<400> SEQUENCE: 3

Met Ala Asp Thr Asp Thr Gln Lys Ala Asp Val Val Val Val Gly Ser
1               5                   10                  15

Gly Val Ala Gly Ala Ile Val Ala His Gln Leu Ala Met Ala Gly Lys
            20                  25                  30

Ala Val Ile Leu Leu Glu Ala Gly Pro Arg Met Pro Arg Trp Glu Ile
        35                  40                  45

Val Glu Arg Phe Arg Asn Gln Pro Asp Lys Met Asp Phe Met Ala Pro
    50                  55                  60

Tyr Pro Ser Ser Pro Trp Ala Pro His Pro Glu Tyr Gly Pro Pro Asn
65                  70                  75                  80

Asp Tyr Leu Ile Leu Lys Gly Glu His Lys Phe Asn Ser Gln Tyr Ile
                85                  90                  95

Arg Ala Val Gly Gly Thr Thr Trp His Trp Ala Ala Ser Ala Trp Arg
            100                 105                 110

Phe Ile Pro Asn Asp Phe Lys Met Lys Ser Val Tyr Gly Val Gly Arg
        115                 120                 125

Asp Trp Pro Ile Gln Tyr Asp Asp Leu Glu Pro Tyr Tyr Gln Arg Ala
    130                 135                 140

Glu Glu Glu Leu Gly Val Trp Gly Pro Gly Pro Glu Glu Asp Leu Tyr
145                 150                 155                 160
```

```
Ser Pro Arg Lys Gln Pro Tyr Pro Met Pro Pro Leu Pro Leu Ser Phe
                165                 170                 175
Asn Glu Gln Thr Ile Lys Thr Ala Leu Asn Asn Tyr Asp Pro Lys Phe
            180                 185                 190
His Val Thr Glu Pro Val Ala Arg Asn Ser Arg Pro Tyr Asp Gly
        195                 200                 205
Arg Pro Thr Cys Cys Gly Asn Asn Cys Met Pro Ile Cys Pro Ile
    210                 215                 220
Gly Ala Met Tyr Asn Gly Ile Val His Val Lys Ala Glu Arg Ala
225                 230                 235                 240
Gly Ala Lys Leu Ile Glu Asn Ala Val Val Tyr Lys Leu Glu Thr Gly
                245                 250                 255
Pro Asp Lys Arg Ile Val Ala Ala Leu Tyr Lys Asp Lys Thr Gly Ala
                260                 265                 270
Glu His Arg Val Glu Gly Lys Tyr Phe Val Leu Ala Ala Asn Gly Ile
            275                 280                 285
Glu Thr Pro Lys Ile Leu Leu Met Ser Ala Asn Arg Asp Phe Pro Asn
        290                 295                 300
Gly Val Ala Asn Ser Ser Asp Met Val Gly Arg Asn Leu Met Asp His
305                 310                 315                 320
Pro Gly Thr Gly Val Ser Phe Tyr Ala Ser Glu Lys Leu Trp Pro Gly
                325                 330                 335
Arg Gly Pro Gln Glu Met Thr Ser Leu Ile Gly Phe Arg Asp Gly Pro
                340                 345                 350
Phe Arg Ala Thr Glu Ala Ala Lys Lys Ile His Leu Ser Asn Leu Ser
            355                 360                 365
Arg Ile Asp Gln Glu Thr Gln Lys Ile Phe Lys Ala Gly Lys Leu Met
        370                 375                 380
Lys Pro Asp Glu Leu Asp Ala Gln Ile Arg Asp Arg Ser Ala Arg Tyr
385                 390                 395                 400
Val Gln Phe Asp Cys Phe His Glu Ile Leu Pro Gln Pro Glu Asn Arg
                405                 410                 415
Ile Val Pro Ser Lys Thr Ala Thr Asp Ala Ile Gly Ile Pro Arg Pro
                420                 425                 430
Glu Ile Thr Tyr Ala Ile Asp Asp Tyr Val Lys Arg Gly Ala Ala His
            435                 440                 445
Thr Arg Glu Val Tyr Ala Thr Ala Ala Lys Val Leu Gly Gly Thr Asp
        450                 455                 460
Val Val Phe Asn Asp Glu Phe Ala Pro Asn Asn His Ile Thr Gly Ser
465                 470                 475                 480
Thr Ile Met Gly Ala Asp Ala Arg Asp Ser Val Val Asp Lys Asp Cys
                485                 490                 495
Arg Thr Phe Asp His Pro Asn Leu Phe Ile Ser Ser Ser Ala Thr Met
                500                 505                 510
Pro Thr Val Gly Thr Val Asn Val Thr Leu Thr Ile Ala Ala Leu Ala
            515                 520                 525
Leu Arg Met Ser Asp Thr Leu Lys Lys Glu Val
        530                 535

<210> SEQ ID NO 4
<211> LENGTH: 27
<212> TYPE: PRT
<213> ORGANISM: Burkhorderia cepacia
```

-continued

```
<400> SEQUENCE: 4

Val Arg Lys Ser Thr Leu Thr Phe Leu Ile Ala Gly Cys Leu Ala Leu
1               5                   10                  15

Pro Gly Phe Ala Arg Ala Ala Asp Ala Ala Asp
            20                  25

<210> SEQ ID NO 5
<211> LENGTH: 1441
<212> TYPE: DNA
<213> ORGANISM: Burkholderia cepacia
<220> FEATURE:
<221> NAME/KEY: CDS
<222> LOCATION: (121)..(1398)

<400> SEQUENCE: 5
tccgaacctg ttcatttcga gcagcgcgac gatgccgacc gtcggtaccg taaacgtgac      60
gctgacgatc gccgcgctcg cgctgcggat gtcggacacg ctgaagaagg aagtctgacc    120 gtg cgg aaa tct act ctc act ttc ctc atc gcc ggc tgc ctc gcg ttg      168
Val Arg Lys Ser Thr Leu Thr Phe Leu Ile Ala Gly Cys Leu Ala Leu
 1               5                  10                  15 ccg ggc ttc gcg cgc gcg gcc gat gcg gcc gat ccg gcg ctg gtc aag      216
Pro Gly Phe Ala Arg Ala Ala Asp Ala Ala Asp Pro Ala Leu Val Lys
             20                  25                  30 cgc ggc gaa tac ctc gcg acc gcc ggc gac tgc atg gcc tgc cac acc      264
Arg Gly Glu Tyr Leu Ala Thr Ala Gly Asp Cys Met Ala Cys His Thr
         35                  40                  45 gtg aag ggc ggc aag ccg tac gcg ggc ggc ctt ggc atg ccg gta ccg      312
Val Lys Gly Gly Lys Pro Tyr Ala Gly Gly Leu Gly Met Pro Val Pro
     50                  55                  60 atg ctc ggc aag atc tac acg agc aac atc acg ccc gat ccc gat acg      360
Met Leu Gly Lys Ile Tyr Thr Ser Asn Ile Thr Pro Asp Pro Asp Thr
 65                  70                  75                  80 ggc atc ggc aaa tgg acg ttc gag gac ttc gag cgc gcg gtg cgg cac      408
Gly Ile Gly Lys Trp Thr Phe Glu Asp Phe Glu Arg Ala Val Arg His
                 85                  90                  95 ggc gtg tcg aag aac ggc gac aac ctg tat ccg gcg atg ccg tac gtg      456
Gly Val Ser Lys Asn Gly Asp Asn Leu Tyr Pro Ala Met Pro Tyr Val
            100                 105                 110 tcg tac gcg aag atc acg gac gac gac gta cgc gcg ctg tac gcc tac      504
Ser Tyr Ala Lys Ile Thr Asp Asp Asp Val Arg Ala Leu Tyr Ala Tyr
        115                 120                 125 ttc atg cac ggc gtc gag ccg gtc aag cag gcg ccg ccg aag aac gag      552
Phe Met His Gly Val Glu Pro Val Lys Gln Ala Pro Pro Lys Asn Glu
    130                 135                 140 att ccc gcg ctg ctc agc atg cgc tgg ccg ctg aag atc tgg aac tgg      600
Ile Pro Ala Leu Leu Ser Met Arg Trp Pro Leu Lys Ile Trp Asn Trp
145                 150                 155                 160 ctg ttc ctg aag gac ggc ccg tac cag ccg aag ccg tcg cag agc gcc      648
Leu Phe Leu Lys Asp Gly Pro Tyr Gln Pro Lys Pro Ser Gln Ser Ala
                165                 170                 175 gaa tgg aat cgc ggc gcg tat ctg gtg cag ggt ctc gcg cac tgc agc      696
Glu Trp Asn Arg Gly Ala Tyr Leu Val Gln Gly Leu Ala His Cys Ser
            180                 185                 190 acg tgc cac acg ccg cgc ggc atc gcg atg cag gag aag tcg ctc gac      744
Thr Cys His Thr Pro Arg Gly Ile Ala Met Gln Glu Lys Ser Leu Asp
        195                 200                 205 gaa acc ggc ggc agc ttc ctc gcg ggg tcg gtg ctc gcc ggc tgg gac      792
Glu Thr Gly Gly Ser Phe Leu Ala Gly Ser Val Leu Ala Gly Trp Asp
    210                 215                 220
```

```
ggc tac aac atc acg tcg gac ccg aat gcg ggg atc ggc agc tgg acg        840
Gly Tyr Asn Ile Thr Ser Asp Pro Asn Ala Gly Ile Gly Ser Trp Thr
225                 230                 235                 240 cag cag cag ctc gtg cag tat ttg cgc acc ggc agc gtg ccg ggc gtc        888
Gln Gln Gln Leu Val Gln Tyr Leu Arg Thr Gly Ser Val Pro Gly Val
                245                 250                 255 gcg cag gcg gcc ggg ccg atg gcc gag gcg gtc gag cac agc ttc tcg        936
Ala Gln Ala Ala Gly Pro Met Ala Glu Ala Val Glu His Ser Phe Ser
            260                 265                 270 aag atg acc gaa gcg gac atc ggt gcg atc gcc acg tac gtc cgc acg        984
Lys Met Thr Glu Ala Asp Ile Gly Ala Ile Ala Thr Tyr Val Arg Thr
        275                 280                 285 gtg ccg gcc gtt gcc gac agc aac gcg aag cag ccg cgg tcg tcg tgg       1032
Val Pro Ala Val Ala Asp Ser Asn Ala Lys Gln Pro Arg Ser Ser Trp
    290                 295                 300 ggc aag ccg gcc gag gac ggg ctg aag ctg cgc ggt gtc gcg ctc gcg       1080
Gly Lys Pro Ala Glu Asp Gly Leu Lys Leu Arg Gly Val Ala Leu Ala
305                 310                 315                 320 tcg tcg ggc atc gat ccg gcg cgg ctg tat ctc ggc aac tgc gcg acg       1128
Ser Ser Gly Ile Asp Pro Ala Arg Leu Tyr Leu Gly Asn Cys Ala Thr
                325                 330                 335 tgc cac cag atg cag ggc aag ggc acg ccg gac ggc tat tac ccg tcg       1176
Cys His Gln Met Gln Gly Lys Gly Thr Pro Asp Gly Tyr Tyr Pro Ser
                340                 345                 350 ctg ttc cac aac tcc acc gtc ggc gcg tcg aat ccg tcg aac ctc gtg       1224
Leu Phe His Asn Ser Thr Val Gly Ala Ser Asn Pro Ser Asn Leu Val
            355                 360                 365 cag gtg atc ctg aac ggc gtg cag cgc aag atc ggc agc gag gat atc       1272
Gln Val Ile Leu Asn Gly Val Gln Arg Lys Ile Gly Ser Glu Asp Ile
        370                 375                 380 ggg atg ccc gct ttc cgc tac gat ctg aac gac gcg cag atc gcc gcg       1320
Gly Met Pro Ala Phe Arg Tyr Asp Leu Asn Asp Ala Gln Ile Ala Ala
385                 390                 395                 400 ctg acg aac tac gtg acc gcg cag ttc ggc aat ccg gcg gcg aag gtg       1368
Leu Thr Asn Tyr Val Thr Ala Gln Phe Gly Asn Pro Ala Ala Lys Val
                405                 410                 415 acg gag cag gac gtc gcg aag ctg cgc tga catagtcggg cgcgccgaca         1418
Thr Glu Gln Asp Val Ala Lys Leu Arg
                420                 425 cggcgcaacc gataggacag gag                                             1441

<210> SEQ ID NO 6
<211> LENGTH: 425
<212> TYPE: PRT
<213> ORGANISM: Burkholderia cepacia

<400> SEQUENCE: 6

Val Arg Lys Ser Thr Leu Thr Phe Leu Ile Ala Gly Cys Leu Ala Leu
1               5                   10                  15

Pro Gly Phe Ala Arg Ala Ala Asp Ala Ala Asp Pro Ala Leu Val Lys
            20                  25                  30

Arg Gly Glu Tyr Leu Ala

-continued

```
Gly Val Ser Lys Asn Gly Asp Asn Leu Tyr Pro Ala Met Pro Tyr Val
              100                 105                 110

Ser Tyr Ala Lys Ile Thr Asp Asp Val Arg Ala Leu Tyr Ala Tyr
        115                 120                 125

Phe Met His Gly Val Glu Pro Val Lys Gln Ala Pro Pro Lys Asn Glu
    130                 135                 140

Ile Pro Ala Leu Leu Ser Met Arg Trp Pro Leu Lys Ile Trp Asn Trp
145                 150                 155                 160

Leu Phe Leu Lys Asp Gly Pro Tyr Gln Pro Lys Pro Ser Gln Ser Ala
                165                 170                 175

Glu Trp Asn Arg Gly Ala Tyr Leu Val Gln Gly Leu Ala His Cys Ser
        180                 185                 190

Thr Cys His Thr Pro Arg Gly Ile Ala Met Gln Glu Lys Ser Leu Asp
    195                 200                 205

Glu Thr Gly Gly Ser Phe Leu Ala Gly Ser Val Leu Ala Gly Trp Asp
210                 215                 220

Gly Tyr Asn Ile Thr Ser Asp Pro Asn Ala Gly Ile Gly Ser Trp Thr
225                 230                 235                 240

Gln Gln Gln Leu Val Gln Tyr Leu Arg Thr Gly Ser Val Pro Gly Val
                245                 250                 255

Ala Gln Ala Ala Gly Pro Met Ala Glu Ala Val Glu His Ser Phe Ser
        260                 265                 270

Lys Met Thr Glu Ala Asp Ile Gly Ala Ile Ala Thr Tyr Val Arg Thr
    275                 280                 285

Val Pro Ala Val Ala Asp Ser Asn Ala Lys Gln Pro Arg Ser Ser Trp
290                 295                 300

Gly Lys Pro Ala Glu Asp Gly Leu Lys Leu Arg Gly Val Ala Leu Ala
305                 310                 315                 320

Ser Ser Gly Ile Asp Pro Ala Arg Leu Tyr Leu Gly Asn Cys Ala Thr
                325                 330                 335

Cys His Gln Met Gln Gly Lys Gly Thr Pro Asp Gly Tyr Tyr Pro Ser
        340                 345                 350

Leu Phe His Asn Ser Thr Val Gly Ala Ser Asn Pro Ser Asn Leu Val
    355                 360                 365

Gln Val Ile Leu Asn Gly Val Gln Arg Lys Ile Gly Ser Glu Asp Ile
370                 375                 380

Gly Met Pro Ala Phe Arg Tyr Asp Leu Asn Asp Ala Gln Ile Ala Ala
385                 390                 395                 400

Leu Thr Asn Tyr Val Thr Ala Gln Phe Gly Asn Pro Ala Ala Lys Val
                405                 410                 415

Thr Glu Gln Asp Val Ala Lys Leu Arg
        420                 425

<210> SEQ ID NO 7
<211> LENGTH: 539
<212> TYPE: PRT
<213> ORGANISM: Burkholderia cenocepacia

<400> SEQUENCE: 7

Met Ala Asp Thr Asp Thr Gln Lys Ala Asp Val Val Val Val Gly Ser
1               5                   10                  15

Gly Val Ala Gly Ala Ile Val Ala His Gln Leu Ala Met Ala Gly Lys
            20                  25                  30

Ser Val Ile Leu Leu Glu Ala Gly Pro Arg Met Pro Arg Trp Glu Ile
        35                  40                  45
```

```
Val Glu Arg Phe Arg Asn Gln Pro Asp Lys Thr Asp Phe Met Ala Pro
 50                  55                  60
Tyr Pro Ser Ser Pro Trp Ala Pro His Pro Glu Tyr Gly Pro Pro Asn
 65                  70                  75                  80
Asp Tyr Leu Ile Leu Lys Gly Glu His Lys Phe Asn Ser Gln Tyr Ile
                 85                  90                  95
Arg Ala Val Gly Gly Thr Thr Trp His Trp Ala Ala Ser Ala Trp Arg
                100                 105                 110
Phe Ile Pro Asn Asp Phe Lys Met Lys Thr Val Tyr Gly Val Ala Arg
                115                 120                 125
Asp Trp Pro Ile Gln Tyr Asp Asp Leu Glu His Trp Tyr Gln Arg Ala
130                 135                 140
Glu Glu Glu Leu Gly Val Trp Gly Pro Gly Pro Glu Glu Asp Leu Tyr
145                 150                 155                 160
Ser Pro Arg Lys Gln Ala Tyr Pro Met Pro Pro Leu Pro Leu Ser Phe
                165                 170                 175
Asn Glu Gln Thr Ile Lys Ser Ala Leu Asn Gly Tyr Asp Pro Lys Phe
                180                 185                 190
His Val Val Thr Glu Pro Val Ala Arg Asn Ser Arg Pro Tyr Asp Gly
                195                 200                 205
Arg Pro Thr Cys Cys Gly Asn Asn Asn Cys Met Pro Ile Cys Pro Ile
210                 215                 220
Gly Ala Met Tyr Asn Gly Ile Val His Val Glu Lys Ala Glu Gln Ala
225                 230                 235                 240
Gly Ala Lys Leu Ile Asp Ser Ala Val Val Tyr Lys Leu Glu Thr Gly
                245                 250                 255
Pro Asp Lys Arg Ile Val Ala Ala Ile Tyr Lys Asp Lys Thr Gly Ala
                260                 265                 270
Asp His Arg Val Glu Gly Lys Tyr Phe Val Leu Ala Ala Asn Gly Ile
                275                 280                 285
Glu Thr Pro Lys Ile Leu Leu Met Ser Ala Asn Arg Asp Phe Pro Asn
290                 295                 300
Gly Val Ala Asn Ser Ser Asp Met Val Gly Arg Asn Leu Met Asp His
305                 310                 315                 320
Pro Gly Thr Gly Val Ser Phe Tyr Ala Asn Glu Lys Leu Trp Pro Gly
                325                 330                 335
Arg Gly Pro Gln Glu Met Thr Ser Leu Ile Gly Phe Arg Asp Gly Pro
                340                 345                 350
Phe Arg Ala Thr Glu Ala Ala Lys Lys Ile His Leu Ser Asn Met Ser
                355                 360                 365
Arg Ile Asn Gln Glu Thr Gln Lys Ile Phe Lys Ala Gly Lys Leu Met
                370                 375                 380
Lys His Glu Glu Leu Asp Ala Gln Ile Arg Asp Arg Ser Ala Arg Tyr
385                 390                 395                 400
Val Gln Phe Asp Cys Phe His Glu Ile Leu Pro Gln Pro Glu Asn Arg
                405                 410                 415
Ile Val Pro Ser Lys Thr Ala Asp Ala Ile Gly Ile Pro Arg Pro
                420                 425                 430
Glu Ile Thr Tyr Ala Ile Asp Asp Tyr Val Lys Arg Gly Ala Val His
                435                 440                 445
Thr Arg Glu Val Tyr Ala Thr Ala Ala Lys Val Leu Gly Gly Thr Asp
450                 455                 460
```

Val Val Phe Asn Asp Glu Phe Ala Pro Asn Asn His Ile Thr Gly Ala
465 470 475 480

Thr Ile Met Gly Ala Asp Ala Arg Asp Ser Val Val Asp Lys Asp Cys
485 490 495

Arg Thr Phe Asp His Pro Asn Leu Phe Ile Ser Ser Ser Ser Thr Met
500 505 510

Pro Thr Val Gly Thr Val Asn Val Thr Leu Thr Ile Ala Ala Leu Ala
515 520 525

Leu Arg Met Ser Asp Thr Leu Lys Lys Glu Val
530 535

<210> SEQ ID NO 8
<211> LENGTH: 537
<212> TYPE: PRT
<213> ORGANISM: Burkholderia thailandensis

<400> SEQUENCE: 8

Met Ala Glu Thr Gln Gln Ala Asp Val Val Val Val Gly Ser Gly Val
1 5 10 15

Ala Gly Ala Ile Val Ala His Gln Leu Ala Met Ala Gly Lys Ser Val
20 25 30

Ile Leu Leu Glu Ala Gly Pro Arg Met Pro Arg Trp Glu Ile Val Glu
35 40 45

Arg Phe Arg Asn Gln Pro Asp Lys Met Asp Phe Met Ala Pro Tyr Pro
50 55 60

Ser Ser Ala Trp Ala Pro His Pro Glu Tyr Ala Pro Pro Asn Asp Tyr
65 70 75 80

Leu Val Leu Lys Gly Glu His Lys Phe Asn Ser Gln Tyr Ile Arg Ala
85 90 95

Val Gly Gly Thr Thr Trp His Trp Ala Ala Ser Ala Trp Arg Phe Ile
100 105 110

Pro Asn Asp Phe Lys Met Lys Thr Val Tyr Gly Val Gly Arg Asp Trp
115 120 125

Pro Ile Gln Tyr Asp Asp Leu Glu His Phe Tyr Gln Arg Ala Glu Glu
130 135 140

Glu Leu Gly Val Trp Gly Pro Gly Ala Glu Glu Asp Leu Leu Ser Pro
145 150 155 160

Arg Lys Ala Pro Tyr Pro Met Pro Pro Leu Pro Leu Ser Tyr Asn Glu
165 170 175

Arg Thr Ile Lys Thr Ala Leu Asn Asn His Asp Pro Lys Tyr His Val
180 185 190

Val Thr Glu Pro Val Ala Arg Asn Ser Arg Pro Tyr Asp Gly Arg Pro
195 200 205

Thr Cys Cys Gly Asn Asn Asn Cys Met Pro Ile Cys Pro Ile Gly Ala
210 215 220

Met Tyr Asn Gly Ile Val His Val Glu Lys Ala Glu Gln Ala Gly Ala
225 230 235 240

Lys Leu Ile Glu Asn Ala Val Val His Lys Leu Glu Val Gly Pro Gln
245 250 255

Lys Lys Ile Val Ala Ala Leu Tyr Lys Asp Pro Lys Gly Ala Glu His
260 265 270

Arg Val Glu Gly Lys Tyr Phe Val Leu Ala Ala Asn Gly Ile Glu Thr
275 280 285

Pro Lys Leu Met Leu Met Ser Thr Ser His Asp Phe Pro Asn Gly Val
290 295 300

Gly Asn Ser Ser Asp Met Val Gly Arg Asn Leu Met Asp His Pro Gly
305                 310                 315                 320

Thr Gly Val Ser Phe Tyr Ala Ser Glu Lys Leu Trp Pro Gly Arg Gly
            325                 330                 335

Pro Gln Glu Met Thr Ser Leu Ile Gly Phe Arg Asp Gly Pro Phe Arg
                340                 345                 350

Ala Thr Glu Ala Ala Lys Lys Ile His Leu Ser Asn Leu Ser Arg Ile
            355                 360                 365

Asp Gln Glu Thr Gln Lys Ile Phe Lys Ala Gly Lys Leu Leu Lys Pro
        370                 375                 380

Ala Glu Leu Asp Ala Gln Ile Arg Asp Arg Ser Ala Arg Tyr Val Gln
385                 390                 395                 400

Phe Asp Cys Phe His Glu Ile Leu Pro Gln Pro Glu Asn Arg Ile Val
                405                 410                 415

Pro Ser Lys Thr Ala Thr Asp Ala Ile Gly Ile Pro Arg Pro Glu Ile
            420                 425                 430

Thr Tyr Ala Ile Asp Asp Tyr Val Lys Arg Gly Ala Ala His Thr Arg
            435                 440                 445

Glu Val Tyr Ala Ser Ala Ala Gln Val Leu Gly Gly Thr Asp Val Val
        450                 455                 460

Phe Asn Asp Glu Phe Ala Pro Asn Asn His Ile Thr Gly Ala Thr Ile
465                 470                 475                 480

Met Gly Ala Asp Pro Arg Asp Ser Val Asp Lys Asp Cys Arg Thr
                485                 490                 495

Phe Asp His Pro Asn Leu Phe Ile Ser Ser Ala Thr Met Pro Thr
                500                 505                 510

Val Gly Thr Val Asn Val Thr Leu Thr Ile Ala Ala Leu Ala Leu Arg
            515                 520                 525

Ile Ser Asp Gln Leu Lys Lys Glu Ile
            530                 535

<210> SEQ ID NO 9
<211> LENGTH: 540
<212> TYPE: PRT
<213> ORGANISM: Ralstonia pickettii

<400> SEQUENCE: 9

Met Ala Gln Ser Glu Gln Thr Arg Gln Gln Ala Asp Ile Val Val Val
1               5                   10                  15

Gly Ser Gly Val Ala Gly Ala Leu Val Ala Tyr Glu Leu Ala Arg Ala
            20                  25                  30

Gly Lys Ser Val Leu Met Leu Glu Ala Gly Pro Arg Leu Pro Arg Trp
        35                  40                  45

Glu Ile Val Glu Arg Phe Arg Asn Gln Ala Asp Lys Met Asp Phe Met
    50                  55                  60

Ala Pro Tyr Pro Ser Thr Ala Trp Ala Pro His Pro Glu Tyr Gly Pro
65                  70                  75                  80

Pro Asn Asn Tyr Leu Val Leu Lys Gly Glu His Gln Phe Asn Ser Gln
                85                  90                  95

Tyr Ile Arg Ala Val Gly Gly Thr Thr Trp His Trp Ala Ala Ser Thr
            100                 105                 110

Trp Arg Phe Leu Pro Asn Asp Phe Lys Leu Arg Ser Val Tyr Gly Ile
        115                 120                 125

```
Ala Arg Asp Trp Pro Ile Gln Tyr Gln Asp Leu Glu Arg Tyr Tyr Gly
    130                 135                 140

Leu Ala Glu Glu Ala Leu Gly Val Trp Gly Pro Asn Asp Glu Asp Leu
145                 150                 155                 160

Gly Ser Pro Arg Ser Gln Pro Tyr Pro Met Thr Pro Leu Pro Leu Ser
                165                 170                 175

Phe Asn Glu Arg Thr Ile Lys Glu Ala Leu Asn Ala His Asp Ala Ser
            180                 185                 190

Phe His Val Val Thr Glu Pro Val Ala Arg Asn Ser Arg Pro Tyr Asp
        195                 200                 205

Gly Arg Pro Thr Cys Cys Gly Asn Asn Asn Cys Met Pro Ile Cys Pro
210                 215                 220

Ile Gly Ala Met Tyr Asn Gly Ile Val His Val Glu Lys Ala Glu Gln
225                 230                 235                 240

Ala Gly Ala Arg Leu Ile Glu Asn Ala Val Val Phe Lys Leu Glu Val
                245                 250                 255

Gly Pro Asn Lys Arg Ile Val Ala Ala Arg Tyr Lys Asp Ser Lys Gly
                260                 265                 270

Ala Glu His Arg Val Glu Gly Lys Trp Phe Val Leu Ala Ala Asn Gly
            275                 280                 285

Ile Glu Thr Pro Lys Leu Met Leu Met Ser Thr Ser Gln Asp Phe Pro
        290                 295                 300

Lys Gly Val Gly Asn Ser Ser Asp Met Val Gly Arg Asn Leu Met Asp
305                 310                 315                 320

His Pro Gly Thr Gly Val Ser Phe Tyr Ala Asp Arg Lys Leu Trp Pro
                325                 330                 335

Gly Arg Gly Pro Gln Glu Met Thr Ser Leu Ile Gly Phe Arg Asp Gly
                340                 345                 350

Pro Phe Arg Ala Thr Gln Ala Gly Lys Lys Leu His Leu Ser Asn Ile
            355                 360                 365

Ser Arg Ile Glu Gln Glu Thr Gln Arg Ile Phe Lys Glu Gly Lys Leu
        370                 375                 380

Ile Lys Pro Ala Asp Leu Asp Ala Arg Ile Arg Asp Gln Ala Ala Arg
385                 390                 395                 400

Tyr Val Gln Phe Asp Ser Phe His Glu Ile Leu Pro Leu Pro Glu Asn
                405                 410                 415

Arg Ile Val Pro Ser Ala Thr Glu Val Asp Ala Ile Gly Ile Pro Arg
                420                 425                 430

Pro Glu Ile Thr Tyr His Ile Asp Asp Tyr Val Lys Arg Ser Ala Val
            435                 440                 445

His Thr Arg Glu Val Tyr Ala Thr Ala Ala Gln Val Met Gly Gly Thr
        450                 455                 460

Asn Val Glu Phe His Asp Asp Phe Ala Pro Asn Asn His Ile Thr Gly
465                 470                 475                 480

Ala Thr Ile Met Gly Ala Asp Pro Lys Asp Ser Val Val Asp Lys Asp
                485                 490                 495

Cys Arg Thr Phe Asp His Pro Asn Leu Phe Ile Ser Ser Ser Ser Thr
                500                 505                 510

Met Pro Thr Val Gly Thr Val Asn Val Thr Leu Thr Ile Ala Ala Leu
            515                 520                 525

Ala Leu Arg Ile Ala Asp Gln Leu Lys Gln Glu Ala
        530                 535                 540
```

```
<210> SEQ ID NO 10
<211> LENGTH: 540
<212> TYPE: PRT
<213> ORGANISM: Ralstonia solanacearum

<400> SEQUENCE: 10

Met Ala Asp Thr Ar

```
Leu Lys Pro Ala Glu Leu Asp Ala Arg Ile Arg Asp Gln Ala Ala Arg
385                 390                 395                 400

Tyr Val Gln Phe Asp Ser Phe His Glu Ile Leu Pro Leu Pro Glu Asn
            405                 410                 415

Arg Ile Val Pro Ser Ala Thr Glu Thr Asp Ala Leu Gly Ile Pro Arg
        420                 425                 430

Pro Glu Ile Thr Tyr Arg Ile Asp Asp Tyr Val Lys Arg Ser Ala Val
    435                 440                 445

His Thr Arg Glu Val Tyr Ala Thr Ala Lys Val Leu Gly Ala Thr
450                 455                 460

Asp Val Gln Phe His Asp Asp Phe Ala Pro Asn Asn His Ile Thr Gly
465                 470                 475                 480

Ala Thr Ser Met Gly Ala Asp Pro Lys Asp Ser Val Val Asp Lys Asp
            485                 490                 495

Cys Arg Thr Phe Asp His Pro Asn Leu Phe Ile Ser Ser Ala Thr
            500                 505                 510

Met Pro Thr Val Gly Thr Val Asn Val Thr Leu Thr Ile Ala Ala Leu
            515                 520                 525

Ala Leu Arg Ile Ala Asp Arg Leu Lys Lys Glu Ala
    530                 535                 540

<210> SEQ ID NO 11
<211> LENGTH: 533
<212> TYPE: PRT
<213> ORGANISM: Burkholderia phytofirmans

<400> SEQUENCE: 11

Met Ala Asn Lys Asn Ser Ala Asp Ile Val Val Gly Ser Gly Val
1               5                   10                  15

Ala Gly Gly Leu Val Ala His Gln Met Ala Leu Ala Gly Ala Ser Val
                20                  25                  30

Ile Leu Leu Glu Ala Gly Pro Arg Ile Pro Arg Trp Gln Ile Val Glu
            35                  40                  45

Asn Phe Arg Asn Ser Pro Val Lys Ser Asp Phe Ala Thr Pro Tyr Pro
50                  55                  60

Ser Thr Pro Tyr Ala Pro His Pro Glu Tyr Ala Pro Ala Asn Asn Tyr
65                  70                  75                  80

Leu Ile Gln Lys Gly Asp Tyr Pro Tyr Ser Ser Gln Tyr Leu Arg Leu
                85                  90                  95

Val Gly Gly Thr Thr Trp His Trp Ala Ala Ala Trp Arg Leu Leu
            100                 105                 110

Pro Ser Asp Phe Gln Leu His Lys Leu Tyr Gly Val Gly Arg Asp Trp
        115                 120                 125

Pro Tyr Pro Tyr Glu Thr Leu Glu Pro Trp Tyr Ser Ala Ala Glu Val
    130                 135                 140

Gln Leu Gly Val Ser Gly Pro Gly Asn Ser Ile Asp Leu Gly Ser Pro
145                 150                 155                 160

Arg Ser Lys Pro Tyr Pro Met Asn Pro Leu Pro Leu Ser Tyr Met Asp
                165                 170                 175

Gln Arg Phe Ser Asp Val Leu Asn Ala Gln Gly Phe Lys Val Val Pro
            180                 185                 190

Glu Pro Val Ala Arg Asn Ser Arg Pro Tyr Asp Ala Arg Pro Thr Cys
        195                 200                 205

Cys Gly Asn Asn Asn Cys Met Pro Ile Cys Pro Ile Ala Ala Met Tyr
    210                 215                 220
```

Asn Gly Val Val His Ala Glu Lys Ala Glu Gln Ala Gly Ala Lys Leu
225                 230                 235                 240

Ile Pro Glu Ala Val Tyr Arg Val Glu Ala Asp Asn Lys Gly Leu
            245                 250                 255

Ile Thr Ala Val His Tyr Lys Asp Pro Asn Gly Asn Ser Thr Arg Val
            260                 265                 270

Thr Gly Lys Leu Phe Val Leu Ala Ala Asn Gly Ile Glu Thr Pro Lys
            275                 280                 285

Leu Met Leu Met Ser Thr Ser Asp Lys Phe Pro His Gly Val Gly Asn
290                 295                 300

Ser Ser Asp Gln Val Gly Arg Asn Leu Met Asp His Pro Gly Thr Gly
305                 310                 315                 320

Val Thr Phe Leu Ala Asn Glu Ala Leu Trp Pro Gly Arg Gly Pro Met
            325                 330                 335

Glu Met Thr Ser Ile Val Asn Phe Arg Asp Gly Ala Phe Arg Ser Asp
            340                 345                 350

Tyr Ala Ala Lys Lys Leu His Leu Ser Asn Gly Val Pro Thr Met Ser
            355                 360                 365

Val Thr Ala Asp Leu Leu Lys Lys Gly Leu Thr Gly Ala Glu Leu Asp
370                 375                 380

Arg Gln Ile Arg Asp Arg Ala Ala Arg Thr Leu Asn Ile Asn Ser Phe
385                 390                 395                 400

His Glu His Leu Ala Glu Pro Gln Asn Arg Val Val Pro Ser Ala Asp
            405                 410                 415

His Lys Asp Ser Leu Gly Ile Pro Gln Pro Glu Ile Tyr Tyr Ser Ile
            420                 425                 430

Asn Asp Tyr Val Lys Lys Ser Ala Ala Asn Thr His Glu Leu Tyr Ala
            435                 440                 445

Gln Ile Ala Ala Leu Phe Gly Gly Ala Glu Val Thr Phe Asp Asp Thr
450                 455                 460

Phe Ala Pro Asn Asn His Ile Met Gly Thr Thr Ile Met Gly Ser Asp
465                 470                 475                 480

Pro Ala Asp Ser Val Val Asp Ala Asp Cys Arg Thr His Asp His Ser
            485                 490                 495

Asn Leu Phe Ile Ala Ser Ser Gly Val Met Pro Thr Ala Ala Ser Val
            500                 505                 510

Asn Cys Thr Leu Thr Ile Ala Ala Leu Ser Leu Lys Leu Ala Asp Lys
            515                 520                 525

Leu Lys Arg Glu Ile
            530

<210> SEQ ID NO 12
<211> LENGTH: 539
<212> TYPE: PRT
<213> ORGANISM: Burkholderia cepacia

<400> SEQUENCE: 12

Met Ala Asp Thr Asp Thr Gln Lys Ala Asp Val Val Val Val Gly Ser
1               5                   10                  15

Gly Val Ala Gly Ala Ile Val Ala His Gln Leu Ala Met Ala Gly Lys
            20                  25                  30

Ser Val Ile Leu Leu Glu Ala Gly Pro Arg Met Pro Arg Trp Glu Ile
            35                  40                  45

Val Glu Arg Phe Arg Asn Gln Val Asp Lys Thr Asp Phe Met Ala Pro
50                  55                  60

-continued

```
Tyr Pro Ser Ser Ala Trp Ala Pro His Pro Glu Tyr Gly Pro Pro Asn
 65                  70                  75                  80

Asp Tyr Leu Ile Leu Lys Gly Glu His Lys Phe Asn Ser Gln Tyr Ile
                 85                  90                  95

Arg Ala Val Gly Gly Thr Thr Trp His Trp Ala Ala Ser Ala Trp Arg
            100                 105                 110

Phe Ile Pro Asn Asp Phe Lys Met Lys Thr Val Tyr Gly Val Gly Arg
        115                 120                 125

Asp Trp Pro Ile Gln Tyr Asp Ile Glu His Tyr Tyr Gln Arg Ala
    130                 135                 140

Glu Glu Glu Leu Gly Val Trp Gly Pro Gly Pro Glu Glu Asp Leu Tyr
145                 150                 155                 160

Ser Pro Arg Lys Glu Pro Tyr Pro Met Pro Pro Leu Pro Leu Ser Phe
                165                 170                 175

Asn Glu Gln Thr Ile Lys Ser Ala Leu Asn Gly Tyr Asp Pro Lys Phe
            180                 185                 190

His Val Val Thr Glu Pro Val Ala Arg Asn Ser Arg Pro Tyr Asp Gly
        195                 200                 205

Arg Pro Thr Cys Cys Gly Asn Asn Cys Met Pro Ile Cys Pro Ile
    210                 215                 220

Gly Ala Met Tyr Asn Gly Ile Val His Val Glu Lys Ala Glu Gln Ala
225                 230                 235                 240

Gly Ala Lys Leu Ile Asp Ser Ala Val Val Tyr Lys Leu Glu Thr Gly
                245                 250                 255

Pro Asp Lys Arg Ile Thr Ala Ala Val Tyr Lys Asp Lys Thr Gly Ala
            260                 265                 270

Asp His Arg Val Glu Gly Lys Tyr Phe Val Ile Ala Ala Asn Gly Ile
        275                 280                 285

Glu Thr Pro Lys Ile Leu Leu Met Ser Ala Asn Arg Asp Phe Pro Asn
    290                 295                 300

Gly Val Ala Asn Ser Ser Asp Met Val Gly Arg Asn Leu Met Asp His
305                 310                 315                 320

Pro Gly Thr Gly Val Ser Phe Tyr Ala Asn Glu Lys Leu Trp Pro Gly
                325                 330                 335

Arg Gly Pro Gln Glu Met Thr Ser Leu Ile Gly Phe Arg Asp Gly Pro
            340                 345                 350

Phe Arg Ala Thr Glu Ala Ala Lys Lys Ile His Leu Ser Asn Met Ser
        355                 360                 365

Arg Ile Asn Gln Glu Thr Gln Lys Ile Phe Lys Ala Gly Lys Leu Met
    370                 375                 380

Lys Pro Glu Glu Leu Asp Ala Gln Ile Arg Asp Arg Ser Ala Arg Tyr
385                 390                 395                 400

Val Gln Phe Asp Cys Phe His Glu Ile Leu Pro Gln Pro Glu Asn Arg
                405                 410                 415

Ile Val Pro Ser Lys Thr Ala Thr Asp Ala Ile Gly Ile Pro Arg Pro
            420                 425                 430

Glu Ile Thr Tyr Ala Ile Asp Asp Tyr Val Lys Arg Gly Ala Val His
        435                 440                 445

Thr Arg Glu Val Tyr Ala Thr Ala Lys Val Leu Gly Gly Thr Glu
    450                 455                 460

Val Val Phe Asn Asp Glu Phe Ala Pro Asn Asn His Ile Thr Gly Ala
465                 470                 475                 480
```

```
Thr Ile Met Gly Ala Asp Ala Arg Asp Ser Val Val Asp Lys Asp Cys
                485                 490                 495

Arg Thr Phe Asp His Pro Asn Leu Phe Ile Ser Ser Ser Thr Met
            500                 505                 510

Pro Thr Val Gly Thr Val Asn Val Thr Leu Thr Ile Ala Ala Leu Ala
            515                 520                 525

Leu Arg Met Ser Asp Thr Leu Lys Lys Glu Val
            530                 535

<210> SEQ ID NO 13
<211> LENGTH: 539
<212> TYPE: PRT
<213> ORGANISM: Burkholderia cepacia

<400> SEQUENCE: 13

Met Ala Asp Thr Asp Thr Gln Lys Ala Asp Val Val Val Gly Ser
1               5                   10                  15

Gly Val Ala Gly Ala Ile Val Ala His Gln Leu Ala Met Ala Gly Lys
            20                  25                  30

Ser Val Ile Leu Leu Glu Ala Gly Pro Arg Met Pro Arg Trp Glu Ile
            35                  40                  45

Val Glu Arg Phe Arg Asn Gln Val Asp Lys Thr Asp Phe Met Ala Pro
    50                  55                  60

Tyr Pro Ser Ser Ala Trp Ala Pro His Pro Glu Tyr Gly Pro Pro Asn
65              70                  75                  80

Asp Tyr Leu Ile Leu Lys Gly Glu His Lys Phe Asn Ser Gln Tyr Ile
                85                  90                  95

Arg Ala Val Gly Gly Thr Thr Trp His Trp Ala Ala Ser Ala Trp Arg
            100                 105                 110

Phe Ile Pro Asn Asp Phe Lys Met Lys Thr Val Tyr Gly Val Gly Arg
            115                 120                 125

Asp Trp Pro Ile Gln Tyr Asp Asp Ile Glu His Tyr Tyr Gln Arg Ala
            130                 135                 140

Glu Glu Glu Leu Gly Val Trp Gly Pro Gly Pro Glu Glu Asp Leu Tyr
145                 150                 155                 160

Ser Pro Arg Lys Glu Pro Tyr Pro Met Pro Pro Leu Pro Leu Ser Phe
                165                 170                 175

Asn Glu Gln Thr Ile Lys Ser Ala Leu Asn Gly Tyr Asp Pro Lys Phe
            180                 185                 190

His Val Val Thr Glu Pro Val Ala Arg Asn Ser Arg Pro Tyr Asp Gly
            195                 200                 205

Arg Pro Thr Cys Cys Gly Asn Asn Asn Cys Met Pro Ile Cys Pro Ile
            210                 215                 220

Gly Ala Met Tyr Asn Gly Ile Val His Val Glu Lys Ala Glu Gln Ala
225                 230                 235                 240

Gly Ala Lys Leu Ile Asp Ser Ala Val Val Tyr Lys Leu Glu Thr Gly
                245                 250                 255

Pro Asp Lys Arg Ile Thr Ala Ala Val Tyr Lys Asp Lys Thr Gly Ala
            260                 265                 270

Asp His Arg Val Glu Gly Lys Tyr Phe Val Ile Ala Ala Asn Gly Ile
            275                 280                 285

Glu Thr Pro Lys Ile Leu Leu Met Ser Ala Asn Arg Asp Phe Pro Asn
            290                 295                 300

Gly Val Ala Asn Ser Ser Asp Met Val Gly Arg Asn Leu Met Asp His
305                 310                 315                 320
```

Pro Gly Thr Gly Val Ser Phe Tyr Ala Asn Glu Lys Leu Trp Pro Gly
            325                 330                 335

Arg Gly Pro Gln Glu Met Thr Ser Leu Ile Gly Phe Arg Asp Gly Pro
        340                 345                 350

Phe Arg Ala Asn Glu Ala Ala Lys Lys Ile His Leu Ser Asn Met Ser
    355                 360                 365

Arg Ile Asn Gln Glu Thr Gln Lys Ile Phe Lys Gly Gly Lys Leu Met
370                 375                 380

Lys Pro Glu Glu Leu Asp Ala Gln Ile Arg Asp Arg Ser Ala Arg Phe
385                 390                 395                 400

Val Gln Phe Asp Cys Phe His Glu Ile Leu Pro Gln Pro Glu Asn Arg
                405                 410                 415

Ile Val Pro Ser Lys Thr Ala Thr Asp Ala Val Gly Ile Pro Arg Pro
            420                 425                 430

Glu Ile Thr Tyr Ala Ile Asp Asp Tyr Val Lys Arg Gly Ala Val His
        435                 440                 445

Thr Arg Glu Val Tyr Ala Thr Ala Ala Lys Val Leu Gly Gly Thr Glu
    450                 455                 460

Val Val Phe Asn Asp Glu Phe Ala Pro Asn Asn His Ile Thr Gly Ala
465                 470                 475                 480

Thr Ile Met Gly Ala Asp Ala Arg Asp Ser Val Val Asp Lys Asp Cys
                485                 490                 495

Arg Thr Phe Asp His Pro Asn Leu Phe Ile Ser Ser Ser Thr Met
            500                 505                 510

Pro Thr Val Gly Thr Val Asn Val Thr Leu Thr Ile Ala Ala Leu Ala
        515                 520                 525

Leu Arg Met Ser Asp Thr Leu Lys Lys Glu Val
    530                 535

<210> SEQ ID NO 14
<211> LENGTH: 539
<212> TYPE: PRT
<213> ORGANISM: Burkholderia cepacia

<400> SEQUENCE: 14

Met Ala Asp Thr Asp Thr Gln Lys Ala Asp Val Val Val Val Gly Ser
1               5                   10                  15

Gly Val Ala Gly Ala Ile Val Ala His Gln Leu Ala Met Ala Gly Lys
            20                  25                  30

Ser Val Ile Leu Leu Glu Ala Gly Pro Arg Met Pro Arg Trp Glu Ile
        35                  40                  45

Val Glu Arg Phe Arg Asn Gln Thr Asp Lys Thr Asp Phe Met Ala Pro
    50                  55                  60

Tyr Pro Ser Ser Pro Trp Ala Pro His Pro Glu Tyr Gly Pro Pro Asn
65                  70                  75                  80

Asp Tyr Leu Val Leu Lys Gly Glu His Lys Phe Asn Ser Gln Tyr Ile
                85                  90                  95

Arg Ala Val Gly Gly Thr Thr Trp His Trp Ala Ala Ser Ala Trp Arg
            100                 105                 110

Phe Ile Pro Asn Asp Phe Lys Met Lys Thr Val Tyr Gly Val Gly Arg
        115                 120                 125

Asp Trp Pro Ile Gln Tyr Asp Asp Leu Glu His Tyr Tyr Gln Arg Ala
    130                 135                 140

Glu Glu Glu Leu Gly Val Trp Gly Pro Gly Pro Glu Glu Asp Leu Tyr
145                 150                 155                 160

Ser Pro Arg Arg Gln Pro Tyr Pro Met Pro Pro Leu Pro Leu Ser Phe
        165                 170                 175

Asn Glu Gln Thr Ile Lys Ser Ala Leu Asn Gly Tyr Asp Pro Lys Phe
            180                 185                 190

His Val Val Thr Glu Pro Val Ala Arg Asn Ser Arg Pro Tyr Asp Gly
            195                 200                 205

Arg Pro Thr Cys Cys Gly Asn Asn Cys Met Pro Ile Cys Pro Ile
        210                 215                 220

Gly Ala Met Tyr Asn Gly Ile Val His Val Lys Ala Glu Gln Ala
225                 230                 235                 240

Gly Ala Lys Leu Ile Glu Asn Ala Val Val Tyr Lys Leu Glu Thr Gly
            245                 250                 255

Pro Asn Lys Arg Ile Val Ala Ala Ile Tyr Lys Asp Lys Ser Gly Ala
            260                 265                 270

Asp His Arg Val Glu Gly Lys Tyr Phe Val Val Ala Ala Asn Gly Ile
            275                 280                 285

Glu Thr Pro Lys Ile Leu Leu Met Ser Ala Asn Arg Asp Phe Pro Asn
            290                 295                 300

Gly Val Ala Asn Ser Ser Asp Met Val Gly Arg Asn Leu Met Asp His
305                 310                 315                 320

Pro Gly Thr Gly Val Ser Phe Tyr Ala Asn Glu Lys Leu Trp Pro Gly
            325                 330                 335

Arg Gly Pro Gln Glu Met Thr Ser Leu Ile Gly Phe Arg Asp Gly Pro
            340                 345                 350

Phe Arg Ala Thr Glu Ala Ala Lys Lys Ile His Leu Ser Asn Met Ser
            355                 360                 365

Arg Ile Asn Gln Glu Thr Gln Lys Ile Phe Lys Gly Gly Lys Leu Met
            370                 375                 380

Lys Pro Glu Glu Leu Asp Ala Gln Ile Arg Asp Arg Ser Ala Arg Tyr
385                 390                 395                 400

Val Gln Phe Asp Cys Phe His Glu Ile Leu Pro Gln Pro Glu Asn Arg
            405                 410                 415

Ile Val Pro Ser Lys Thr Ala Thr Asp Ala Ile Gly Ile Pro Arg Pro
            420                 425                 430

Glu Ile Thr Tyr Ala Ile Asp Asp Tyr Val Lys Arg Gly Ala Val His
            435                 440                 445

Thr Cys Glu Val Tyr Ala Thr Ala Ala Lys Val Leu Gly Gly Thr Glu
450                 455                 460

Val Val Phe Asn Asp Glu Phe Ala Pro Asn Asn His Ile Thr Gly Ala
465                 470                 475                 480

Thr Ile Met Gly Ala Asp Ala Arg Asp Ser Val Val Asp Lys Asp Cys
            485                 490                 495

Arg Thr Phe Asp His Pro Asn Leu Phe Ile Ser Ser Ser Thr Met
            500                 505                 510

Pro Thr Val Gly Thr Val Asn Val Thr Leu Thr Ile Ala Ala Leu Ala
            515                 520                 525

Leu Arg Met Ser Asp Thr Leu Lys Lys Glu Val
            530                 535

<210> SEQ ID NO 15
<211> LENGTH: 539
<212> TYPE: PRT
<213> ORGANISM: Burkholderia cepacia

<400> SEQUENCE: 15

```
Met Ala Asp Thr Asp Thr Gln Lys Ala Asp Ile Val Val Gly Ser
1               5                   10                  15

Gly Val Ala Gly Ala Ile Val Ala His Gln Leu Ala Met Ala Gly Lys
            20                  25                  30

Ser Val Ile Leu Leu Glu Ala Gly Pro Arg Met Pro Arg Trp Glu Ile
            35                  40                  45

Val Glu Arg Phe Arg Asn Gln Pro Asp Lys Thr Asp Phe Met Ala Pro
    50                  55                  60

Tyr Pro Ser Ser Pro Trp Ala Pro His Pro Glu Tyr Gly Pro Pro Asn
65                  70                  75                  80

Asp Tyr Leu Ile Leu Lys Gly Glu His Lys Phe Asn Ser Gln Tyr Ile
                85                  90                  95

Arg Ala Val Gly Gly Thr Thr Trp His Trp Ala Ala Ser Ala Trp Arg
            100                 105                 110

Phe Ile Pro Asn Asp Phe Lys Met Lys Thr Val Tyr Gly Val Ala Arg
            115                 120                 125

Asp Trp Pro Ile Gln Tyr Asp Asp Leu Glu His Trp Tyr Gln Arg Ala
    130                 135                 140

Glu Glu Leu Gly Val Trp Gly Pro Gly Pro Glu Glu Asp Leu Tyr
145                 150                 155                 160

Ser Pro Arg Lys Gln Ala Tyr Pro Met Pro Pro Leu Pro Leu Ser Phe
            165                 170                 175

Asn Glu Gln Thr Ile Lys Ser Ala Leu Asn Gly Tyr Asp Pro Lys Phe
            180                 185                 190

His Val Val Thr Glu Pro Val Ala Arg Asn Ser Arg Pro Tyr Asp Gly
        195                 200                 205

Arg Pro Thr Cys Cys Gly Asn Asn Cys Met Pro Ile Cys Pro Ile
210                 215                 220

Gly Ala Met Tyr Asn Gly Ile Val His Val Glu Lys Ala Glu Gln Ala
225                 230                 235                 240

Gly Ala Lys Leu Ile Asp Ser Ala Val Val Tyr Lys Leu Glu Thr Gly
            245                 250                 255

Pro Asp Lys Arg Ile Val Ala Ala Ile Tyr Lys Asp Lys Thr Gly Ala
            260                 265                 270

Asp His Arg Val Glu Gly Lys Tyr Phe Val Leu Ala Ala Asn Gly Ile
    275                 280                 285

Glu Thr Pro Lys Ile Leu Leu Met Ser Ala Asn Arg Asp Phe Pro Asn
290                 295                 300

Gly Val Ala Asn Ser Ser Asp Met Val Gly Arg Asn Leu Met Asp His
305                 310                 315                 320

Pro Gly Thr Gly Val Ser Phe Tyr Ala Asn Glu Lys Leu Trp Pro Gly
            325                 330                 335

Arg Gly Pro Gln Glu Met Thr Ser Leu Ile Gly Phe Arg Asp Gly Pro
            340                 345                 350

Phe Arg Ala Thr Glu Ala Ala Lys Lys Ile His Leu Ser Asn Met Ser
    355                 360                 365

Arg Ile Asn Gln Glu Thr Gln Lys Ile Phe Lys Ala Gly Lys Leu Met
    370                 375                 380

Lys His Glu Glu Leu Asp Ala Gln Ile Arg Asp Arg Ser Ala Arg Tyr
385                 390                 395                 400

Val Gln Phe Asp Cys Phe His Glu Ile Leu Pro Gln Pro Glu Asn Arg
            405                 410                 415
```

-continued

```
Ile Val Pro Ser Lys Thr Ala Thr Asp Ala Ile Gly Ile Pro Arg Pro
            420                 425                 430

Glu Ile Thr Tyr Ala Ile Asp Asp Tyr Val Lys Arg Gly Ala Val His
        435                 440                 445

Thr Arg Glu Val Tyr Ala Thr Ala Ala Lys Val Leu Gly Gly Thr Asp
    450                 455                 460

Val Val Phe Asn Asp Glu Phe Ala Pro Asn Asn His Ile Thr Gly Ala
465                 470                 475                 480

Thr Ile Met Gly Ala Asp Ala Arg Asp Ser Val Val Asp Lys Asp Cys
                485                 490                 495

Arg Thr Phe Asp His Pro Asn Leu Phe Ile Ser Ser Ser Thr Met
            500                 505                 510

Pro Thr Val Gly Thr Val Asn Val Thr Leu Thr Ile Ala Ala Leu Ala
        515                 520                 525

Leu Arg Met Ser Asp Thr Leu Lys Lys Glu Val
    530                 535

<210> SEQ ID NO 16
<211> LENGTH: 539
<212> TYPE: PRT
<213> ORGANISM: Burkholderia cepacia

<400> SEQUENCE: 16

Met Ala Asp Thr Asp Thr Gln Lys Ala Asp Ile Val Val Gly Ser
1               5                   10                  15

Gly Val Ala Gly Ala Ile Val Ala His Gln Leu Ala Met Ala Gly Lys
            20                  25                  30

Ser Val Ile Leu Leu Glu Ala Gly Pro Arg Met Pro Arg Trp Glu Ile
        35                  40                  45

Val Glu Arg Phe Arg Asn Gln Pro Asp Lys Thr Asp Phe Met Ala Pro
    50                  55                  60

Tyr Pro Ser Ser Pro Trp Ala Pro His Pro Glu Tyr Gly Pro Pro Asn
65                  70                  75                  80

Asp Tyr Leu Ile Leu Lys Gly Glu His Lys Phe Asn Ser Gln Tyr Ile
                85                  90                  95

Arg Ala Val Gly Gly Thr Thr Trp His Trp Ala Ala Ser Ala Trp Arg
            100                 105                 110

Phe Ile Pro Asn Asp Phe Lys Met Lys Thr Val Tyr Gly Val Ala Arg
        115                 120                 125

Asp Trp Pro Ile Gln Tyr Asp Asp Leu Glu His Trp Tyr Gln Arg Ala
    130                 135                 140

Glu Glu Glu Leu Gly Val Trp Gly Pro Gly Pro Glu Glu Asp Leu Tyr
145                 150                 155                 160

Ser Pro Arg Lys Gln Ala Tyr Pro Met Pro Leu Pro Leu Ser Phe
                165                 170                 175

Asn Glu Gln Thr Ile Lys Ser Ala Leu Asn Gly Tyr Asp Pro Lys Phe
            180                 185                 190

His Val Val Thr Glu Pro Val Ala Arg Asn Ser Arg Pro Tyr Asp Gly
        195                 200                 205

Arg Pro Thr Cys Cys Gly Asn Asn Asn Cys Met Pro Ile Cys Pro Ile
    210                 215                 220

Gly Ala Met Tyr Asn Gly Ile Val His Val Glu Lys Ala Glu Gln Ala
225                 230                 235                 240

Gly Ala Lys Leu Ile Asp Ser Ala Val Val Tyr Lys Leu Glu Thr Gly
                245                 250                 255
```

Pro Asp Lys Arg Ile Val Ala Ala Ile Tyr Lys Asp Lys Thr Gly Ala
            260                 265                 270

Asp His Arg Val Glu Gly Lys Tyr Phe Val Leu Ala Ala Asn Gly Ile
        275                 280                 285

Glu Thr Pro Lys Ile Leu Leu Met Ser Ala Asn Arg Asp Phe Pro Asn
    290                 295                 300

Gly Val Ala Asn Ser Ser Asp Met Val Gly Arg Asn Leu Met Asp His
305                 310                 315                 320

Pro Gly Thr Gly Val Ser Phe Tyr Ala Asn Glu Lys Leu Trp Pro Gly
                325                 330                 335

Arg Gly Pro Gln Glu Met Thr Ser Leu Ile Gly Phe Arg Asp Gly Pro
            340                 345                 350

Phe Arg Ala Thr Glu Ala Ala Lys Lys Ile His Leu Ser Asn Met Ser
        355                 360                 365

Arg Ile Asn Gln Glu Thr Gln Lys Ile Phe Lys Ala Gly Lys Leu Met
    370                 375                 380

Lys His Glu Glu Leu Asp Ala Gln Ile Arg Asp Arg Ser Ala Arg Tyr
385                 390                 395                 400

Val Gln Phe Asp Cys Phe His Glu Ile Leu Pro Gln Pro Glu Asn Arg
                405                 410                 415

Ile Val Pro Ser Lys Thr Ala Thr Asp Ala Ile Gly Ile Pro Arg Pro
            420                 425                 430

Glu Ile Thr Tyr Ala Ile Asp Asp Tyr Val Lys Arg Gly Ala Val His
        435                 440                 445

Thr Arg Glu Val Tyr Ala Thr Ala Ala Lys Val Leu Gly Gly Thr Asp
    450                 455                 460

Val Val Phe Asn Asp Glu Phe Ala Pro Asn Asn His Ile Thr Gly Ala
465                 470                 475                 480

Thr Ile Met Gly Ala Asp Ala Arg Asp Ser Val Val Asp Lys Asp Cys
                485                 490                 495

Arg Thr Phe Asp His Pro Asn Leu Phe Ile Ser Ser Ser Thr Met
            500                 505                 510

Pro Thr Val Gly Thr Val Asn Val Thr Leu Thr Ile Ala Ala Leu Ala
        515                 520                 525

Leu Arg Met Ser Asp Thr Leu Lys Lys Glu Val
    530                 535

<210> SEQ ID NO 17
<211> LENGTH: 40
<212> TYPE: DNA
<213> ORGANISM: artificial sequence
<220> FEATURE:
<223> OTHER INFORMATION: primer

<400> SEQUENCE: 17
accaccactg ataaggaggt ctgaccgtgc ggaaatctac                    40

<210> SEQ ID NO 18
<211> LENGTH: 40
<212> TYPE: DNA
<213> ORGANISM: artificial sequence
<220> FEATURE:
<223> OTHER INFORMATION: primer

<400> SEQUENCE: 18
agcctgtgcg acttcttcct tcagcgatcg gtggtggtgg                    40

```
<210> SEQ ID NO 19
<211> LENGTH: 26
<212> TYPE: DNA
<213> ORGANISM: artificial sequence
<220> FEATURE:
<223> OTHER INFORMATION: primer

<400> SEQUENCE: 19
catgccatgg cacacaacga caacac                                              26

<210> SEQ ID NO 20
<211> LENGTH: 30
<212> TYPE: DNA
<213> ORGANISM: artificial sequence
<220> FEATURE:
<223> OTHER INFORMATION: primer

<400> SEQUENCE: 20
gtcgacgatc ttcttccagc cgaacatcac                                          30

<210> SEQ ID NO 21
<211> LENGTH: 9
<212> TYPE: PRT
<213> ORGANISM: Artificial Sequence
<220> FEATURE:
<223> OTHER INFORMATION: region (i)
<220> FEATURE:
<221> NAME/KEY: MISC_FEATURE
<222> LOCATION: (1)..(3)
<223> OTHER INFORMATION: Xaa is Val or Ile

<400> SEQUENCE: 21

Xaa Xaa Xaa Gly Ser Gly Val Ala Gly
1               5

<210> SEQ ID NO 22
<211> LENGTH: 11
<212> TYPE: PRT
<213> ORGANISM: Artificial Sequence
<220> FEATURE:
<223> OTHER INFORMATION: region (ii)

<400> SEQUENCE: 22

Cys Cys Gly Asn Asn Asn Cys Met Pro Ile Cys
1               5                   10

<210> SEQ ID NO 23
<211> LENGTH: 12
<212> TYPE: PRT
<213> ORGANISM: Artificial Sequence
<220> FEATURE:
<223> OTHER INFORMATION: region (iii)

<400> SEQUENCE: 23

Val Gly Arg Asn Leu Met Asp His Pro Gly Thr Gly
1               5                   10

<210> SEQ ID NO 24
<211> LENGTH: 7
<212> TYPE: PRT
<213> ORGANISM: Artificial Sequence
<220> FEATURE:
<223> OTHER INFORMATION: region (iv)
<220> FEATURE:
<221> NAME/KEY: MISC_FEATURE
<222> LOCATION: (3)..(3)
<223> OTHER INFORMATION: Xaa is Ile or Leu
```

```
<400> SEQUENCE: 24

Lys Lys Xaa His Leu Ser Asn
1               5

<210> SEQ ID NO 25
<211> LENGTH: 7
<212> TYPE: PRT
<213> ORGANISM: Artificial Sequence
<220> FEATURE:
<223> OTHER INFORMATION: region (v)
<220> FEATURE:
<221> NAME/KEY: MISC_FEATURE
<222> LOCATION: (3)..(3)
<223> OTHER INFORMATION: Xaa is Pro or Asn

<400> SEQUENCE: 25

Phe Ala Xaa Asn Asn His Ile
1               5
```